(12) United States Patent
Herr et al.

(10) Patent No.: US 8,870,967 B2
(45) Date of Patent: *Oct. 28, 2014

(54) ARTIFICIAL JOINTS USING AGONIST-ANTAGONIST ACTUATORS

(75) Inventors: Hugh M. Herr, Somerville, MA (US); Lee Harris Magnusson, Cambridge, MA (US); Ken Endo, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/608,627

(22) Filed: Oct. 29, 2009

(65) Prior Publication Data
US 2010/0241242 A1    Sep. 23, 2010

Related U.S. Application Data

(63) Continuation of application No. 11/642,993, filed on Dec. 19, 2006, now abandoned, and a
(Continued)

(51) Int. Cl.
*A61F 2/70* (2006.01)
*A61F 2/64* (2006.01)
(Continued)

(52) U.S. Cl.
CPC ... *A61F 2/64* (2013.01); *A61F 2/60* (2013.01); *A61F 2/6607* (2013.01); *A61F 2002/5003*
(Continued)

(58) Field of Classification Search
USPC .......... 623/24, 27, 42, 46, 25, 39, 40, 44, 45, 623/47, 48, 49, 50, 52, 57, 59, 61, 62, 64; 602/5, 16, 20, 21, 22, 23, 26, 27, 30; 601/5, 33, 34
See application file for complete search history.

(56) References Cited

U.S. PATENT DOCUMENTS 2,489,291 A    11/1949    Henschke et al.
2,529,968 A    11/1950    Sartin
(Continued)

FOREIGN PATENT DOCUMENTS

CN    101061984 A    10/2007
CN    101111211 A    1/2008
(Continued)

OTHER PUBLICATIONS

Herr, Hugh et al. "New Horizons for Orthotic and Prosthetic Technology: Artificial Muscle for Ambulation," The MIT Media Laboratory, pp. 1-9, 2004.
(Continued)

*Primary Examiner* — Marcia Watkins
(74) *Attorney, Agent, or Firm* — Hamilton, Brook, Smith & Reynolds, P.C.

(57) ABSTRACT

Artificial limbs and joints that behave like biological limbs and joints employ a synthetic actuator which consumes negligible power when exerting zero force, consumes negligible power when outputting force at constant length (isometric) and while performing dissipative, nonconservative work, is capable of independently engaging flexion and extension tendon-like, series springs, is capable of independently varying joint position and stiffness, and exploits series elasticity for mechanical power amplification.

18 Claims, 18 Drawing Sheets

Related U.S. Application Data continuation-in-part of application No. 11/395,448, filed on Mar. 31, 2006, now abandoned, and a continuation-in-part of application No. 11/499,853, filed on Aug. 4, 2006, now Pat. No. 7,313,463, and a continuation-in-part of application No. 11/495,140, filed on Jul. 29, 2006, now abandoned, which is a continuation-in-part of application No. 11/395,448, filed on Mar. 31, 2006, now abandoned, and a continuation-in-part of application No. 11/600,291, filed on Nov. 15, 2006, now abandoned.

(60) Provisional application No. 60/751,680, filed on Dec. 19, 2005, provisional application No. 60/666,876, filed on Mar. 31, 2005, provisional application No. 60/705,651, filed on Aug. 4, 2005, provisional application No. 60/704,517, filed on Aug. 1, 2005, provisional application No. 60/736,929, filed on Nov. 15, 2005.

(51) Int. Cl.
| | | |
|---|---|---|
| *A61F 2/66* | (2006.01) | |
| *A61F 5/00* | (2006.01) | |
| *A61F 2/60* | (2006.01) | |
| *A61F 2/68* | (2006.01) | |
| *B62D 57/032* | (2006.01) | |
| *B25J 19/00* | (2006.01) | |
| *A61F 2/50* | (2006.01) | |
| *A61F 2/76* | (2006.01) | |
| *A61F 2/72* | (2006.01) | |
| *A61F 2/74* | (2006.01) | |

(52) U.S. Cl.
CPC .. (2013.01); *A61F 2002/503* (2013.01); *A61F 2/68* (2013.01); *A61F 2002/6818* (2013.01); *A61F 2002/704* (2013.01); *A61F 2002/701* (2013.01); *A61F 2002/5033* (2013.01); *B62D 57/032* (2013.01); *A61F 2002/5075* (2013.01); *A61F 2002/7635* (2013.01); *A61F 2002/763* (2013.01); *A61F 2/605* (2013.01); *A61F 2002/6657* (2013.01); *B25J 19/0008* (2013.01); *A61F 2002/7645* (2013.01); *A61F 2002/5004* (2013.01); *A61F 2/72* (2013.01); *A61F 2002/764* (2013.01); *A61F 2002/7625* (2013.01); *A61F 2002/741* (2013.01)
USPC ........ 623/24; 623/39; 623/47; 601/5; 602/16; 602/26; 602/27

(56) References Cited

U.S. PATENT DOCUMENTS

| | | | |
|---|---|---|---|
| 3,016,760 A * | 1/1962 | Wrighton et al. | 74/501.5 R |
| 3,098,645 A | 7/1963 | Owens | |
| 3,207,497 A | 9/1965 | Schoonover | |
| 3,844,279 A | 10/1974 | Konvalin | |
| 3,871,032 A * | 3/1975 | Karas | 623/26 |
| 4,442,390 A | 4/1984 | Davis | |
| 4,463,291 A | 7/1984 | Usry | |
| 4,518,307 A | 5/1985 | Bloch | |
| 4,532,462 A | 7/1985 | Washbourn et al. | |
| 4,546,295 A | 10/1985 | Wickham et al. | |
| 4,546,296 A | 10/1985 | Washbourn et al. | |
| 4,546,297 A | 10/1985 | Washbourn et al. | |
| 4,546,298 A | 10/1985 | Wickham et al. | |
| 4,569,352 A | 2/1986 | Petrofsky et al. | |
| 4,600,357 A | 7/1986 | Coules | |
| 4,657,470 A | 4/1987 | Clarke et al. | |
| 4,843,921 A | 7/1989 | Kremer | |
| 4,865,376 A | 9/1989 | Leaver et al. | |
| 4,872,803 A | 10/1989 | Asakawa | |
| 4,909,535 A | 3/1990 | Clark et al. | |
| 4,921,293 A | 5/1990 | Ruoff et al. | |
| 4,921,393 A | 5/1990 | Andeen et al. | |
| 4,923,474 A | 5/1990 | Klasson et al. | |
| 4,923,475 A | 5/1990 | Gosthnian et al. | |
| 4,936,295 A | 6/1990 | Crane | |
| 4,964,402 A | 10/1990 | Grim et al. | |
| 4,989,161 A | 1/1991 | Oaki | |
| 5,012,591 A | 5/1991 | Asakawa | |
| 5,049,797 A | 9/1991 | Phillips | |
| 5,062,673 A | 11/1991 | Mimura | |
| 5,088,478 A | 2/1992 | Grim | |
| 5,092,902 A | 3/1992 | Adams et al. | |
| 5,112,296 A | 5/1992 | Beard et al. | |
| 5,174,168 A | 12/1992 | Takagi et al. | |
| 5,181,933 A | 1/1993 | Phillips | |
| 5,252,102 A | 10/1993 | Singer et al. | |
| 5,294,873 A | 3/1994 | Seraji | |
| RE34,661 E | 7/1994 | Grim | |
| 5,327,790 A | 7/1994 | Levin et al. | |
| 5,367,790 A | 11/1994 | Gamow et al. | |
| 5,383,939 A | 1/1995 | James | |
| 5,405,409 A | 4/1995 | Knoth | |
| 5,442,270 A | 8/1995 | Tetsuaki | |
| 5,443,521 A | 8/1995 | Knoth et al. | |
| 5,456,341 A | 10/1995 | Garnjost et al. | |
| 5,458,143 A | 10/1995 | Herr | |
| 5,476,441 A | 12/1995 | Durfee et al. | |
| 5,502,363 A | 3/1996 | Tasch et al. | |
| 5,514,185 A | 5/1996 | Phillips | |
| 5,556,422 A | 9/1996 | Powell, III et al. | |
| 5,571,205 A | 11/1996 | James | |
| 5,643,332 A | 7/1997 | Stein | |
| 5,650,704 A | 7/1997 | Pratt et al. | |
| 5,662,693 A | 9/1997 | Johnson et al. | |
| 5,701,686 A | 12/1997 | Herr et al. | |
| 5,718,925 A | 2/1998 | Kristinsson et al. | |
| 5,748,845 A | 5/1998 | Labun et al. | |
| 5,776,205 A | 7/1998 | Phillips | |
| 5,885,809 A | 3/1999 | Effenberger et al. | |
| 5,888,212 A | 3/1999 | Petrofsky et al. | |
| 5,888,213 A | 3/1999 | Sears et al. | |
| 5,898,948 A | 5/1999 | Kelly et al. | |
| 5,910,720 A | 6/1999 | Williamson et al. | |
| 5,932,230 A | 8/1999 | DeGrate | |
| 5,944,760 A | 8/1999 | Christensen | |
| 5,971,729 A | 10/1999 | Kristinsson et al. | |
| 5,972,036 A | 10/1999 | Kristinsson et al. | |
| 5,980,435 A | 11/1999 | Joutras et al. | |
| 6,029,374 A | 2/2000 | Herr et al. | |
| 6,056,712 A | 5/2000 | Grim | |
| 6,067,892 A | 5/2000 | Erickson | |
| 6,071,313 A | 6/2000 | Phillips | |
| 6,136,039 A | 10/2000 | Kristinsson et al. | |
| 6,144,385 A | 11/2000 | Girard | |
| 6,202,806 B1 | 3/2001 | Sandrin et al. | |
| 6,223,648 B1 | 5/2001 | Erickson | |
| 6,240,797 B1 | 6/2001 | Morishima et al. | |
| 6,267,742 B1 | 7/2001 | Krivosha et al. | |
| 6,416,703 B1 | 7/2002 | Kristinsson et al. | |
| 6,443,993 B1 | 9/2002 | Koniuk | |
| 6,456,884 B1 | 9/2002 | Kenney | |
| 6,478,826 B1 | 11/2002 | Phillips et al. | |
| 6,485,776 B2 | 11/2002 | Janusson et al. | |
| 6,507,757 B1 | 1/2003 | Swain et al. | |
| 6,511,512 B2 | 1/2003 | Phillips et al. | |
| 6,517,503 B1 | 2/2003 | Naft et al. | |
| 6,532,400 B1 | 3/2003 | Jacobs | |
| 6,585,774 B2 | 7/2003 | Dean, Jr. et al. | |
| 6,589,289 B2 | 7/2003 | Ingimarsson | |
| 6,592,539 B1 | 7/2003 | Einarsson et al. | |
| 6,610,101 B2 | 8/2003 | Herr et al. | |
| 6,626,952 B2 | 9/2003 | Janusson et al. | |
| 6,660,042 B1 | 12/2003 | Curcie et al. | |
| 6,666,796 B1 | 12/2003 | MacCready | |
| 6,706,364 B2 | 3/2004 | Janusson et al. | |
| 6,752,774 B2 | 6/2004 | Townsend et al. | |
| 6,764,520 B2 | 7/2004 | Deffenbaugh et al. | |

(56) References Cited

U.S. PATENT DOCUMENTS

| | | | |
|---|---|---|---|
| 6,811,571 B1 | 11/2004 | Phillips | |
| D503,480 S | 3/2005 | Ingimundarson et al. | |
| D503,802 S | 4/2005 | Bjarnason | |
| 6,887,279 B2 | 5/2005 | Phillips et al. | |
| 6,923,834 B2 | 8/2005 | Karason | |
| 6,936,073 B2 | 8/2005 | Karason | |
| 6,942,629 B2 | 9/2005 | Hepburn et al. | |
| 6,945,947 B2 | 9/2005 | Ingimundarson et al. | |
| 6,966,882 B2 | 11/2005 | Horst | |
| 6,969,408 B2 | 11/2005 | Lecomte et al. | |
| 7,001,563 B2 | 2/2006 | Jansson et al. | |
| 7,025,793 B2 | 4/2006 | Egilsson | |
| 7,029,500 B2 | 4/2006 | Martin | |
| 7,037,283 B2 | 5/2006 | Karason et al. | |
| D523,149 S | 6/2006 | Bjarnason | |
| 7,063,727 B2 | 6/2006 | Phillips et al. | |
| 7,077,818 B2 | 7/2006 | Ingimundarson et al. | |
| 7,094,058 B2 | 8/2006 | Einarsson | |
| 7,094,212 B2 | 8/2006 | Karason et al. | |
| D527,825 S | 9/2006 | Ingimundarson et al. | |
| D529,180 S | 9/2006 | Ingimundarson et al. | |
| 7,101,487 B2 | 9/2006 | Hsu et al. | |
| 7,105,122 B2 | 9/2006 | Karason | |
| 7,107,180 B2 | 9/2006 | Karason | |
| 7,118,601 B2 | 10/2006 | Yasui et al. | |
| 7,118,602 B2 | 10/2006 | Bjarnason | |
| 7,136,722 B2 | 11/2006 | Nakamura et al. | |
| D533,280 S | 12/2006 | Wyatt et al. | |
| 7,144,429 B2 | 12/2006 | Carstens | |
| 7,145,305 B2 | 12/2006 | Takenaka et al. | |
| 7,154,017 B2 | 12/2006 | Sigurjonsson et al. | |
| 7,161,056 B2 | 1/2007 | Gudnason et al. | |
| 7,169,188 B2 | 1/2007 | Carstens | |
| 7,169,189 B2 | 1/2007 | Bjarnason et al. | |
| 7,169,190 B2 | 1/2007 | Phillips et al. | |
| 7,198,071 B2 | 4/2007 | Bisbee et al. | |
| 7,198,610 B2 | 4/2007 | Ingimundarson et al. | |
| 7,217,060 B2 | 5/2007 | Ingimarsson | |
| 7,220,889 B2 | 5/2007 | Sigurjonsson et al. | |
| 7,223,899 B2 | 5/2007 | Sigurjonsson | |
| 7,227,050 B2 | 6/2007 | Sigurjonsson et al. | |
| 7,230,154 B2 | 6/2007 | Sigurjonsson | |
| 7,235,108 B2 | 6/2007 | Carstens | |
| 7,240,876 B2 | 7/2007 | Doubleday et al. | |
| 7,266,910 B2 | 9/2007 | Ingimundarson | |
| 7,270,644 B2 | 9/2007 | Ingimundarson | |
| 7,279,009 B2 | 10/2007 | Herr et al. | |
| 7,288,076 B2 | 10/2007 | Grim et al. | |
| 7,295,892 B2 | 11/2007 | Herr et al. | |
| RE39,961 E | 12/2007 | Petrofsky et al. | |
| 7,303,538 B2 | 12/2007 | Grim et al. | |
| 7,304,202 B2 | 12/2007 | Sigurjonsson et al. | |
| 7,311,686 B1 | 12/2007 | Iglesias et al. | |
| 7,313,463 B2 | 12/2007 | Herr et al. | |
| D558,884 S | 1/2008 | Ingimundarson et al. | |
| 7,335,233 B2 | 2/2008 | Hsu et al. | |
| 7,347,877 B2 | 3/2008 | Clausen et al. | |
| D567,072 S | 4/2008 | Ingimundarson et al. | |
| 7,371,262 B2 | 5/2008 | Lecomte et al. | |
| 7,377,944 B2 | 5/2008 | Jansson et al. | |
| RE40,363 E | 6/2008 | Grim et al. | |
| 7,381,860 B2 | 6/2008 | Gudnason et al. | |
| 7,393,364 B2 | 7/2008 | Martin | |
| 7,396,975 B2 | 7/2008 | Sigurjonsson et al. | |
| 7,402,721 B2 | 7/2008 | Sigurjonsson et al. | |
| 7,411,109 B2 | 8/2008 | Sigurjonsson et al. | |
| D576,781 S | 9/2008 | Chang et al. | |
| D577,828 S | 9/2008 | Ingimundarson et al. | |
| 7,423,193 B2 | 9/2008 | Sigurjonsson et al. | |
| 7,427,297 B2 | 9/2008 | Patterson et al. | |
| 7,429,253 B2 | 9/2008 | Shimada et al. | |
| 7,431,708 B2 | 10/2008 | Sreeramagiri | |
| 7,431,737 B2 | 10/2008 | Ragnarsdottir et al. | |
| 7,438,843 B2 | 10/2008 | Asgeirsson | |
| 7,449,005 B2 | 11/2008 | Pickering et al. | |
| 7,455,696 B2 | 11/2008 | Bisbee, III et al. | |
| D583,956 S | 12/2008 | Chang et al. | |
| 7,459,598 B2 | 12/2008 | Sigurjonsson et al. | |
| 7,465,281 B2 | 12/2008 | Grim et al. | |
| 7,465,283 B2 | 12/2008 | Grim et al. | |
| 7,468,471 B2 | 12/2008 | Sigurjonsson et al. | |
| 7,470,830 B2 | 12/2008 | Sigurjonsson et al. | |
| 7,485,152 B2 * | 2/2009 | Haynes et al. | 623/24 |
| 7,488,349 B2 | 2/2009 | Einarsson | |
| 7,488,864 B2 | 2/2009 | Sigurjonsson et al. | |
| D588,753 S | 3/2009 | Ingimundarson et al. | |
| 7,503,937 B2 | 3/2009 | Asgeirsson et al. | |
| 7,513,880 B2 | 4/2009 | Ingimundarson et al. | |
| 7,513,881 B1 | 4/2009 | Grim et al. | |
| D592,755 S | 5/2009 | Chang et al. | |
| D592,756 S | 5/2009 | Chang et al. | |
| 7,527,253 B2 | 5/2009 | Sugar et al. | |
| 7,531,006 B2 | 5/2009 | Clausen et al. | |
| 7,531,711 B2 | 5/2009 | Sigurjonsson et al. | |
| 7,534,220 B2 | 5/2009 | Cormier et al. | |
| 7,544,214 B2 | 6/2009 | Gramnas | |
| 7,549,970 B2 | 6/2009 | Tweardy | |
| D596,301 S | 7/2009 | Campos et al. | |
| 7,578,799 B2 | 8/2009 | Thorsteinsson et al. | |
| 7,581,454 B2 | 9/2009 | Clausen et al. | |
| 7,597,672 B2 | 10/2009 | Kruijsen et al. | |
| 7,597,674 B2 | 10/2009 | Hu et al. | |
| 7,597,675 B2 | 10/2009 | Ingimundarson et al. | |
| 7,618,463 B2 | 11/2009 | Oddsson et al. | |
| 7,632,315 B2 | 12/2009 | Egilsson | |
| 7,637,957 B2 | 12/2009 | Ragnarsdottir et al. | |
| 7,637,959 B2 | 12/2009 | Clausen et al. | |
| 7,641,700 B2 * | 1/2010 | Yasui | 623/40 |
| 7,650,204 B2 | 1/2010 | Dariush | |
| 7,662,191 B2 | 2/2010 | Asgeirsson | |
| D611,322 S | 3/2010 | Robertson | |
| 7,674,212 B2 | 3/2010 | Kruijsen et al. | |
| 7,691,154 B2 | 4/2010 | Asgeirsson et al. | |
| 7,696,400 B2 | 4/2010 | Sigurjonsson et al. | |
| 7,704,218 B2 | 4/2010 | Einarsson et al. | |
| D616,555 S | 5/2010 | Thorgilsdottir et al. | |
| D616,556 S | 5/2010 | Hu | |
| 7,713,225 B2 | 5/2010 | Ingimundarson et al. | |
| D616,996 S | 6/2010 | Thorgilsdottir et al. | |
| D616,997 S | 6/2010 | Thorgilsdottir et al. | |
| D618,359 S | 6/2010 | Einarsson | |
| 7,727,174 B2 | 6/2010 | Chang et al. | |
| 7,736,394 B2 | 6/2010 | Bedard et al. | |
| 7,745,682 B2 | 6/2010 | Sigurjonsson et al. | |
| D620,124 S | 7/2010 | Einarsson | |
| 7,749,183 B2 | 7/2010 | Ingimundarson et al. | |
| 7,749,281 B2 | 7/2010 | Egilsson | |
| 7,762,973 B2 | 7/2010 | Einarsson et al. | |
| 7,770,842 B2 | 8/2010 | Benson | |
| 7,771,488 B2 | 8/2010 | Asgeirsson et al. | |
| 7,780,741 B2 | 8/2010 | Jansson et al. | |
| 7,794,418 B2 | 9/2010 | Ingimundarson et al. | |
| 7,794,505 B2 | 9/2010 | Clausen et al. | |
| 7,811,333 B2 | 10/2010 | Jonsson et al. | |
| 7,811,334 B2 | 10/2010 | Ragnarsdottir et al. | |
| D627,079 S | 11/2010 | Robertson | |
| 7,833,181 B2 | 11/2010 | Cormier et al. | |
| 7,842,848 B2 | 11/2010 | Jansson et al. | |
| D628,696 S | 12/2010 | Robertson | |
| D629,115 S | 12/2010 | Robertson | |
| 7,846,213 B2 | 12/2010 | Lecomte et al. | |
| 7,862,620 B2 | 1/2011 | Clausen et al. | |
| 7,863,797 B2 | 1/2011 | Calley | |
| 7,867,182 B2 | 1/2011 | Iglesias et al. | |
| 7,867,284 B2 | 1/2011 | Bedard | |
| 7,867,285 B2 | 1/2011 | Clausen et al. | |
| 7,867,286 B2 | 1/2011 | Einarsson | |
| 7,868,511 B2 | 1/2011 | Calley | |
| 7,879,110 B2 | 2/2011 | Phillips | |
| 7,891,258 B2 | 2/2011 | Clausen et al. | |
| 7,892,195 B2 | 2/2011 | Grim et al. | |
| D634,438 S | 3/2011 | Hu | |
| D634,852 S | 3/2011 | Hu | |
| 7,896,826 B2 | 3/2011 | Hu et al. | |

(56) References Cited

U.S. PATENT DOCUMENTS

| | | |
|---|---|---|
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |
| D643,537 S | 8/2011 | Lee |
| 7,992,849 B2 | 8/2011 | Sugar et al. |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| RE42,903 E | 11/2011 | Deffenbaugh et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 8,075,633 B2 | 12/2011 | Herr et al. |
| 8,202,325 B2 | 6/2012 | Albrecht-Laatsch et al. |
| 8,287,477 B1 | 10/2012 | Herr et al. |
| 8,376,971 B1 | 2/2013 | Herr et al. |
| 8,419,804 B2 | 4/2013 | Herr et al. |
| 8,500,823 B2 | 8/2013 | Herr et al. |
| 8,512,415 B2 * | 8/2013 | Herr et al. .................. 623/24 |
| 8,734,528 B2 | 5/2014 | Herr et al. |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |
| 2003/0195439 A1 | 10/2003 | Caselnova |
| 2004/0039454 A1 | 2/2004 | Herr et al. |
| 2004/0049290 A1 | 3/2004 | Bedard |
| 2004/0054423 A1 | 3/2004 | Martin |
| 2004/0064195 A1 | 4/2004 | Herr |
| 2004/0088025 A1 | 5/2004 | Gesotti |
| 2004/0181118 A1 | 9/2004 | Kochamba |
| 2004/0181289 A1 | 9/2004 | Bedard et al. |
| 2005/0007834 A1 | 1/2005 | Hidaka |
| 2005/0043614 A1 | 2/2005 | Huizenga et al. |
| 2005/0049652 A1 | 3/2005 | Tong |
| 2005/0059908 A1 | 3/2005 | Bogert |
| 2005/0085948 A1 | 4/2005 | Herr et al. |
| 2005/0155444 A1 | 7/2005 | Otaki et al. |
| 2005/0209707 A1 | 9/2005 | Phillips et al. |
| 2005/0228515 A1 | 10/2005 | Musallam et al. |
| 2006/0004307 A1 | 1/2006 | Horst |
| 2006/0064047 A1 | 3/2006 | Shimada et al. |
| 2006/0069448 A1 | 3/2006 | Yasui |
| 2006/0094989 A1 | 5/2006 | Scott et al. |
| 2006/0122711 A1 | 6/2006 | Bedard et al. |
| 2006/0213305 A1 | 9/2006 | Sugar et al. |
| 2006/0224246 A1 | 10/2006 | Clausen et al. |
| 2006/0249315 A1 | 11/2006 | Herr et al. |
| 2006/0258967 A1 | 11/2006 | Fujil et al. |
| 2006/0264790 A1 | 11/2006 | Kruijsen et al. |
| 2006/0276728 A1 | 12/2006 | Ashihara et al. |
| 2007/0016329 A1 | 1/2007 | Herr et al. |
| 2007/0043449 A1 | 2/2007 | Herr et al. |
| 2007/0050044 A1 * | 3/2007 | Haynes et al. .................. 623/24 |
| 2007/0123997 A1 | 5/2007 | Herr et al. |
| 2007/0129653 A1 | 6/2007 | Sugar et al. |
| 2007/0145930 A1 | 6/2007 | Zaier |
| 2007/0162152 A1 | 7/2007 | Herr et al. |
| 2007/0267791 A1 | 11/2007 | Hollander et al. |
| 2008/0114272 A1 | 5/2008 | Herr et al. |
| 2008/0155444 A1 | 6/2008 | Pannese et al. |
| 2008/0169729 A1 | 7/2008 | Asai |
| 2009/0030530 A1 | 1/2009 | Martin |
| 2009/0222105 A1 | 9/2009 | Clausen |
| 2010/0324699 A1 | 12/2010 | Herr et al. |
| 2011/0040216 A1 | 2/2011 | Herr et al. |
| 2011/0224804 A1 | 9/2011 | Clausen et al. |
| 2011/0245931 A1 | 10/2011 | Clausen et al. |
| 2011/0260380 A1 | 10/2011 | Hollander et al. |
| 2011/0264230 A1 | 10/2011 | Herr et al. |
| 2011/0278857 A1 | 11/2011 | Sugar et al. |
| 2012/0136459 A1 | 5/2012 | Herr et al. |
| 2012/0209405 A1 | 8/2012 | Herr et al. |
| 2012/0271433 A1 | 10/2012 | Galea et al. |
| 2013/0110256 A1 | 5/2013 | Herr et al. |
| 2013/0158444 A1 | 6/2013 | Herr et al. |
| 2013/0197318 A1 | 8/2013 | Herr et al. |
| 2013/0310979 A1 | 11/2013 | Herr et al. |
| 2014/0046455 A1 | 2/2014 | Herr et al. |
| 2014/0088729 A1 | 3/2014 | Herr et al. |
| 2014/0257519 A1 | 9/2014 | Herr et al. |

FOREIGN PATENT DOCUMENTS

| | | |
|---|---|---|
| EP | 1393866 | 3/2004 |
| EP | 1408892 | 4/2004 |
| EP | 1534117 | 6/2005 |
| JP | 2008-87143 A | 4/2008 |
| WO | WO 01/54630 A1 | 8/2001 |
| WO | WO 03/005934 A2 | 1/2003 |
| WO | WO 03/068453 | 8/2003 |
| WO | WO 2004/017872 A1 | 3/2004 |
| WO | WO 2004/019832 * | 3/2004 |
| WO | WO 2004/019832 A1 | 3/2004 |
| WO | WO 2010/027968 A2 | 3/2010 |
| WO | WO 2010/088616 | 8/2010 |
| WO | WO 2010/088635 A1 | 8/2010 |

OTHER PUBLICATIONS

Williamson, Matthew M., "Series Elastic Actuators," MIT Artificial Intelligence Laboratory, Jan. 1995.

Au, S.K. et al., "Powered Ankle-Foot Prosthesis for the Improvement of Amputee Ambulation," paper presented at the Proceedings of the 29th Annual International Conference of the IEEE Eng. Med. Bio. Soc., Cité Internationale, Lyon, France, (Aug. 2007).

International Search Report and Written Opinion for corresponding International Application No. PCT/US2010/022783, Dated: May 4, 2010.

Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003), 88 pages.

Blaya, J.A. et al., "Adaptive Control of a Variable-Impedance Ankle-Foot Orthosis to Assist Drop Foot Gait," Artificial Intelligence Lab and Harvard-MIT Division Health Sciences and Technology, Boston, MA, 30 pages.

Blaya, J.A. et al., "Active Ankle Foot Orthoses (AAFO)," Retrieved from: http://www.ai,mit.edu.Artificial Intelligence Laboratory, Massachusetts Institute of Technology, Cambridge, Massachusetts, 3 pages.

(56) References Cited

OTHER PUBLICATIONS

Dollar, et al., "Lower Extremity Exoskeletons and Active Orthoses: Challenges and State-of-the-Art," *IEEE Transcations on Robotics*, vol. 24, No. 1, Feb. 2008, 15 pages.
Drake, C., "Foot & Ankle Splints or Orthoses," HemiHelp Information Sheet, London, United Kingdom, 3 pages, http://www.hemihelp.org.uk/leaflets/hbleaflets90.htm Retrieved on: Jun. 20, 2003.
Hogan, N., "Impedance Control: An Approach to Manipulation," Dept. of Mechanical Engineering and Labortory of Manufacturing and Productivity, Massachusetts Institute of Technology, Cambridge MA, pp. 304-313 (Jun. 1984).
Hogan, N., "Impedance Control: An Approach to Manipulation: Part II—Implementation," *Journal of Dynamic Systems, Measurement and Control*, 107: 8-16 (1985).
Hogan, N., "Impedance Control: An Approach to Manipulation: Part III—Application," *Journal of Dynamics Systems, Measurement and Control*, 107: 17-24 (1985).
Kim, J.-H. et al., "Realization of Dynamic Walking for the Humaniod Robot Platform KHR-1," *Advanced Robotics*, 18(7): 749-768, (2004).
Klute, G.K. et al., "Powering Lower Limb Prosthestics with Muscle-Like Actuators," Abstract in: Proceeding of the 1st Annual Meeting of the VA Rehabilitation Research and Development Service, "Enabling Veterans: Meeting the Challenge of Rehabilitation in the Next Millennium," Washington, D.C., p. 52 (Oct. 1998).
Klute, G.K. et al., "Artificial Muscles: Actuators for Biorobotic Systems," *The International Journal of Robotics Research*, 21(4): 295-309 (2002).
Klute, G.K. et al., "Artificial Muscles: Actuators for Lower Limb Prostheses," Abstract in: Proceedings of the 2nd Annual Meeting of the VA rehabilitation Research and Development Service, Feb. 20-22, 2000, p. 107.
Klute, G.K. et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.
Klute, G.K. et al., "Intelligent Transtibial Prostheses with Muscle-Like Actuators," 2002 American Physiological Society Intersociety Meeting: The Power of Comparative Physiology: Evolution, Integration, and Applied, 1 page.
Klute, G.K. et al., "Lower Limb Prostheses Powered by Muscle-Like Pneumatic Actuator," Submitted to Oleodinamica e Pneumatica, Publishe Tecniche Nuove, Milamo, Italy, Mar. 15, 2000, 6 pages.
Klute, G.K. et al., "McKibben Artificial Muscles: Pneumatic Actuators with Biomechanical Intelligence," IEEE/ASME 1999 International Conference on Advanced Intelligent Mechatronics, Atlanta, GA, pp. 221-226 (Sep. 1999).
Klute, G.K. et al., "Muscle-Like Pneumatic Actuators for Below-Knee Prostheses," Actuator 2000: 7th International Conference on New Actuators, Bremen, Germany on Jun. 9-21, 2000, pp. 289-292.
Klute, G.K. et al., "Variable Stiffness Prosthesis for Transtibial Amputees," Dept of Veteran Affairs, Seattle, WA USA, 2 pages.
International Search Report and Written Opinion for International Application No. PCT/US2009/055600, Mailed: Apr. 29, 2010 (23 pages).
International Search Report and Written Opinion for International Application No. PCT/US2010/047279, Mailed: Jan. 19, 2011 (11 pages).
International Search Report and Written Opinion for International Application No. PCT/US2011/031105, Mailed: Oct. 11, 2011 (16 pages).
J. Hitt et al., "The Sparky (Spring Ankle with Regenerative Kinetics) Projects: Design and Analysis of a Robotic Transtibial prosthesis with Regenerative Kinetics," in Proc. IEEE Int. Conf. Robot. Autom., Orlando, Fla., pp. 2939-2945, May 2006.
Sup, F. et al., "Design and Control of a Powered Transfemoral Prosthesis," *The International Journal of Robotics Research*, vol. 27, No. 2, pp. 263-273 (2008).
Geyer, H. et al., "A Muscle-Reflex Model That Encodes Principles of Legged Mechanics Predicts Human Walking Dynamics and Muscle Activities," *IEEE Transactions on Neural Systems and Rehabilitation Engineering*, vol. 18, No. 3, pp. 263-273 (Jun. 2010).
Geyer, H. et al., "Positive Force Feedback in Bouncing Gaits?," *Proc. R Society. Lond. B*, 270, pp. 2173-2183 (2003).
Abbas, J.J. et al., "Neural Network Control of Functional Neuromuscular Stimulation Systems: Computer Simulation Studies," *IEEE Transactions on Biomedical Engineering*, vol. 42, No. 11, Nov. 1995, pp. 1117-1127.
Abul-Haj, C.J. et al., "Functional Assessment of Control Systems for Cybernetic Elbow Prostheses—Part II: Application of the Technique," *IEEE Transactions on Biomedical Engineering*, vol. 17, No. 11, Nov. 1990, pp. 1037-1047.
Akazawa, K. et al., "Biomimetic EMG-Prosthesis-Hand, $18^{th}$ Annual International Conference of the IEEE Engineering in Medicine and Biology Society," Amsterdam 1996, pp. 535 and 536.
Aminian, K. et al., "Estimation of Speed and Incline of Walking Using Neural Network," *IEEE Transactions of Instrumentation and Measurement*, 44(3): 743-746 (1995).
Anderson, F.C. et al., "Dynamic Optimization of Human Walking," *Journal of Biomechanical Engineering*, 123: 381-390 (2001).
Andrews, B.J. et al., "Hybrid FES Orthosis Incorporating Closed Loop Control and Sensory Feedback," *J. Biomed. Eng.*, 10: 189-195(1988).
Au, S.K. et al., "An Ankle-Foot Emulation System for the Study of Human Walking Biomechanics," Proceedings of the 2006 IEEE International Conference on Robotics and Automation, Orlando, FLA, May 2006, pp. 2939-2945.
Au, S.K. et al., "Biomechanical Design of a Powered Ankle-Foot Prosthesis," Proceedings of the 2007 IEEE $10^{th}$ International Conference on Rehabilitation Robotics, Noordwijk, The Netherlands, Jun. 12-15, pp. 298-303.
Au, S.K. et al., "An EMG-Position Controlled System for an Active Ankle-Foot Prosthesis: An Initial Experimental Study," Proceedings of the 2005 IEEE $9^{th}$ International Conference on Rehabilitation Robotics, Chicago, IL., pp. 375-379.
Au, S.K. et al., "Initial Experimental Study on Dynamic Interaction Between an Amputee and a Powered Ankle-Foot Prostheses," Harvard-MIT Division of Health Sciences and Technology, MIT, Cambridge, MA.
Arakawa, T. et al., "Natural Motion Generation of Biped Locomotion Robot Using Hierarchical Trajectory Generation Method Consisting of GA, EP Layers," Proceedings of the 1997 IEEE International Conference on Robotics and Automation, Albuquerque, NM., pp. 375-379.
Au, S.K. et al., "Powered Ankle-Foot Prosthesis Improves Walking Metabolic Economy," *IEEE Transactions on Robotics*, 25(1): 51-66 (2009).
Au, S.K. et al., "Powered Ankle-Foot Prosthesis for the Improvement of Amputee Ambulation," paper presented at the Proceedings of the $29^{th}$ Annual International Conference of the IEEE EMBS Cité Internationale, Lyon, France, (Aug. 2007).
Au, S. et al., "Powered Ankle-Foot Prosthesis to Assist Level-Ground and Stair-Descent Gaits," *Neural Networks*, 21: 654-666 (2008).
Barth, D.G. et al., "Gait Analysis and Energy Cost of Below-Knee Amputees Wearing Six Different Prosthetic Feet," *JPO*, 4(2): 63 (1992).
Bateni, H. et al., "Kinematic and Kinetic Variations of Below-Knee Amputee Gait," *JPO*, 14(1):1-12 (2002).
Baten, Chris T.M. et al., "Inertial Sensing in Ambulatory Back Load Estimation," paper presented at the $18^{th}$ Annual International Conference of the IEEE Engineering in Medicine and Biology Society, Amsterdam, 1996, pp. 497-498.
Blaya, J. et al., "Active Ankle Foot Orthoses (AAFO)," Artificial Intelligence Laboratory, Massachusetts Institute of Technology, Cambridge, MA, pp. 275-277.
Blaya, J.A. et al., "Adaptive Control of a Variable-Impedance Ankle-Foot Orthosis to Assist Drop-Foot Gait," IEEE Transactions on Neural Systems and Rehabilitation Engineering, 12(1): 24-31 (2004).
Blaya, J.A. et al., "Force-Controllable Ankle-Foot Orthosis (AFO) to Assist Drop Foot Gait," Massachusetts Institute of Technology, Feb. 2003, pp. 1-96.
Blickhan, R., "The Spring-Mass Model for Running and Hopping," *J. Biomechanics*, 22(11/12): 1217-1227 (1989).

(56) References Cited

OTHER PUBLICATIONS

Bortz, J.E. "A New Mathematical Formulation for Strapdown Inertial Navigation," *IEEE Transactions on Aerospace and Electronic Systems*, AES-7(1): 61-66 (1971).

Bouten, C.V. et al., "Assessment of Energy Expenditure for Physical Activity Using a Triaxial Accelerometer," *Medicine and Science in Sports and Exercise*, pp. 1516-1523.

Brockway, J.M., "Derivation of Formulae Used to Calculate Energy Expenditure in Man," *Human Nutrition: Clinical Nutrition* (1987), 41C, pp. 463-471.

Brown, T. Graham, "On the Nature of the Fundamental Activity of the Nervous Centres; Together with an Analysis of the Conditioning of Rhythmic Activity in Progression, and a Theory of the Evolution of Function in the Nervous System," pp. 24-46.

AJG The American Journal of Gastroenterology, "Symptoms Diagnosis," 105(4): 1-875 (2010).

Chu, A. et al., "On the Biomimetic Design of the Berkeley Lower Extremity Exoskeleton," paper presented at the Proceedings of the 2005 IEEE International Conference on Robotics and Automation, Barcelona, Spain, (Apr. 2005) pp. 4556-4363.

American Journal of Physical Medicine & Rehabilitation, 71(5): 1-278 (1992).

Colgate, James Edward, "The Control of Dynamically Interacting Systems," Massachusetts Institute of Technology, Aug. 1988, pp. 1-15.

Collins, S.H. et al., "Controlled Energy Storage and Return Prosthesis Reduces Metabolic Cost of Walking," ISB XXth Congress—ASB $29^{th}$ Annual Meeting, Jul. 31-Aug. 5, Cleveland, Ohio, pp. 804.

Collins, S.H. et al., "Efficient Bipedal Robots Based on Passive-Dynamic Walkers," Feb. 11, 2005, pp. 1-8.

Crago, P.E. et al., "New Control Strategies for Neuroprosthetic Systems," *Journal of Rehabilitation Research and Development*, vol. 33, No. 2, Apr. 1996, pp. 158-172.

Daley, M.A. et al., "Running Stability is Enhanced by a Proximo-Distal Gradient in Joint Neuromechanical Control," *The Journal of Experimental Biology*, vol. 210, pp. 383-394 (Feb. 2007).

Dapena, J. et al., "A Three-Dimensional Analysis of Angular Momentum in the Hammer Throw," Biomechanics Laboratory, Indiana University, IN, *Medicine and Science in Sports and Exercise*, vol. 21, No. 2, pp. 206-220 (1988).

Dietz, V. "Proprioception and Locomotor Disorders," *Nature Reviews*, vol. 3, pp. 781-790 (Oct. 2002).

Dietz, V. "Spinal Cord Pattern Generators for Locomotion," *Clinical Neurophysiology*, vol. 114, Issue 8, pp. 1-12 (Aug. 2003).

Doerschuk, P.C. et al., "Upper Extremity Limb Function Discrimination Using EMG Signal Analysis," *IEEE Transactions on Biomedical Engineering*, vol. BME-30, No. 1, Jan. 1983, pp. 18-28.

Doke, J. et al., "Mechanics and Energetics of Swinging the Human Leg," *The Journal of Experimental Biology*, vol. 208, pp. 439-445 (2005).

Dollar, A.M. et al., "Lower Extremity Exoskeletons and Active Orthoses: Challenges and State-of-the-Art," *IEEE Transactions on Robotics*, vol. 24, No. 1, Feb. 2008, pp. 1-15.

Donelan, J.M. et al., "Force Regulation of Ankle Extensor Muscle Activity in Freely Walking Cats," *Journal of Neurophysiology*, vol. 101, pp. 360-371 (2009).

Donelan, J.M. et al., "Mechanical work for Step-to-Step Transitions is a Major Determinant of the Metabolic Cost of Human Walking," *The Journal of Experimental Biology*, vol. 205, pp. 3717-3727 (2002).

Donelan, J.M. et al., "Simultaneous Positive and Negative External Mechanical Work in Human Walking," *Journal of Biomechanics*, vol. 35, 2002, pp. 117-124 (2002).

HemiHelp, "Ankle & Foot Splints or Orthoses," (AFOs).

HemiHelp, "Foot & Ankle Splints or Orthoses," pp. 1-5.

Drake, C., "Foot & Ankle Splints or Orthoses," pp. 1-3.

Eilenberg, M.F. "A Neuromuscular-Model Based Control Strategy for Powered Ankle-Foot Prostheses," Massachusetts Institute of Technology, pp. 1-90.

Ekeberg, Ö et al., "Computer Simulation of Stepping in the Hind Legs of the Cat: An Examination of Mechanisms Regulating the Stance-to-Swing Transition," *J. Neurophysical*, vol. 94, pp. 4256-4268 (2005).

Ekeberg, Ö et al., "Simulations of Neuromuscular Control in Lamprey Swimming," The Royal Society, *Phil. Trans. R. Soc. Land*, vol. 354, pp. 895-902 (1999).

Endo, K. et al., "A Quasi-Passive Model of Human Leg Function in Level-Ground Walking," Proceedings of the 2006 IEEE/RSJ International Conference on Intelligent Robots and Systems, Oct. 9-15, 2006, Beijing, China, pp. 4935-4939.

Eppinger, S.D. et al., "Three Dynamic Problems in Robot Force Control," *IEEE Transactions on Robotics and Automation*, vol. 8, No. 6, pp. 772-778 (Dec. 1992).

Esquenazi, A. et al., "Rehabilitation After Amputation," vol. 91, No. 1, pp. 1-22 (Jan. 2001).

Farley, C.T. et al., "Energetics of Walking and Running: Insights From Simulated Reduced-Gravity Experiments," Harvard University, pp. 2709-2712.

Farry, K.A. et al., "Myoelectric Teleoperation of a Complex Robotic Hand," *IEEE Transactions on Robotics and Automation*, vol. 12, No. 5, pp. 775-778 (Oct. 1996).

Featherstone, R., "Robot Dynamics Algorithms," Edinburgh University, pp. 1-173.

Fite, K. et al., "Design and Control of an Electrically Powered Knee Prosthesis," Proceedings of the 2007 IEEE $10^{th}$ International Conference on Rehabilitation Robotics, Jun. 12-15, The Netherlands, pp. 902-905.

Flowers, W.C., "A Man-Interactive Simulator System for Above-Knee Prosthetics Studies," MIT, pp. 1-94.

Fod, A. et al., "Automated Derivation of Primitives for Movement Classification," *Autonomous Robots*, vol. 12, No. 1, pp. 39-54 (Jan. 2002).

Frigon, A. et al., "Experiments and Models of Sensorimotor Interactions During Locomotion," *Biological Cybernetics*, vol. 95, pp. 606-627 (2006).

Fujita et al., "Joint Angle Control with Command Filter for Human Ankle Movement Using Functional Electrical Stimulation," IEEE Ninth Annual Conference of the Engineering in Medicine and Biology Society.

Fukuda, O. et al., "A Human-Assisting Manipulator Teleoperated by EMG Signals and Arm Motions," *IEEE Transactions on Robotics and Automation*, vol. 19, No. 2, pp. 210-222 (Apr. 2003).

Gates, D.H. Thesis: "Characterizing Ankle Function During Stair Ascent, Descent, and Level Walking for Ankle Prosthesis and Orthosis Design," Boston University, pp. 1-84.

Gerritsen, K.G.M. et al., "Direct Dynamics Simulation of the Impact Phase in Heel-Toe Running," *J. Biomechanics*, vol. 28, No. 6, pp. 661-668 (1995).

Geyer, H. et al., "A Muscle-Reflex Model that Encodes Principles of Legged Mechanics Produces Human Walking Dynamics and Muscle Activities," IEEE Transactions on Neural Systems and Rehabilitation Engineering, vol. X, No. X, pp. 1-10.

Geyer, H. et al., "Compliant Leg Behavior Explains Basic Dynamics of Walking and Running," *Proc. R. Soc. B*, vol. 273, pp. 2861-2867 (2006).

Geyer, H. et al., "Positive Force Feedback in Bouncing Gaits?," *Proc. R. Soc. Lond, B*, vol. 270, pp. 2173-2183 (2003).

Ghigliazza, R.M. et al., "A Simply Stabilized Running Model," University of Pennsylvania, *SIAM Journal on Applied Dynamical Systems*, vol. 2, Issue 2, pp. 187-218 (May 8, 2004).

Giszter, S., et al., "Convergent Force Fields Organized in the Frog's Spinal Cord," *Journal of Neuroscience*, 13(2): 467-491 (1993).

Godha, S. et al., "Integrated GPS/INS System for Pedestrian Navigation in a Signal Degraded Environment," University of Calgary, Canada, pp. 1-14.

Goswami, A., "Postural Stability of Biped Robots and the Foot-Rotation Indicator (FRI) Point," *The International Journal of Robotics Research*, vol. 18, No. 6, pp. 523-533 (Jun. 1999).

Goswami, A. et al., "Rate of Change of Angular Momentum and Balance Maintenance of Biped Robots," Proceedings of the 2004 IEEE International Conference on Robotics and Automation, New Orleans, LA, Apr. 2004, pp. 3785-3790.

(56) References Cited

OTHER PUBLICATIONS

Graupe, D. et al., "A Microprocessor System for Multifunctional Control of Upper-Limb Prostheses via Myoelectric Signal Identification," *IEEE Transactions on Automatic Control*, vol. 23, No. 4, pp. 538-544 (Aug. 1978).
Gregoire, L. et al., "Role of Mono- and Biarticular Muscles in Explosive Movements," *International Journal of Sports Medicine*, vol. 5, No. 6, pp. 299-352 (Dec. 1984).
Grillner, S. and Zangger, P., "On the Central Generation of Locomotion in the Low Spinal Cat," *Experimental Brain Research*, 34: 241-261 (1979).
Grimes, D.L., "An Active Multi-Mode Above-Knee Prosthesis Controller," unpublished doctoral dissertation, Massachusetts Institute of Technology (1979).
Gunther, M. et al., "Human Leg Design: Optimal Axial Alignment Under Constraints," *J. Math. Biol.*, 48: 623-646 (2004).
Günther, M., and Ruder, H., "Synthesis of Two-Dimensional Human Walking: a test of the λ-model," *Biol. Cybern.*, 89: 89-106 (2003).
Gu, W.J., "The Regulation of Angular Momentum During Human Walking," unpublished doctoral dissertation, Massachusetts Institute of Technology (2003).
Brady, M. et al., "Robot Motion: Planning and Control," The MIT Press, Cambridge (1982).
Hansen, A.H., et al., "The Human Ankle During Walking: Implications for Design of Biomimetic Ankle Prostheses," *Journal of Biomechanics*, 37: 1467-1474 (2004).
Hayes, W.C., et al., "Leg Motion Analysis During Gait by Multiaxial Accelerometry: Theoretical Foundations and Preliminary Validations," *Journal of Biomechanical Engineering*, 105: 283-289 (1983).
Heglund, N. et al., "A Simple Design for a Force-Plate to Measure Ground Reaction Forces," *J. Exp. Biol.*, 93: 333-338 (1981).
Herr, H.M. et al., "A Model of Scale Effects in mammalian Quadrupedal Running," *The Journal of Experimental Biology*, 205: 959-967 (2002).
Herr, H.M., and Popovic, M., "Angular Momentum in Human Walking," *The Journal of Experimental Biology*, 211: 467-481 (2008).
Herr, H.M., and McMahon, T.A., "A Trotting Horse Model," *The International Journal of Robotics Research*, 19: 566-581 (2000).
Herr, H.M., and Wilkenfeld, A., "User-adaptive Control of A Magnetorheological Prosthetic Knee," *Industrial Robot: An International Journal*, 30(1): 42-55 (2003).
Heyn, A., et al., "The Kinematics of the Swing Phase Obtained From Accelerometer and Gyroscope Measurements," paper presented at the 18th Annual International Conference of the IEEE Engineering in Medicine and Biology Society, Amsterdam (1996).
Hill, A.V., "The Heat of Shortening and the Dynamic Constants of Muscle," *Proc. R. Soc. Lond.*, 126: 136-195 (1938).
Hirai, K., et al., "The Development of Honda Humanoid Robot," paper presented at the 1998 IEEE International Conference on Robotics & Automation (1998).
Hitt, J.K., et al., "The Sparky (Spring Ankle with Regenerative Kinetics) Project: Design and Analysis of a Robotic Transtibial Prosthesis with Regenerative Kinetics," Proceedings of the ASME International Design Engineering Technical Conferences and Computers and Information in Engineering Conference, Las Vegas, Nevada (2007).
Hofbaur, M.W., et al., "Hybrid Diagnosis with Unknown Behavioral Modes," Proceedings of the 13th International Workshop on Principles of Diagnosis (DX02) (2002).
Hofbaur, M.W., and Williams, B.C., "Mode Estimation of Probabilistic Hybrid Systems," MIT Space Systems and Artificial Intelligence Laboratories and Graz University of Technology, Department of Automatic Control.
Hof, A.L., et al., "Calf Muscle Moment, Work and Efficiency in Level Walking: Role of Series Elasticity," *J. Biochem.*, 16: 523-537 (1983).
Hofmann, A., et al., "A Sliding Controller for Bipedal Balancing Using Integrated Movement of Contact and Non-Contact Limbs," Proceedings of the 2004 IEEE/RSJ International Conference on Intelligence Robots and Systems, Japan (2004).
Hofmann, A.G., "Robust Execution of Bipedal Walking Tasks From Biomechanical Principles," unpublished doctoral dissertation for Massachusetts Institute of Technology (2006).
Hogan, N., "A Review of the Methods of Processing EMG for Use As a Proportional Control Signal," *Biomedical Engineering*, 11(3): 81-86 (1976).
Hogan, N., "Impedance Control—An Approach to Manipulation," unpublished doctoral dissertation for Department of Mechanical Engineering and Laboratory of Manufacturing and Productivity, Massachusetts Institute of Technology, pp. 304-313.
Hogan, N., and Buerger, S.P., "Impedance and Interaction Control, Robots and Automation Handbook."
Hogan, N., "Impedance Control: An Approach to Manipulation, Part III—Applications," *Journal of Dynamic Systems, Measurement, and Control*, 107: 17-24 (1985).
Hogan, N., "Impedance Control: An Approach to Manipulation: Part II—Implementation, " *Journal of Dynamic Systems, Measurement, and Control*,107: 8-16 (1985).
Hogan, N., "Impedance Control: An Approach to Manipulation: Part I—Theory," *Journal of Dynamic Systems, Measurement, and Control*, 107: 1-7 (1985).
Hollander, K.W. et al., "Adjustable Robotic Tendon using a 'Jack Spring'™," Proceedings of the 2005 IEEE, 9th International Conference on Rehabilitation Robotics, Jun. 28-Jul. 1, 2005, Chicago, IL, USA, pp. 113-118.
Howard, R.D., Thesis: "Joint and Actuator Design for Enhanced Stability in Robotic Force Control," Submitted to the Dept. of Aeronautics and Astronautics on Aug. 8, 1990 in partial fulfillment of the requirements for the degree of Doctor of Philosophy.
Huang, H.-P. et al., "Development of a Myoelectric Discrimination System for a Multi-Degree Prosthetic Hand," Proceedings of the 1999 IEEE, International Conference on Robotics & Automation, Detroit, Michigan, (1999).
Huang, Q. et al., "Planning Walking Patterns for a Biped Robot," *IEEE Transactions on Robotics and Automation*,17(3): 280-289 (Jun. 2001).
Hultborn, H., "Spinal reflexes, mechanisms and concepts: From Eccles to Lundberg and beyond," *Progress in Neurobiology*,78: 215-232 (2006).
Ijspeert, A.J., "Central pattern generators for locomotion control in animals and robots: a review," *Preprint of Neural Networks*, vol. 21, No. 4, pp. 642-653 (2008).
Ijspeert, A.J. et al., "From swimming to walking with a salamander robot driven by a spinal cord model," pp. 1-5.
Ivashko, D.G. et al., "Modeling the spinal cord neural circuitry controlling cat hindlimb movement during locomotion," *Neurocomputing*, 52-54, pp. 621-629 (2003).
International Search Report and Written Opinion for International Application No. PCT/US2009/055600, Mailed: Apr. 29, 2010.
International Preliminary Report on Patentability for International Application No. PCT/US2010/047279; Mailed: Mar. 15, 2012.
International Search Report and Written Opinion for International Application No. PCT/US2010/047279; Mailed: Jan. 19, 2011.
International Search Report and Written Opinion for International Application No. PCT/US2011/031105, Mailed: Oct. 11, 2011.
Johansson, J.L. et al., "A Clinical Comparison of Variable-Damping and Mechanically Passive Prosthetic Knee Devices," Variable-Damping vs. Mechanically Passive Prosthetic Knees, Aug. 2005.
Johnson, C.T. et al., "Experimental Identification of Friction and Its Compensation in Precise, Position Controlled Mechanisms," *IEEE Transactions on Industry Applications*, vol. 28, No. 6, pp. 1392-1398 (Nov./Dec. 1992).
Jonic, S. et al., "Three Machine Learning Techniques for Automatic Determination of Rules to Control Locomotion," *IEEE Transactions on Biomedical Engineering*, vol. 46, No. 3, pp. 300-310 (Mar. 1999).
Kadaba, M.P. et al., "Measurement of Lower Extremity Kinematics During Level Walking," *Journal of Orthopedic Research*, pp. 383-392, 1990.
Kadaba, M.P. et al., "Repeatability of Kinematic, Kinetic, and Electromyographic Data in Normal Adult Gait," *Journal of Orthopedic Research*, pp. 849-860, 1989.

(56) References Cited

OTHER PUBLICATIONS

Kajita, S. et al., "A Hop towards Running Humanoid Biped," Proceedings of the 2004 IEEE International Conference on Robotics & Automation, pp. 629-635, 2004.

Kajita, S. et al., "Biped Walking on a Low Friction Floor," Proceedings of the 2004 IEEE/RSJ International Conference on Intelligent Robots & Systems, pp. 3546-3552, Sep. 28-Oct. 2, 2004, Sendai, Japan.

Kajita, S. et al., "Resolved Momentum Control: Humanoid Motion Planning based on the Linear and Angular Momentum," Proceedings of the 2003 IEEE/RSJ International Conference on Intelligent Robots & Systems, pp. 1644-1650 (2003).

Kaneko, K. et al., "Humanoid Robot HRP-2," Proceedings of the 2004 IEEE International Conference on Robotics & Automation, pp. 1083-1090 (Apr. 2004).

Kapti, A.O. et al., "Design and control of an active artificial knee joint," *Mechanism and Machine Theory*, vol. 41, pp. 1477-1485 (2006).

Katic, D. et al., "Survey of Intelligent Control Techniques for Humanoid Robots," *Journal of Intelligent and Robotic Systems*, vol. 37, pp. 117-141 (2003).

Kerrigan, D.C. et al., "A refined view of the determinants of gait: Significance of heel," *Archives of Physical Medicine and Rehabilitation*, vol. 81, Issue 8, pp. 1077-1080 (Aug. 2000).

Kerrigan, D.C. et al., "Quantification of pelvic rotation as a determinant of gait," Archives of Physical Medicine and Rehabilitation, vol. 82, Issue 2, pp. 217-220 (Feb. 2001).

Khatib, O. et al., "Coordination and Decentralized Cooperation of Multiple Mobile Manipulators," *Journal of Robotic Systems*, 13(11): 755-764 (1996).

Khatib, O. et al., "Whole-Body Dynamic Behavior and Control of Human-Like Robots," *International Journal of Humanoid Robotics*, vol. 1, No. 1, pp. 29-43 (2004).

Kidder, S.M. et al., "A System for the Analysis of Foot and Ankle Kinematics During Gait," *IEEE Transactions on Rehabilitation Engineering*, vol. 4, No. 1, pp. 25-32 (Mar. 1996).

Kim, J.-H. et al., "Realization of dynamic walking for the humanoid robot platform KHR-1," *Advanced Robotics*, vol. 18, No. 7, pp. 749-768 (2004).

Kirkwood, C.A. et al., "Automatic detection of gait events: a case study using inductive learning techniques," *J. Biomed. Eng.*, vol. 11, pp. 511-516 (Nov. 1989).

Kitayama, I. et al., "A Microcomputer Controlled Intelligent A/K Prosthesis—Fundamental Development," Proceedings, Seventh World Congress of ISPO, Jun. 28-Jul. 3, 1992, Chicago, Illinois, USA, 25 pages.

Klute, G.K. et al., "Artificial Muscles: Actuators for Lower Limb Prostheses," Abstract in: Proceedings of the $2^{nd}$ Annual Meeting of the VA Rehabilitation Research and Development Service, Washington, D.C., Feb. 20-22, 2000, p. 107.

Klute, G.K. et al., "Artificial Muscles: Actuators for Biorobotic Systems," *The International Journal of Robotics Research*, vol. 21, pp. 295-309 (2002).

Klute, G.K. et al., "Artificial Muscles: Biomechanical Design Properties for Prosthetic Lower Limbs," Chicago 2000 World Congress on Medical Physics and Biomedical Engineering, Chicago on Jul. 24-28, 2000, 4 pages.

Klute, G.K. et al, "Intelligent transtibial prostheses with muscle-like actuators," 2002 American Physiological Society Intersociety Meeting: The Power of Comparative Physiology: Evolution, Integration, and Applied, 1 page abstract.

Klute, G.K. et al., "Lower Limb Prostheses Powered by Muscle-like Pneumatic Actuators," Submitted to Oleodinamica e Pneumatica, Publisher Tecniche Nuove, Milano, Italy, Mar. 15, 2000, pp. 1-6.

Klute, G.K. et al., "McKibben Artificial Muscles: Pneumatic Actuators with Biomechanical Intelligence," IEEE/ASME 1999 International Conference on Advanced Intelligent Mechatronics (AIM '99), Atlanta, GA, Sep. 19-22, 1999, pp. 221-226.

Klute, G.K. et al., "Mechanical properties of prosthetic limbs: Adapting to the patient," *Journal of Rehabilitation Research and Development*, vol. 38, No. 3, pp. 299-307 (May/Jun. 2001).

Klute, G.K. et al., "Muscle-like Pneumatic Actuators for Below-knee Prostheses," "Actuator 2000: $7^{th}$ International Conference on New Actuators," Bremen, Germany on Jun. 19-21, 2000, pp. 289-292.

Klute, G.K. et al., "Powering Lower Limb Prosthetics with Muscle-like Actuators," Abstract in: Proceedings of the $1^{st}$ Annual Meeting of the VA Rehabilitation Research and Development Service, "Enabling Veterans: Meeting the Challenge of Rehabilitation in the Next Millenium," Washington, D.C., Oct. 1-3, 1998, p. 52.

Klute, G.K. et al., "Variable Stiffness Prosthesis for Transtibial Amputees," 2 pages.

Koganezawa, K. et al., *Biomedical Engineering 1987*, 2.3: Control Aspects of Artificial Leg, pp. 71-85.

Kondak, K. et al., "Control and Online Computation of Stable Movement for Biped Robots," Proceedings of the 2003 IEEE/RSJ, Int'l Conference on Intelligent Robots and Systems, Las Vegas, Nevada, Oct. 2003, pp. 874-879.

Kostov, A. et al., "Machine Learning in Control of Functional Electrical Stimulation Systems for Locomotion," *IEEE Transactions on Biomedical Engineering*, vol. 42, No. 6, pp. 541-551 (Jun. 1995).

Kuo, A.D., "A Simple Model of Bipedal Walking Predicts the Preferred Speed-Step Length Relationship," *Transactions of the ASME*, vol. 123, pp. 264-269 (Jun. 2001).

Kuo, A.D., "Energetics of Actively Powered Locomotion Using the Simplest Walking Model," *Journal of Biomechanical Engineering*, vol. 124, pp. 113-120 (Feb. 2002).

Lafortune, M.A., "Three-Dimensional Acceleration of the Tibia During Walking and Running," *J. Biomechanics*, vol. 24, No. 10, pp. 877-886 (1991).

LeBlanc, M.K. et al., "Generation and Transfer of Angular Momentum in the Javelin Throw," American Society of Biomechanics, Presented at the $20^{th}$ Annual Meeting of the American Society of Biomechanics, Atlanta, Georgia, Oct. 17-19, 1996, 4 pages.

Light, L.H. et al., "Skeletal Transients on Heel Strike in Normal Walking with Different Footwear," J. Biomechanics, vol. 13, pp. 477-480 (1980).

Li, C. et al., "Research and Development of the Intelligently-Controlled Prosthetic Ankle Joint," Proceedings of the 2006 IEEE International Conference on Mechatronics and Automation, Jun. 25-28, 2006, Luoyana, China, pp. 1114-1119.

Liu, X. et al., "Development of a Lower Extremity Exoskeleton for Human Performance Enhancement," Proceedings of 2004 IEEE/RSJ International Conference on Intelligent Robots and Systems, Sep. 28-Oct. 2, 2004, Sendai, Japan, 3889-3894.

Lloyd, R. et al., "Kinetic changes associated with load carriage using two rucksack designs," *Ergonomics*, vol. 43, No. 9, pp. 1331-1341 (2000).

Luinge, H.J., *Inertial Sensing of Human Movement*, Twente University Press, Enschede, the Netherlands, 80 pages (Feb. 15, 1973).

Lundberg, A., "Reflex control of stepping," The Norwegian Academy of Science and Letters, The Nansen Memorial Lecture, Oct. 10, 1968, 40 pages.

Macfarlane, P.A. et al., "Gait Comparisons for Below-Knee Amputees Using a Flex-Foot(TM) Versus a Conventional Prosthetic Foot," JPO 1991, vol. 3, No. 4, pp. 150, htt://www.oandp.org/jpo/library/printArticle.asp?printArticleId=1991_04_150, Retrieved on: Feb. 9, 2012, 10 pages.

Maganaris, C.N., "Force-length characteristics of in vivo human skeletal muscle," *Acta Physiol Scand*, 172: 279-285 (2001).

Maganaris, C.N., "Force-Length Characteristics of the In Vivo Human Gastroenemius Muscle," *Clinical Anatomy*, 16: 215-223 (2003).

Martens, W.L. J., "Exploring the Information Content and Some Applications of Body Mounted Piezo-Resistive Accelerometers," 3 pages.

Maufroy, C. et al., "Towards a general neural controller for quadrupedal locomotion," Neural Networks, 21: 667-681 (2008).

Mayagoitia, R.E. et al., "Accelerometer and rate gyroscope measurement of kinematics: an inexpensive alternative to optical motion analysis systems," *Journal of Biomechanics*, 35: 537-542 (2002).

(56) References Cited

OTHER PUBLICATIONS

McFadyen, B.J. et al., "An Integrated Biomechanical Analysis of Normal Stair Ascent and Descent," J. Biomechanics, vol. 21, No. 9, pp. 733-744 (1988).

McGeer, T., "Passive Dynamic Walking," The International Journal of Robotics Research, 9, pp. 62-88 (1990).

McGeer, T., Chapter 4: "Principles of Walking and Running," *Advances in Comparative and Environmental Physiology*, vol. 11, pp. 113-139 (1992).

McIntosh, A.S. et al., "Gait dynamics on an inclined walkway," Journal of Biomechanics, vol. 39, Issue 13, pp. 2491-2502 (2006).

McMahon, T.A. et al., "Groucho Running," pp. 2326-2337 (1987).

McMahon, T.A. et al., "The Mechanics of Running: How Does Stiffness Couple with Speed?" J. Biomechanics, vol. 23, Suppl. 1, pp. 65-78 (1990).

Minassian, K. et al., "Human lumbar cord circuitries can be activated by extrinsic tonic input to generate locomotor-like activity," Human Movement Science, 26: 275-295 (2007).

Mochon, S. et al., "Ballistic Walking," *J. Biomechanics*, vol. 13, pp. 49-57 (1980).

Molen, N.H., "Energy/Speed Relation of Below-Knee Amputees Walking on a Motor-Driven Treadmill," Physiol, 31: 173-185 (1973).

Morris, J.R.W., "Accelerometry—A Technique for the Measurement of Human Body Movements," J. Biomechanics, vol. 6, pp. 729-736 (1973).

Muraoka, T. et al., "Muscle fiber and tendon length changes in the human vastus lateralis during show pedaling," J. Appl. Physiol., 91: 2035-2040 (2001).

Nakagawa, A., "Intelligent Knee Mechanism and the Possibility to Apply the Principle to the Other Joints," paper presented at the Proceedings of the 20$^{th}$ Annual International Conference of the IEEE Engineering in Medicine and Biology Society, 20(5): 2282-2287 (1998).

Neal, R. M. et al., "A View of the EM Algorithm That Justifies Incremental, Sparse, and Other Variants," pp. 1-14.

Ng, S.K. et al., "Fuzzy Model Identification for Classification of Gait Events in Paraplegics," IEEE Transactions on Fuzzy Systems, 5(4) (1997).

Nielsen, D.H. et al., "Comparison of Energy Cost and Gait Efficiency during Ambulation in Below-Knee Ampuees Using Different Prosthetic Feet," *JPO*, 1:24-31, http://www.oandp.org/jpo/library/1989_01_024.asd, Retrieved on: Feb. 7, 2012.

Oda, T. et al. "In Vivo Length-Force Relationships on Muscle Fiber and Muscle Tendon Complex in the Tibialis Anterior Muscle," *International Journal of Sport and Health Sciences*, 3:245-252 (2005).

Ogihara, N., and Yamazaki, N., "Generation of Human Bipedal Locomotion by a Bio-Mimetic Neuro-Musculo-Skeletal Model," *Biol. Cybern.*, 84: 1-11 (2001).

Palmer, M.L., "Sagittal Plane Characterization of Normal Human Ankle Function Across a Range of Walking Gait Speeds," Unpublished master's thesis, Massachusetts Institute of Technology, Massachusetts (2002).

Paluska, D., and Herr, H., "Series Elasticity and Actuator Power Output," paper presented at the Proceedings of the 2006 IEEE International Conference on Robotics and Automation (2006).

Paluska, D., and Herr H., "The Effect of Series Elasticity on Actuator Power and Work Output: Implications for Robotic and Prosthetic Joint Design," Robotics and Autonomous Systems, 54:667-673 (2006).

Pang, M.Y.C. and Yang, J.F., "The Initiation of the Swing Phase in Human Infact Stepping: Importance of Hip Position and Leg Loading," Journal of Physiology, 528(2):389-404 (2000).

Dubowsky, S., "Transactions of the ASME," *Journal of Mechanisms, Transmissions, and Automation in Design*, 106(1): 102-107 (1984).

Paul, C., et al., "Development of a Human Neuro-Musculo-Skeletal Model for Investigation of Spinal Cord Injury," *Biol. Cybern.*, 93:153-170 (2005).

Pearson, K., et al., "Assessing Sensory Function in Locomotor Systems Using neurp-mechanical Simulations," *Trends in Neurosciences*, 29(11): 626-631 (2006).

Pearson, K.G., "Generating the Walking Gait: Role of Sensory Feedback," Progress in Brain Research, 143:123-129 (2004).

Perry, J., et al., "Efficiency of Dynamic Elastic Response Prosthetic Feet," *Journal of Rehabilitation Research*, 30(1):137-143 (1993).

Davids, J.R., "Book Reviews" Journal of Pediatric Orthopedics, pp. 815.

Petrofsky, J.S.., et al., "Feedback Control System for Walking in Man," *Comput. Biol. Med.* 14(2):135-149 (1984).

Pfeffer, L.E., et al., "Experiments with a Dual-Armed, Cooperative, Flexible-Drivetrain Robot System," paper presented at the IEEE, Aerospace Robotics Laboratory, Department of Aeronautics and Astronautics, Stanford University (1993).

Popovic, M., et al., "Angular Momentum Primitives for Human Walking: Biomechanics and Control," paper presented at the Proceedings IEEE/RSJ International Conference on Intelligent Robots and Systems, 1685-1691 (2004).

Popovic, M., et al., "Angular Momentum Regulation During Human Walking: Biomechanics and Control," paper presented at the Proceedings IEEE International Conference on Robotics and Automation, 2405-2411 (2004).

Popovic, M., et al., "Conservation of Angular Momentum During Human Locomotion," *MIT Artificial Intelligence Laboratory*, pp. 231-232 (2002).

Popovic, D., et al., "Control Aspects of Active Above-Knee Prosthesis," *Int. J. Man-Machine Studies*, 35:751-767 (1991).

Popovic, D. and Sinkjacr, T., "Control of Movement for the Physically Disabled: Control for Rehabilitation Technology," (Springer Publisher) pp. 270-302.

Popovic, M.R., et al., "Gait Identification and Recognition Sensor," paper presented at the Proceedings of 6$^{th}$ Vienna International Workshop on Functional Electrostiumlation (Sep. 1998).

Popovic, M.B. and Herr, H., "Global Motion Control and Support Base Planning," pp. 1-8.

Popovic, M.B. and Herr, H., "Ground Reference Points in Legged Locomotion: Definitions, Biological Trajectories and Control Implications," *Mobile Robots Towards New Applications*, ISBN 3-86611-314-5, pp. 79-104 (2006).

Popovic, M.B., et al., "Zero Spin Angular Momentum Control: Definition and Applicability," pp. 1-16.

Pratt, G.A., "Legged Robots at MIT: What's New Since Raibert." Paper presented at the meeting of the IEEE, Robotics and Automation Magazine (Sep. 2000).

Pratt, G.A., "Low Impedance Walking Robots," *Integ. and Comp. Biol.*, 42: 174-181 (2002).

Pratt, J.E., et al., "The RoboKnee: An Exoskeleton for Enhancing Strength and Endurance During Walking." Paper presented at the Proceedings of the 2004 IEEE International Conference on Robotics & Automation, New Orleans, LA (Apr. 2004).

Pratt, G.A. and Williamson, M.M., "Series Elastic Actuators." Paper presented at the meeting of the IEEE, pp. 399-406 (1995).

Prochazka, A. and Yakovenko, S., "The Neuromechanical Tuning Hypothesis," *Progress in Brain Research*, 165: 257-267 (2007).

Prochazka, A., et al., "Sensory Control of Locomotion: Reflexes Versus Higher-Level Control," *Sensorimotor Control of Movement and Posture*, pp. 357-367 (2002).

Prochazka, A., et al., "Positive Force Feedback Control of Muscles," *The American Physiological Society*, pp. 3226-3236 (1997).

Raibert, M.H., "Legged Robots that Balance," MIT Press, Cambridge, MA, p. 89 (1985).

Rassier, D.E., et al., "Length Dependence of Active Force Production in Skeletal Muscle," *The American Physiological Society*, pp. 1445-1457 (1999).

Riener, R., et al., "Stair Ascent and Descent at Different Inclinations," *Gait and Posture*, 15: 32-44 (2002).

Rietman, J.S., et al., "Gait Analysis in Prosthetics: Opinions, Ideas and Conclusions," *Prosthetics and Orthotics International*, 26: 50-57 (2002).

Robinson, D.W., "Design and Analysis of Series Elasticity in Closed-Loop Actuator Force Control." Unpublished doctoral dissertation, Massachusetts Institute of Technology (2000).

(56) References Cited

OTHER PUBLICATIONS

Robinson, D.W., et al., "Series Elastic Actuator Development for a Biomimetic Walking Robot." Paper presented at the IEEE/ASME International Conf. on Adv. Intelligent Mechatronics (Sep. 19-22, 1999).

Rosen, J., et al., "A Myosignal-Based Powered Exoskeleton System," *IEEE Transaction on Systems, Man, and Cybernetics—Part A: Systems and Humans*, 31(3): 210-222 (2001).

Ruina, A., et al., "A Collisional Model of the Energetic Cost of Support Work Qualitatively Explains Leg Sequencing in Walking and Galloping, Pseudo-Elastic Leg Behavior in Running and the Walk-To-Run Transition," *J. of Theoretical Biology*, 237: 170-192 (2005).

Rybak, I.A., et al., "Modelling Spinal Circuitry Involved in Locomotor Pattern Generation: Insights from Deletions During Fictive Locomotion," *J. Physiol.*, 577(2): 617-639 (2006).

Rybak, I.A., et al., "Modelling Spinal Circuitry Involved in Locomotor Pattern Generation: Insights from the Effects of Afferent Stimulation," *J. Physiol.*, 577(2): 641-658 (2006).

Sanderson, D.J. and Martin. P.E., "Lower Extremity Kinematic and Kinetic Adaptations in Unilateral Below-Knee Amputees During Walking," *Gait & Posture*, 6(2): 126-136 (1997).

Sanger, T.D., "Human Arm Movements Described by a Low-Dimensional Superposition of Principal Components," *The J. of Neuroscience*, 20(3): 1066-1072 (2000).

Saranli, U., et al., "RHex: A Simple and Highly Mobile Hexapod Robot," *The International Journal of Robotics Research*, pp. 616-631 (2001).

Sarrigeorgidis, K. and Kyriakopoulos, K.J., "Motion Control of the N.T.U.A. Robotic Snake on a Planar Surface." Paper presented at the Proceedings of the 1998 IEEE International Conference on Robotics & Automation, Leuven, Belgium (May 1998).

Schaal, S. and Atkeson, C.G., "Constructive Incremental Learning from Only Local Information," *Neural Computation*, 10(8): 2047-2084 (1998).

Schaal, S., "Is Imitation Learning the Route to Humanoid Robots?", *Trends in Cognitive Sciences*, 3: 233-242 (1999).

Scott, S.H. and Winter, D.A., "Biomechanical Model of the Human Foot: Kinematics and Kinetics During the Stance Phase of Walking," *J. Biomechanics*, 26(9): 1091-1104 (1993).

Sentis, L. and Khatib, O., "Task-Oriented Control of Humanoid Robots Through Prioritization." Paper presented at the IEEE-RAS/RSJ International Conference on Humanoid Robots, pp. 1-16.

Seyfarth, A., et al., "A Movement Criterion for Running," *J. of Biomechanics*, 35: 649-655 (2002).

Seyfarth, A., et al., "Stable Operation of an Elastic Three-Segment Leg," *Biol. Cybern.*, 84: 365-382 (2001).

Seyfarth, A., et al., "Swing-Leg Retraction: A Simple Control Model for Stable Running," *The J. of Experimental Biology*, 206: 2547-2555 (2003).

Giszter et al., "Convergent Force Fields Organized in the Frog's Spinal Cord," *The Journal of Neuroscience*, Feb. 1993, pp. 467-491.

Sinkjaer, T., et al., "Major role for sensory feedback in soleus EMG activity in the stance phase of walking in man," *Journal of Physiology*, 523.3: 817-827 (2000).

Skinner, H.B., and Effeney, D.J., "Gait Analysis in Amputees," *American Journal of Physical Medicine*, 64(2): 82-89 (1985).

Smidt, G.L., et al., "An Automated Accelerometry System for Gait Analysis," *J. Biomechanics*,10: 367-375 (1977).

Srinivasan, M., "Energetics of Legged Locomotion: Why is Total Metabolic Cost Proportional to the Cost of Stance Work." ISB XXth Congress—ASB 29$^{th}$ Annual Meeting, Cleveland, OH (Jul. 31-Aug. 5.

Stepien, J., et al.. "Activity Levels Among Lower-Limb Amputees: Self-Report Versus Step Activity Monitor," *Arch. Phys. Med. Rehabil.*, 88: 896-900 (2007).

Sugano, S., et al., "Force Control of the Robot Finger Joint equipped with Mechanical Compliance Adjuster," Proceedings of the 1992 IEEE/RSJ International Conference on Intelligent Robots and Systems, Raleigh, NC (Jul. 1992).

Sugihara, T., et al., "Realtime Humanoid Motion Generation through ZMP Manipulation based on Inverted Pendulum Control," Proceedings of the 2002 IEEE International Conference on Robotics & Automation, Washington, DC (May 2002).

Sup, F., et al., "Design and Control of a Powered Transfemoral Prosthesis," *The International Journal of Robotics Research*, 27(2): 263-273 (2008).

Taga, G., "A model of the neuro-musculo-skeletal system for human locomotion," *Biol. Cybern.*, 73: 97-111 (1995).

Takayuki, F., et al., "Biped Locomotion using Multiple Link Virtual Inverted Pendulum Model," *T.IEE Japan*, 120-C (2): 208-214 (2000).

Thoroughman, K., and Shadmehr, R., "Learning of action through adaptive combination of motor primitives," *Nature*, 407: 742-747(2000).

Tomović, R., and McHee, R.B., "A Finite State Approach to the Synthesis of Bioengineering Control Systems," *IEEE Transactions on Human Factors in Electronics*, 7(2): 65-69 (1966).

Tong, K., and Granat, M., "A practical gait analysis system using gyroscopes," *Medical Engineering & Physics*, 21: 87-94 (1999).

Türker, K., "Electromyography: Some Methodological Problems and Issues," *Phys. Ther.*, 73: 698-710 (1993).

Van den Bogert, A. J., et al., "A Method for Inverse Dynamic Analysis Using Accelerometry," *J. Biochemechanics*, 29(7): 949-954 (1996).

Van den Bogert, A. J., "Exotendons for Assistance of Human Locomotion," Biomedical Engineering OnLine, BioMed Central, 2(17):1-8 (2003).

Veltink, P.H., et al., "The Feasibility of Posture and Movement Detection by Accelerometry," paper presented at the IEEE meeting (1993).

Vukobratovic, M., Juricic, D., "Contribution to the Synthesis of Biped Gait," paper presented at the IEEE Transactions on Bio-Medical Engineering, BME-16(1) (Jan. 1969).

Vukobratovic, M., and Stepanenko, J., :Mathematical Models of General Anthropomorphic Systems, Mathematical Biosciences, 17: 191-242 (1973).

Walsh, C.J., et al., "Biomimetic Design of an Under-Actuated Leg Exoskeleton for Load-Carrying Augmentation," Unpublished Master's thesis, Massachusetts Institute of Technology, Cambridge, MA (2006).

Waters, R.L., et al., "Energy Cost of Walking of Amputees: The Influence of Level of Amputation," *The Journal of Bone and Joint Surgery*, 58A(1): 42-46 (1976).

Wilkenfeld, A., and Herr, H., "An Auto-Adaptive External Knee Prosthesis," MIT Lab.

Wilkenfeld, A., "Biologically Inspired Autoadaptive Control of a Knee Prosthesis," unpublished doctoral dissertation, Massachusetts Institute of Technology, Cambridge, MA (2000).

Willemsen, A.Th.M., et al., "Automatic Stance-Swing Phase Detection from Accelerometer Data for Peroneal Nerve Stimulation," presented at the meeting of IEEE Transactions on Biomedical Engineering, 37(12):1201-1208 (1990).

Willemsen, A.Th.M., et al., "Real-Time Gait Assessment Utilizing a New Way of Accelerometry," *J. Biomechanics*, 23(8):859-863 (1990).

Williams, B.C., et al., "Mode Estimation of Model-Based Programs: Monitoring Systems with Complex Behavior," paper submitted to Massachusetts Institute of Technology, Cambridge, MA.

Williamson, M.M., "Series Elastic Actuators," A.I. Technical Report submitted to Massachusetts Institute of Technology, Cambridge, Massachusetts (Jan. 1995).

Winter, D.A., and Sienko, S.E., "Biomechanics of Below-Knee Amputee Gait," *J. Biomechanics*, 21(5):361-367 (1988).

Winter, D.A., "Energy Generation and Absorption at the Ankle and Knee during Fast, Natural, and Slow Cadences," *Clinical Orthopedics and Related Research*, 175: 147-154 (1983).

Winter, D.A., and Robertson, D.G.E., "Joint Torque and Energy Patterns in Normal Gait," Biol. Cybernetics, 29:137-142 (1978).

Wisse, M., "Essentials of Dynamic Walking: Analysis and Design of Two-legged Robots,".

(56) References Cited

OTHER PUBLICATIONS

Woodward, M.I. and Cunningham, J.L., "Skeletal Accelerations Measured During Different Exercises," *Proc. Instn. Mech. Engrs.*, 207: 79-85 (1993).

Wu, G. and Ladin, Z., "The Study of Kinematic Transients in Locomotion Using the Integrated Kinematic Sensor," *IEEE Transactions on Rehabilitation Engineering*, 4(3): 193-200 (1996).

Yakovenko, S., et al., "Contribution of Stretch Reflexes to Locomotor Control: A Modeling Study," *Biol. Cybern.*, 90: 146-155 (2004).

Yun, X., "Dynamic State Feedback Control of Constrained Robot Manipulators." Paper presented at the Proceedings of the 27$^{th}$ Conference on Decision and Control, Austin, TX (Dec. 1988).

Zlatnik, D., et al., "Finite-State Control of a Trans-Femoral (TF) Prosthesis," *IEEE Transactions on Control Systems Technology*, 10(3): 408-420 (2002).

Office Action dated Feb. 16, 2012, in U.S. Appl. No. 12/697,894.

Colborne, G.R., et al., "Analysis of mechanical and metabolic factors in the gait of congenital below knee amputees," *Am. J. Phys. Med. Rehabil.*, vol. 92, pp. 272-278, Oct. 1992.

Collins, S.H., et al., "A Bipedal Walking Robot with Efficient and Human-Like Gait," 2005 IEEE, Int'l Conference on Robotics and Automation, Barcelona, Spain, pp. 1983-1988, (Apr. 2005).

Eilenberg, et al., "Control of a Powered Ankle-Foot Prosthesis Based on a Neuromuscular Model," *IEEE Transactions on Neural Systems & Rehabilitation Eng.*, vol. 18(2):164-173 (2010).

Hogan, N., and Buerger, S.P., "Impedance and Interaction Control, Robots and Automation Handbook, Chapter 19, © 2005 by CRC Press LLC, 24 pgs."

Holgate, M.A., et al., "The SPARKy (Spring Ankle with Regenerative Kinetics) Project: Choosing a DC Motor Based Actuation Method," Proceedings of the 2nd Biennial IEEE-EMBS International Conf. on Biomedical Robotics and Biomechatronics, Scottsdale, AZ, pp. 163-168, Oct. 19-22, 2008.

Supplementary European Search Report Application No. 10736533.0 dated Aug. 16, 2013.

Supplementary European Search Report Application No. 10736550.0 dated Aug. 1, 2013.

Non-Final Office Action U.S. Appl. No. 13/959,495 dated Aug. 27, 2014.

* cited by examiner

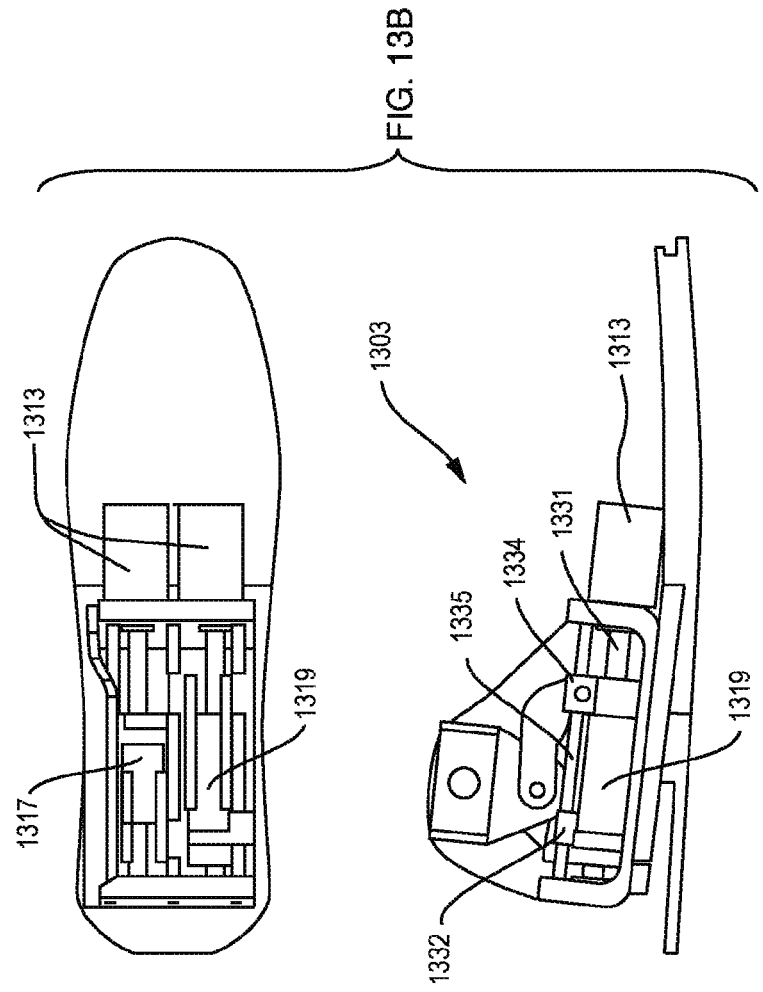
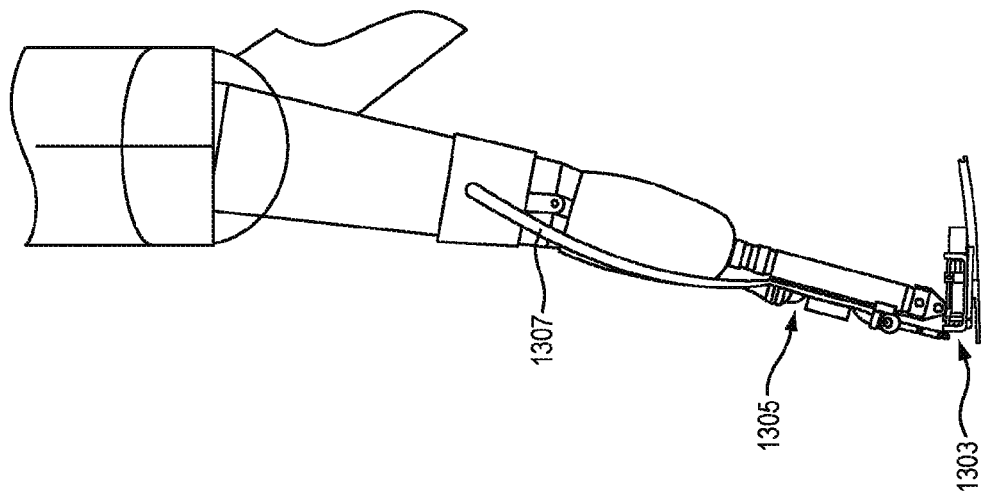

ARTIFICIAL JOINTS USING AGONIST-ANTAGONIST ACTUATORS

RELATED APPLICATIONS

This application is a continuation of U.S. patent application Ser. No. 11/642,993, filed Dec. 19, 2006, now abandoned, which claims the benefit of U.S. Prov. Pat. App. Ser. No. 60/751,680, filed on Dec. 19, 2005, now expired, the entire disclosures of which are incorporated by reference herein in their entirety.

This application is also a continuation in part of U.S. patent application Ser. No. 11/395,448 entitled "Artificial human limbs and joints employing actuators, springs, and Variable-Damper Elements" filed on Mar. 31, 2006 by Hugh M. Herr, Daniel Joseph Paluska, and Peter Dilworth. Application Ser. No. 11/395,448 claims the benefit of the filing date of U.S. Provisional Patent Application Ser. No. 60/666,876 filed on Mar. 31, 2005 and the benefit of the filing date of U.S. Provisional Patent Application Ser. No. 60/704,517 filed on Aug. 1, 2005.

This application is also a continuation in part of U.S. patent application Ser. No. 11/499,853 entitled "Biomimetic motion and balance controllers for use in prosthetics, orthotics and robotics" filed on Aug. 4, 2006 by Hugh M. Herr, Andreas G. Hofmann, and Marko B. Popovic. Application Ser. No. 11/499,853 claims the benefit of the filing date of, U.S. Provisional Patent Application Ser. No. 60/705,651 filed on Aug. 4, 2005.

This application is also a continuation in part of U.S. patent application Ser. No. 11/495,140 entitled "An Artificial Ankle-Foot System with Spring, Variable-Damping, and Series-Elastic Actuator Components" filed on Jul. 29, 2006 by Hugh M. Herr, Samuel K. Au, Peter Dilworth, and Daniel Joseph Paluska. Application Ser. No. 11/495,140 claims the benefit of the filing date of U.S. Provisional Patent Application Ser. No. 60/704,517 filed on Aug. 1, 2005 and was also a continuation in part of the above-noted application Ser. No. 11/395,448.

This application is also a continuation in part of U.S. patent application Ser. No. 11/600,291 entitled "Exoskeletons for running and walking" filed on Nov. 15, 2006 by Hugh M. Herr, Conor Walsh, Daniel Joseph Paluska, Andrew Valiente, Kenneth Pasch, and William Grand. Application Ser. No. 11/600,291 claims the benefit of the filing date of U.S. Provisional Patent Application Ser. No. 60/736,929 filed on Nov. 15, 2005 and is a continuation in part of the above noted applications Ser. Nos. 11/395,448, 11/499,853 and 11/495,140.

The present application claims the benefit of the filing date of each of the foregoing patent applications and incorporates the disclosure of each of the foregoing applications herein by reference.

FIELD OF THE TECHNOLOGY

This invention relates to artificial joints and limbs for use in prosthetic, orthotic or robotic devices.

BACKGROUND

Biomimetic Hybrid Actuators employed in biologically-inspired musculoskeletal architectures as described in the above noted U.S. patent application Ser. No. 11/395,448 employ an electric motor for supplying positive energy to and storing negative energy from an artificial joint or limb, as well as elastic elements such as springs, and controllable variable damper components, for passively storing and releasing energy and providing adaptive stiffness to accommodate level ground walking as well as movement on stairs and surfaces having different slopes.

The above noted application Ser. No. 11/495,140 describes an artificial foot and ankle joint consisting of a curved leaf spring foot member that defines a heel extremity and a toe extremity, and a flexible elastic ankle member that connects said foot member for rotation at the ankle joint. An actuator motor applies torque to the ankle joint to orient the foot when it is not in contact with the support surface and to store energy in a catapult spring that is released along with the energy stored in the leaf spring to propel the wearer forward. A ribbon clutch prevents the foot member from rotating in one direction beyond a predetermined limit position, and a controllable damper is employed to lock the ankle joint or to absorb mechanical energy as needed. The controller and a sensing mechanisms control both the actuator motor and the controllable damper at different times during the walking cycle for level walking, stair ascent and stair descent.

The above noted U.S. patent application Ser. No. 11/600,291 describes an exoskeleton worn by a human user consisting of a rigid pelvic harness worn about the waist of the user and exoskeleton leg structures each of which extends downwardly alongside one of the human user's legs. The leg structures include hip, knee and ankle joints connected by adjustable length thigh and shin members. The hip joint that attaches the thigh structure to the pelvic harness includes a passive spring or an active actuator to assist in lifting the exoskeleton and said human user with respect to the ground surface upon which the user is walking and to propel the exoskeleton and human user forward. A controllable damper operatively arresting the movement of the knee joint at controllable times during the walking cycle, and spring located at the ankle and foot member stores and releases energy during walking.

The additional references listed below identify materials which are referred to in the description that follows. When cited, each reference is identified by a single number in brackets; for example, the first reference below is cited using the notation "{1}."

1. Palmer, Michael. Sagittal Plane Characterization of Normal Human Ankle Function across a Range of Walking Gait Speeds. Massachusetts Institute of Technology Master's Thesis, 2002.
2. Gates Deanna H., Characterizing ankle function during stair ascent, descent, and level walking for ankle prosthesis and orthosis design. Master thesis, Boston University, 2004.
3. Hansen, A., Childress, D. Miff, S. Gard, S. and Mesplay, K., The human ankle during walking: implication for the design of biomimetic ankle prosthesis, Journal of Biomechanics, 2004 (In Press).
4. Koganezawa, K. and Kato, I., Control aspects of artificial leg, IFAC Control Aspects of Biomedical Engineering, 1987, pp. 71-85.
5. Herr H, Wilkenfeld A. User-Adaptive Control of a Magnetorheological Prosthetic Knee. Industrial Robot: An International Journal 2003; 30: 42-55.
6. Seymour Ron, Prosthetics and Orthotics: Lower limb and Spinal, Lippincott Williams & Wilkins, 2002.
7. G. A. Pratt and M. M. Williamson, "Series Elastic Actuators," presented at 1995 IEEE/RSJ International Conference on Intelligent Robots and Systems, Pittsburgh, Pa., 1995.
8. Inman V T, Ralston H J, Todd F. Human walking Baltimore: Williams and Wilkins; 1981.

9. Hof. A. L. Geelen B. A., and Berg, J. W. Van den, "Calf muscle moment, work and efficiency in level walking; role of series elasticity," Journal of Biomechanics, Vol 16, No. 7, pp. 523-537, 1983.
10. Gregoire, L., and et al, Role of mono- and bi-articular muscles in explosive movements, International Journal of Sports Medicine 5, 614-630.
11. Endo, K., Paluska D., Herr, H. A quasi-passive model of human leg function in level-ground walking *IEEE/RSJ International Conference on Intelligent Robots and Systems (IROS)*; Oct. 9-16, 2006; Beijing, China.

As noted in references {1}, {2}, {3}, and {4} above, an artificial limb system that mimics a biological limb ideally needs to fulfill a diverse set of requirements. The artificial system must be a reasonable weight and have a natural morphological shape, but still have an operational time between refueling or battery recharges of at least one full day. The system must also be capable of varying its position, stiffness, damping and nonconservative motive power in a comparable manner to that of a normal, healthy biological limb. Still further, the system must be adaptive, changing its characteristics given such environmental disturbances as walking speed and terrain variation. The current invention describes a novel actuator and limb architecture capable of achieving these many requirements.

From recent biomechanical studies described in references {1}, {2} and {3} above, researchers have determined that biological joints have a number of features. Among these are:
(a) the ability to vary stiffness and damping;
(b) the ability to generate large amounts of positive mechanical work (nonconservative motive output); and
(c) the ability to produce large amounts of power and torque when needed.

An example of the use of more than one control strategy in a single biological joint is the ankle. See {1} and {2}. For level ground ambulation, the ankle behaves as a variable stiffness device during the early to midstance period, storing and releasing impact energies. Throughout terminal stance, the ankle acts as a torque source to power the body forward. In distinction, the ankle varies damping rather than stiffness during the early stance period of stair descent. These biomechanical findings suggest that in order to mimic the actual behavior of a human joint or joints, stiffness, damping, and nonconservative motive power must be actively controlled in the context of an efficient, high cycle-life, quiet and cosmetic biomimetic limb system, be it for a prosthetic or orthotic device. This is also the case for a biomimetic robot limb since it will need to satisfy the same mechanical and physical laws as its biological counterpart, and will benefit from the same techniques for power and weight savings.

The current state of the art in prosthetic leg systems include a knee joint that can vary its damping via magnetorheological fluid as described in {5}, and a carbon fiber ankle which has no active control, but that can store energy in a spring structure for return at a later point in the gait cycle e.g. the Flex-Foot {4} or the Seattle-Lite {6}. None of these systems are able to add energy during the stride to help keep the body moving forward or to reduce impact losses at heel strike. In the case of legged robotic systems, the use of the Series Elastic Actuator (SEA) enables robotic joints to control their position and torque, such that energy may be added to the system as needed. See {7}. In addition, the SEA can emulate a physical spring or damper by applying torques based on the position or velocity of the joint. However, for most applications, the SEA requires a tremendous amount of electric power for its operation, resulting in a limited operational life or an overly large power supply. Robotic joint designs in general use purely active components and often do not conserve electrical power through the use of variable-stiffness and variable-damping devices.

SUMMARY

The following summary provides a simplified introduction to some aspects of the invention as a prelude to the more detailed description that is presented later, but is not intended to define or delineate the scope of the invention.

In this specification and the claims, the following terms have the following meanings:
actuator: see the definition of "motor" below;
agonist: A contracting element that is resisted or counteracted by another element, the antagonist;
agonist-antagonist actuator: a mechanism comprising (at least) two actuators that operate in opposition to one another: an agonist actuator that, when energized, draws two elements together and an antagonist actuator that, when energized, urges the two elements apart;
antagonist: An expanding element that is resisted or counteracted by another element, the agonist;
biomimetic: a man-made structure or mechanism that mimics the properties and behavior of biological structures or mechanisms, such as joints or limbs;
dorsiflexion: bending the ankle joint so that the end of the foot moves upward;
elastic: capable of resuming an original shape after deformation by stretching or compression;
extension: A bending movement around a joint in a limb that increases the angle between the bones of the limb at the joint;
flexion: A bending movement around a joint in a limb that decreases the angle between the bones of the limb at the joint;
motor: an active element that produces or imparts motion by converting supplied energy into mechanical energy, including electric, pneumatic or hydraulic motors and actuators;
plantarflexion: bending the ankle joint so that the end of the foot moves downward;
spring: an elastic device, such as a metal coil or leaf structure, which regains its original shape after being compressed or extended.

For an artificial joint to behave like a biological joint, a synthetic actuator must have the following properties:

1) The actuator must consume negligible power when exerting zero force. Near the equilibrium length of muscle (peak of active tension-length curve), the passive tension is typically zero. Thus a muscle-actuated joint goes limp when the muscles are not electrically stimulated.

2) The actuator must consume negligible power when outputting force at constant length (isometric) and while performing dissipative, nonconservative work. Muscle tissue is very efficient for isometric and dissipative control modes.

3) The actuator must be capable of independently engaging flexion and extension tendon-like, series springs. Since biological joints have at least one flexor muscle and at least one extensor muscle, the time at which a flexor tendon becomes taught or engaged can be independent of the time at which an extensor tendon becomes engaged. As an example, with a muscle-actuated joint, the elastic energy from one tendon can be released as a second tendon is being elongated.

4) The actuator must be capable of independently varying joint position and stiffness. Through co-contraction between a muscle flexor and extensor, joint stiffness can be modulated without changing joint position. Further, joint position can be varied while keeping joint stiffness constant.

5) The actuator must be capable of exploiting series elasticity for mechanical power amplification, or a "catapult" control modality. For motion tasks that require high mechanical power, muscle-tendon units in animals and humans often employ a catapult control where the muscle belly stretches the series tendon, and later that stored elastic energy is released to achieve relatively higher joint powers than would be possible if the muscle belly were to generate that power directly.

BRIEF DESCRIPTION OF THE DRAWINGS

In the detailed description which follows, frequent reference will be made to the attached drawings, in which:

FIG. 13A shows the major components of the transtibial system are shown;

FIG. 13B shows the monoarticular ankle mechanism of FIG. 13A in more detail;

DETAILED DESCRIPTION

In the construction of a biologically realistic limb system that is high performance, light weight, quiet and power efficient, a agonist-antagonist actuator design is proposed herein comprising a plurality of actuators and series elastic structures. Since it is desirable to minimize the overall weight of the limb design, the efficiency of the agonist-antagonist actuator design is critical, especially given the poor energy density of current power supplies, e.g. lithium-ion battery technology. By understanding human biomechanics, the lightest, most energy efficient agonist-antagonist actuator design can be achieved.

In the next section, the key features of biomechanical systems are highlighted. A more complete description of biomechanical systems is found in the patent applications cited in the foregoing "Cross Reference to Related Applications" whose disclosures are incorporated herein by reference.

Joint Biomechanics: The Human Ankle

Understanding normal walking biomechanics provides the basis for the design and development of the agonist-antagonist actuator design. Specifically, the function of human ankle under sagittal plane rotation is described for different locomotor conditions including level-ground walking and stair/slope ascent and descent. In addition, the function of the human knee during level ground walking is described. From these biomechanical descriptions, the justifications for key mechanical components and configurations of the actuator invention are established.

Level-Ground Walking

Figure 1:
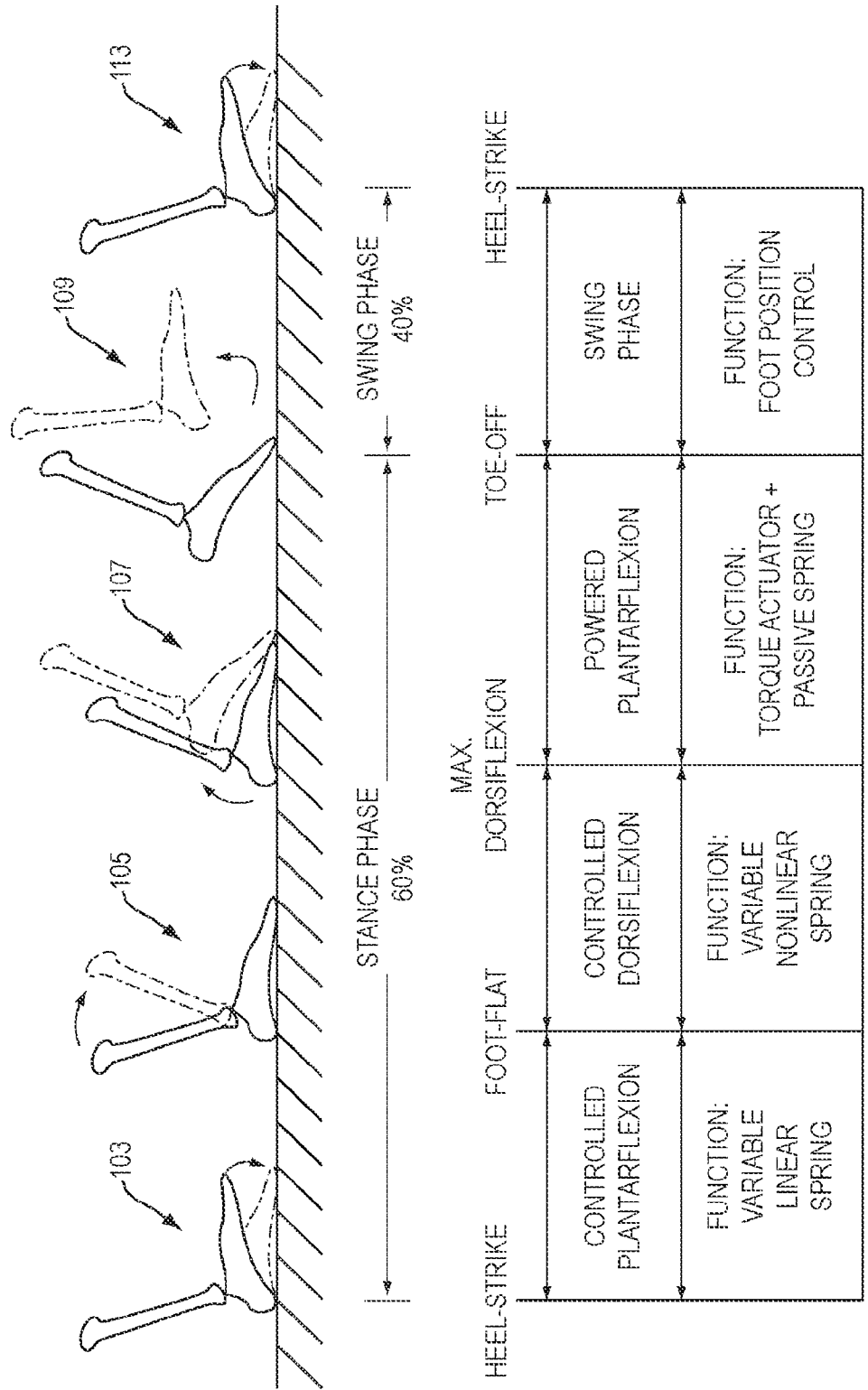
FIG. 1 depicts the various subdivisions of the stance phase of walking.

A level-ground walking gait cycle is typically defined as beginning with the heel strike of one foot seen at 103 in FIG. 1 and ending at the next heel strike of the same foot seen at 113. See {8}. The main subdivisions of the gait cycle are the stance phase (~60%) and the swing phase (~40%) which are illustrated in FIG. 1. The swing phase represents the portion of the gait cycle when the foot is off the ground. The stance phase begins at heel strike when the heel touches the floor and ends at toe off when the same foot rises from the ground surface. Additionally, we can further divide the stance phase into three sub-phases: Controlled Plantar Flexion (CP), Controlled Dorsiflexion (CD), and Powered Plantar Flexion (PP).

Detailed descriptions for each phase and the corresponding ankle functions are described in FIG. 1. CP begins at heel-strike 103 and ends at foot-flat shown at 105. Simply speaking, CP describes the process by which the heel and forefoot initially make contact with the ground. In {1} and {3}, researchers showed that CP ankle joint behavior is consistent with a linear spring being loaded or stretched where joint torque is proportional to joint position.

During the loading process, the spring behavior is, however, variable; joint stiffness is continuously modulated by the body from step to step. After the CP period, the CD phase begins. In FIG. 2, the average torque versus angle curves are shown for 68 healthy, young participants walking on a level surface. As is shown, during CP (from 103 to 105), the ankle behaves as a linear spring of variable stiffness during the loading cycle, but the torque curve does not trace back to point 1, but rather assumes higher torque values during the early period of CD.

Ankle torque versus position during the CD period from 105 to 107 can often be described as a nonlinear spring being loaded or stretched where stiffness increases with increasing ankle position. It is noted that as walking speed increases, the extent to which the ankle behaves as a nonlinear spring increases, with the CD loading phase exhibiting distinct nonlinear behavior during fast walking (see fast walking, FIG. 2). The main function of the ankle during CD is to store elastic energy to propel the body upwards and forwards during the PP phase. See {9} and {3}.

The PP phase begins at 107 after CD and ends at the instant of toe-off shown at 109. During PP in moderate to fast walking speeds, the ankle can be modeled as a catapult in series or in parallel with the CD spring or springs. Here the catapult component includes an actuator that does work on a series spring during the CD phase and/or during the first half of the PP phase. The catapult energy is then released along with the spring energy stored during the CD phase to achieve the high plantar flexion power during late stance. This catapult behavior is necessary because the work generated during PP is more than the negative work absorbed during the CP and CD phases for moderate to fast walking speeds as clearly seen in FIGS. 2A-2C. See {1}, {2}, {3} and {9}.

Figure 2A:
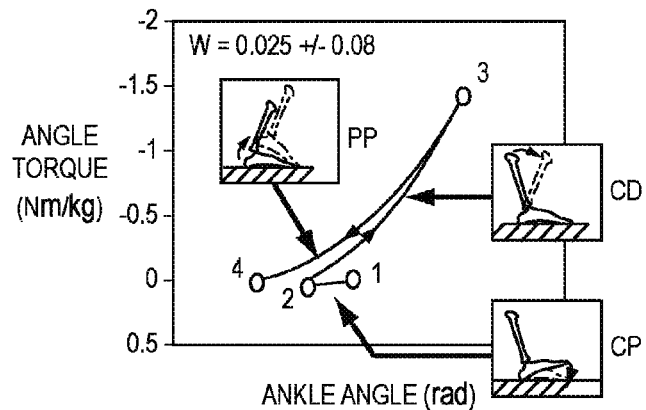
FIGS. 2A, 2B and 2C show torque vs. angle plots in level-ground walking for slow speed, normal and fast walking.
Figure 2B:
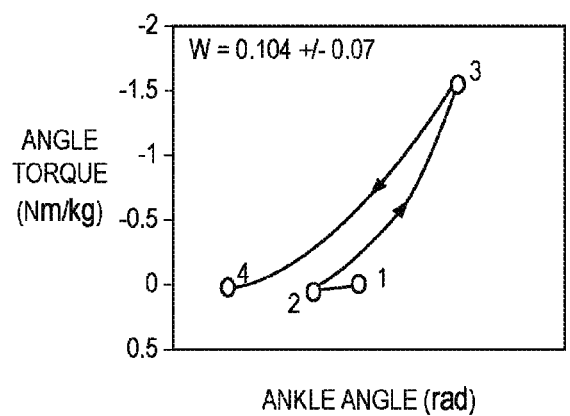
Figure 2C:
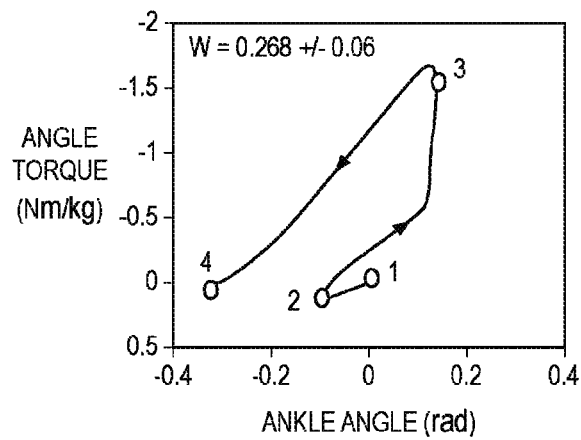

FIGS. 2A, 2B and 2C show torque vs. angle plots in level-ground walking for slow speed walking at 0.9 m/sec (FIG. 2A), normal walking speed at 1.25 m/sec (FIG. 2B) and fast walking at 1.79 m/sec. Only the stance period of a single foot is shown (heel strike to toe off). Point 1 on the charts denotes heel strike, point 2 foot flat, point 3 peak dorsiflexion, and point 4 toe off. Although during slow walking the loading curve (points 2-3) is approximately equal to the unloading curve (points 3-4), for higher walking speeds the torque assumes higher values during the unloading, PP phase (points 3-4). Hence, for walking speeds greater than 0.9 m/s (slow speed), the human ankle cannot be modeled as a series of coupled springs because the positive work performed by the ankle exceeds the negative work. It is noted that, as walking speed increases, the degree of nonlinear behavior during CD (points 2-3) increases along with the total amount of positive work production during PP (points 3-4), consistent with a catapult model where the soleus muscle belly slowly elongates the series Achilles tendon spring during CD, increasing the slope of the torque versus angle curve and the subsequent positive power output of the ankle.

Stair Ascent and Descent

Figure 3:
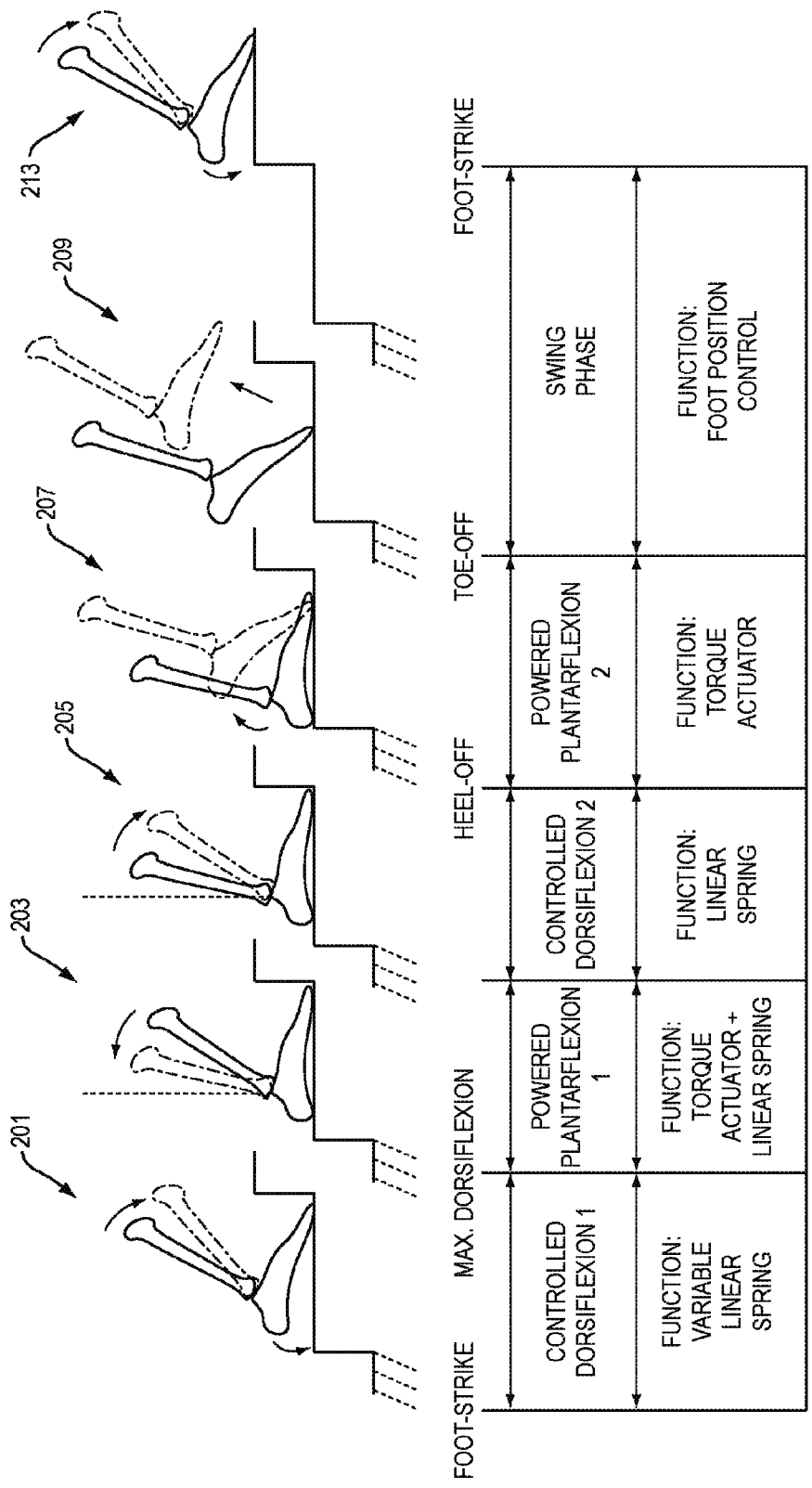
FIG. 3 illustrates human ankle biomechanics for stair ascent.

FIG. 3 illustrates human ankle biomechanics for stair ascent; The first phase of stair ascent is called Controlled Dorsiflexion 1 (CD 1), which begins with foot strike in a dorsiflexed position at 201 and continues to dorsiflex until the heel contacts the step surface at 203. In this phase, the ankle can be modeled as a linear spring. The second phase is Powered Plantar flexion 1 (PP 1), which begins at the instant of foot flat (when the ankle reaches its maximum dorsiflexion) at 203 and ends when dorsiflexion begins once again at 205. The human ankle behaves as a torque actuator to provide extra energy to support the body weight. The third phase is Controlled Dorsiflexion 2 (CD 2), in which the ankle dorsiflexes as seen at 205 until heel-off at 207. For that phase, the ankle can be modeled as a linear spring. The fourth and final phase is Powered Plantar flexion 2 (PP 2). Here the foot pushes off the step as seen at 207, acting as a torque actuator in parallel with the CD 2 spring to propel the body upwards and forwards until toe-off occurs at 209 and the swing phase begins.

Figure 4:
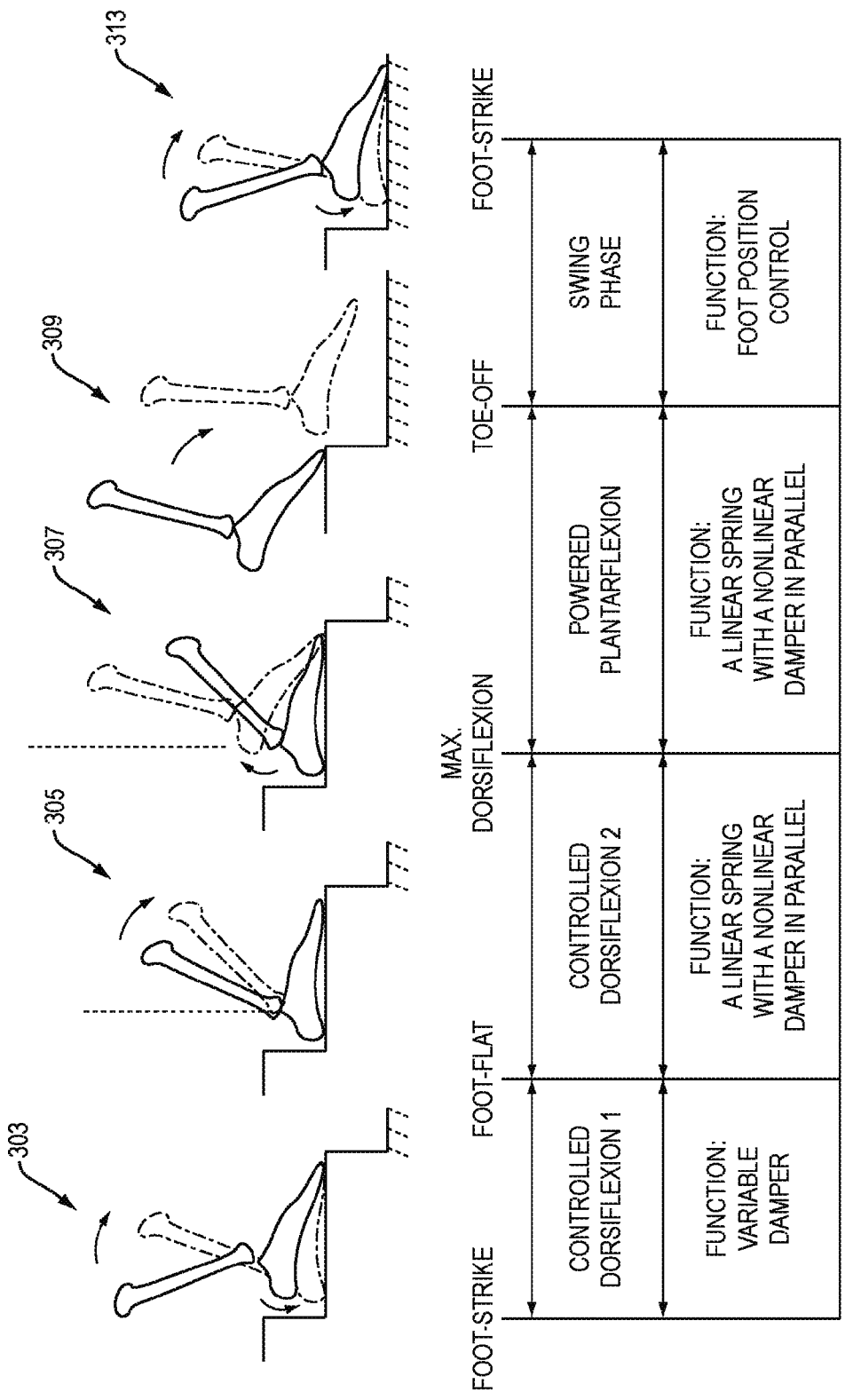
FIG. 4 illustrates human ankle-foot biomechanics for stair descent.

FIG. 4 illustrates the human ankle-foot biomechanics for stair descent. The stance phase of stair descent is divided into three sub-phases: Controlled Dorsiflexion 1 (CD1), Controlled Dorsiflexion 2 (CD2), and Powered Plantar flexion (PP). CD1 begins at forefoot strike seen at 303 and ends at foot-flat seen at 305. In this phase, the human ankle can be modeled as a variable damper. In CD2, from foot flat at 305, the ankle continues to dorsiflex forward until it reaches a maximum dorsiflexion posture at 307. Here the ankle acts as a linear spring in series with a variable-damper designed to effectively control the amount of energy stored by the linear spring. During PP, beginning at 307, the ankle plantar flexes until the foot lifts from the step at 309. In this final phase, the ankle releases stored CD2 energy, propelling the body upwards and forwards. From toe off at 309 until the next foot strike at 313, the foot in the swing phase.

Because the kinematic and kinetic patterns at the ankle during stair ascent/descent are significantly different from that of level-ground walking (see {2}), a description of such ankle-foot biomechanics seems appropriate. For stair ascent, the human ankle-foot can be effectively modeled using a combination of an actuator and a variable stiffness mechanism. However, for stair descent, variable damping needs also to be included for modeling the ankle-foot complex; the power absorbed by the human ankle is much greater during stair descent than the power released by 2.3 to 11.2 J/kg. See reference {2}.

Joint Biomechanics: The Human Knee

Figure 5A:
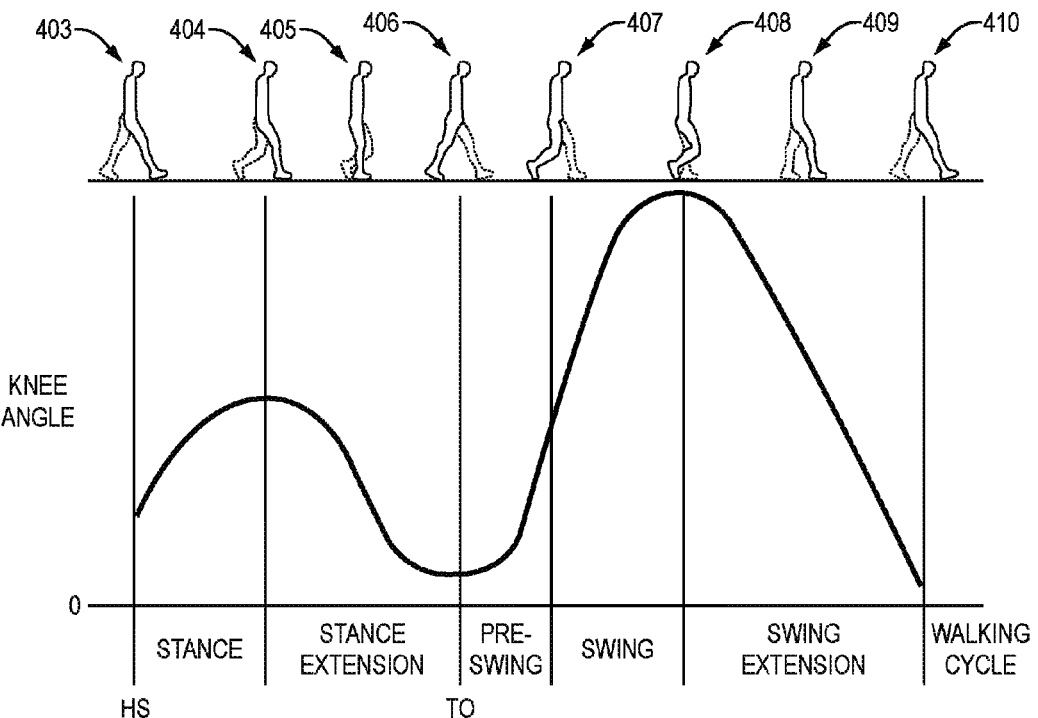
FIGS. 5A and 5B illustrate the manner in which knee angle and knee power respectively vary during the walking cycle for level ground walking.
Figure 5B:
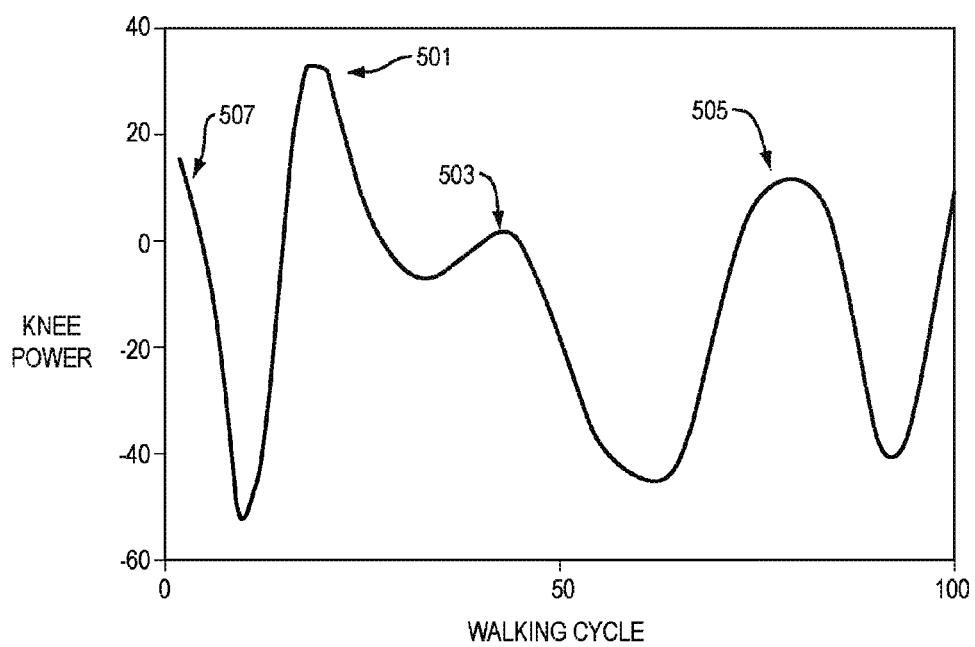

There are five distinct phases to knee operation throughout a level-ground walking cycle as illustrated in FIGS. 5A and 5B. See reference {8}. FIG. 5A shows how the knee angle varies during the walking cycle, and FIG. 5B shows how knee power varies. As seen in FIG. 5A, the stance phase of walking can be divided into three sub-phases: Stance Flexion, Stance Extension, and Pre-Swing. The swing phase is divided into two phases: Swing Flexion and Swing Extension. As seen in FIG. 5B, for level ground walking, the human knee does more negative work than positive work.

Beginning at heel strike indicated at 403, the stance knee begins to flex slightly. This flexion period, called the Stance Flexion phase, allows for shock absorption upon impact as well as to keep the body's center of mass at a more constant vertical level throughout the stance period. During this phase, the knee acts as a spring, storing energy in preparation for the Stance Extension phase.

After maximum flexion is reached in the stance knee at 404, the joint begins to extend, until maximum extension is reached as indicated at 406. This knee extension period is called the Stance Extension phase. Throughout the first ~60% of Stance Extension, the knee acts as a spring, releasing the stored energy from the Stance Flexion phase of gait. This first release of energy corresponds to power output indicated at 501 in the graph at the bottom of FIG. 5B. During the last ~30% of Stance Extension, the knee absorbs energy in a second spring and then that energy is released during the next gait phase, or Pre-Swing.

During late stance or Pre-Swing from 406 to 407, the knee of the supporting leg begins its rapid flexion period in preparation for the swing phase. During early Pre-Swing, as the knee begins to flex in preparation for toe-off, the stored elastic energy from Stance Extension is released. This second release of energy corresponds to power output seen at 503 in FIG. 5B.

As the hip is flexed, and the knee has reached a certain angle in Pre-Swing, the leg leaves the ground at 407 and the knee continues to flex. At toe-off 407, the Swing Flexion phase of gait begins. Throughout this period, knee power is generally negative where the knee's torque impedes knee rotational velocity. During terminal Swing Flexion, the knee can be modeled as an extension spring in series with a variable damper, storing a small amount of energy in preparation for early Swing Extension.

After reaching a maximum flexion angle during swing at 408, the knee begins to extend forward. During the early Swing Extension period, the spring energy stored during late Swing Flexion is then released, resulting in power output seen at 505 in FIG. 5B. During the remainder of Swing Extension, the human knee outputs negative power (absorbing energy) to decelerate the swinging leg in preparation for the next stance period. During terminal Swing Extension, the knee can be modeled as a flexion spring in series with a variable damper, storing a small amount of energy in preparation for early stance (at 507). After the knee has reached full extension, the foot once again is placed on the ground, and the next walking cycle begins.

An agonist-antagonist actuator described below implements these muscle-like actuation properties. The actuator comprises a plurality of springs, mechanical transmissions, and active elements where each spring is in series with an active element via a transmission, and each spring-transmission-active element combination are in parallel and capable of opposing one another in an agonist-antagonist manner. The components of the agonist-antagonist actuator are listed in Table 1 with their functional purposes outlined.

The Agonist-Antagonist Actuator: An Example

Figure 6A:
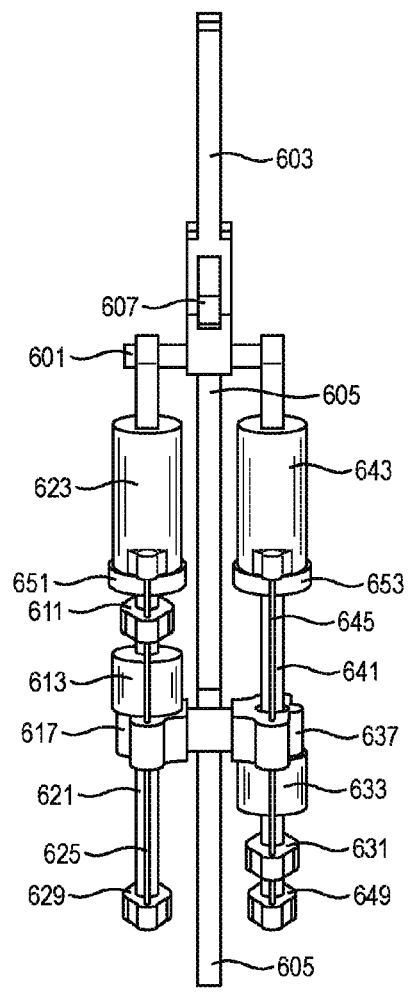
FIGS. 6A and 6B are posterior and side elevational views respectively of an agonist-antagonist actuator embodying the invention.
Figure 6B:
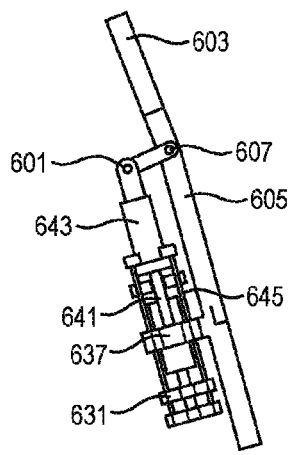

In FIG. 6, one implementation of the actuator is shown as an example. For this particular actuator form, the active element comprises a motor in parallel with a variable damper. The flexion and extension motors can control the position of flexion and extension nuts, respectively, via ballscrew mechanical transmissions. As seen in FIG. 6, two side-by-side actuators are attached at their upper ends to a cross-rod 601 which provides a connection point to the upper link 603 of the joint mechanism. The upper link 603 is connected to the lower link 605 at a joint 607.

The actuator that extends along the left-hand side of the upper and lower links 603 and 605 as seen in FIG. 6 includes an extension nut 611 that engages with and compresses an extension spring 613. The extension spring 613 is positioned between the extension nut 611 and a linear bearing 617 which is attached to the lower link 605. An extension ballscrew seen at 621 connected via a gearbox (not shown) to the armature of an extension motor 623. An extension nut guidance shaft 625 is attached to the case of the motor 623 and extends downwardly from the motor 623 through the extension nut 611 and the linear bearing 617 to a shaft endcap 629. The guidance shaft 625 prevents the extension nut from rotating so that, as the extension motor 623 rotates the extension ballscrew 621, the extension nut 611 moves longitudinally with respect to the cross-rod 601 and the motor 623, varying the joint angle at which the extension nut engages with the extension spring 613. Thus, the extension motor 623 can compress the extension spring 613 as the extension nut 611 is driven downward to increase the length of the actuator and extend (increase) the joint angle.

The actuator that extends along the right-hand side of the upper and lower links 603 and 605 as seen in FIG. 6 includes a flexion nut 631 that engages with and compresses a flexion spring 633. The flexion spring 633 is positioned between the flexion nut 631 and a linear bearing 637 which is attached to the lower link 605. A flexion ballscrew seen at 641 connected via a gearbox (not shown) to the armature of a flexion motor 643. A flexion nut guidance shaft 645 is attached to the case of the flexion motor 643 and extends downwardly from the motor 643 through the linear bearing 637 and the flexion nut 631 and the to a flexion shaft endcap 649. The flexion nut guidance shaft 645 prevents the extension nut from rotating so that, as the flexion motor 643 rotates the flexion ballscrew 641, the flexion nut 631 moves longitudinally with respect to the cross-rod 601 and the flexion motor 643, varying the joint angle at which the flexion nut engages with the flexion spring 633. Thus, the flexion motor 623 can compress the flexion spring 633 as the flexion nut 631 is driven upwardly to decrease the length of the actuator and decrease the joint angle during flexion.

A variable damper is connected in parallel with each of the motors. An extension variable damper seen at 651 is connected in parallel with the extension motor 623 and a flexion variable damper seen at 653 is connected in parallel with the flexion motor 643.

Through the independent control of flexion and extension nut positions, the actuator length at which the flexion and extension springs are engaged can be independently controlled (Muscle-Like Property 3). Furthermore, the flexion and extension motors can compress each series spring simultaneously without the joint rotating where each spring exerts an equal but oppositely opposed force.

If the series springs are hardening springs where spring stiffness increases with increasing compression, joint stiffness can be effectively controlled through this agonist-antagonist motor action (Muscle-like property 4). After the motors co-contract and compress the flexion and extension springs to a desired spring deflection and a desired actuator stiffness, to maintain that stiffness, the variable dampers can output high damping levels to impede ballscrew rotation at low power requirements.

Since each motor is in parallel with each variable damper, both motors can be turned off while still maintaining spring deflection and overall actuator stiffness (Muscle-Like Property 2). The actuator can also dissipate mechanical energy at low power (Muscle-Like Property 2).

In the actuator form of FIG. 6, the ballscrew transmissions are backdrivable. Hence, when an external agent compresses or lengthens the actuator, energy can be dissipated using the variable dampers. Since each variable damper is in parallel with each motor, during such a dissipative action, the motors can act as generators to store electrical power for later use. Finally, zero actuator force can be achieved at zero power consumption (Muscle-Like Property 1). If the motors move the ballscrew nuts away from their respective spring element, the actuator will output zero force and no energy is required to maintain that force.

Component Implementations

Active Element. Depending on the application, each active element could be either a motor or a variable damper/clutch, or a combination of these elements. If the active element includes a variable damper/clutch, it could be implemented using hydraulic, pneumatic, friction, electrorheological, magnetorhelogical, hysteresis brake, or magnetic particle brake damping/clutching strategies. The preferred mechanism for damping control is a hysteresis brake because the zero power damping level is negligible. This feature is important because the variable damper is behind the mechanical transmission where any strain rate dependent, low-end viscous or frictional effect would likely be amplified.

If the active element includes a motor, it could be any electric motor, brushed or brushless. It could also be a hydraulic or pneumatic cylinder or other mechanical power-producing elements such as artificial muscle, piezoelectrics or nitinol wire.

Spring. The springs could be implemented as linear or torsional spring elements. They may be metal die springs, carbon fiber leaf springs, elastomeric compression springs, or pneumatic springs. For the preferred implementations described in this specification, the springs are die compression springs.

Mechanical Transmission. The mechanical transmissions could be implemented as linear or torsional transmission elements. They could be harmonic drives, ballscrew drives, leadscrew drives, or any other mechanical transmission known in the art. For the case where the active element and the series spring are both linear or both rotary elements, and no gear reduction is deemed necessary, the transmission would simply be a material linkage, connecting spring to active element. For example, if the active element is a linear artificial muscle, and the spring a linear, elastomeric element, then the spring would simply be attached directly to the artificial muscle. For the preferred embodiments described in FIGS. 6-10, the mechanical transmissions are ballscrew transmissions.

TABLE 1

Mechanical components of the Agonist-Antagonist Actuator System

| Component | Function |
|---|---|
| Spring | Store and release energy, absorb shock, provide stiffness |
| Active Element | Control positive and negative work and power, control effective spring equilibrium length and stiffness, generate electrical power, clutch to engage series elasticity |
| Mechanical Transmission | Couple spring to active element, offer gear reduction between active element and output, convert rotary active element to linear spring element |

Sensing Implementations

For the Agonist-antagonist actuator to function properly, there are various sensors required to measure the state of the various actuator components. The sensors required to enable general actuator operation and control are:
1) Position sensors located at the biomimetic joint axis to measure joint angle (a rotary potentiometer), and at the active element (motor/variable damper/clutch) rotor to measure total displacement of the element's drive shaft and additionally the active element's velocity (a shaft encoder).
2) A force sensor (strain gauges) to measure the actual torque borne by the joint.
3) A displacement sensor on each spring in order to measure the amount of energy stored.

Instead of directly measuring the deflection of the series springs (#3), sensory information from #1 can be employed. By subtracting the biomimetic joint angle from the active element output shaft angle, it is possible to calculate the amount of energy stored in the motor series spring. Also, the series spring displacement sensor can be used to measure the torque borne by the joint because joint torque can be calculated from the series spring output force.

Many variations exist in the particular sensing methodologies employed in the measurement of the listed parameters. Although preferred sensory methods have been specified, it is noted here that what is critical is to capture the energy state of the spring elements and the velocities of interior points.

In the remaining sections, we present embodiments of the agonist-antagonist actuator capable of providing biologically realistic dynamic behaviors for an artificial ankle and knee joint.

An Agonist-Antagonist Actuator for an Artificial Ankle Joint

Mechanical Design

The ankle design comprises flexion and extension motors for the active elements, and corresponding flexion and extension transmissions and springs. The flexion and extension motors provide control of joint spring equilibrium position and stiffness, damping and nonconservative, motive force output. In the section to follow, we provide an example of how the agonist-antagonist actuator could be employed as an artificial ankle.

Figure 7A:
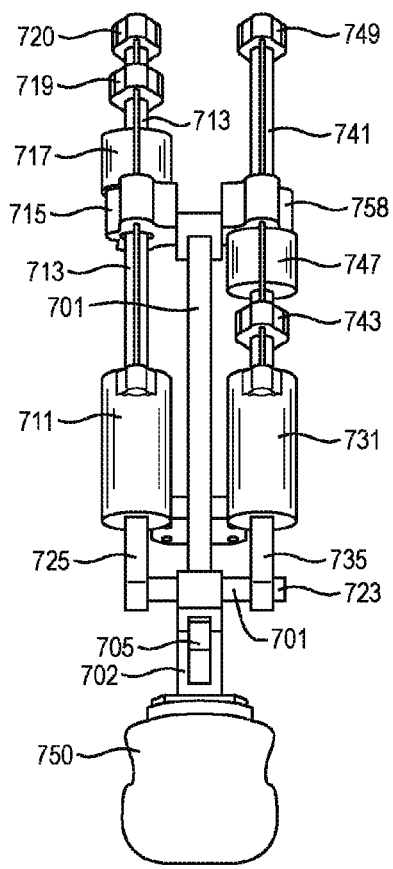
FIGS. 7A and 7B are posterior and side elevational views of an agonist-antagonist actuator mechanism implementing an artificial ankle.
Figure 7B:
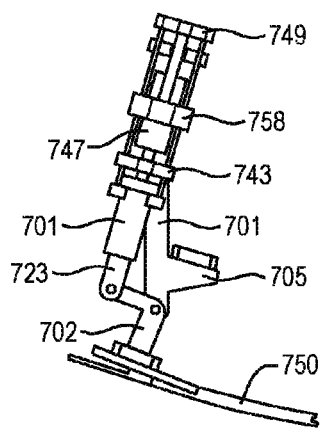

The Agonist-antagonist actuator, as used in an artificial ankle application, is shown in FIGS. 7A and 7B. An upper shin link 701 and a foot link 702 rotate with respect to one another about an ankle joint 705 as best seen in the side view, FIG. 7B. Two actuators extend in parallel alongside the shin link 701. In the actuator seen at the left in FIG. 7A, a plantar flexion motor 711 drives a flexion ballscrew 713 that extends through a linear bearing 715, a plantar flexion spring 717 and a plantar flexion nut 719 to an endcap 720. The flexion motor 711 is attached to a crossrod 723 by a strut 725. The dorsiflexion actuator is seen at the right in FIG. 7A and includes a dorsiflexion motor 731 which is attached at its lower end by a strut 735 to the cross rod 723. A dorsiflexion ballscrew 741 is driven by the dorsiflexion motor and extends upwardly through a dorsiflexion nut 743, a dorsiflexion spring 747, and a linear bearing 758 to an endcap 749. The foot link 702 is attached to a leaf spring foot plate seen at 750.

The description that follows explains how, during level-ground walking, the joint might be controlled for the swing, controlled plantar flexion (CP), controlled dorsiflexion (CD), and powered plantar flexion (CP) phases of gait. In addition, the description will explain how the joint might be controlled for stair/slope ascent and descent.

Level-Ground Walking: Swing Phase and CP

During early swing, the plantar flexion ballscrew nut 719 is positioned such that the ankle joint is dorsiflexed to achieve foot clearance. During terminal stance, three distinct control methods can be employed in preparation for heel strike and the CP phase. In human walking, the amount of energy stored during CP increases with increasing walking speed. To achieve this increase in energy with speed, the total angular deflection of the ankle can be increased with increasing speed and/or the quasi-stiffness or the actual stiffness of the ankle can be increased. Thus, in a first control approach, the effective spring equilibrium length of the actuator at heel strike could be increased with increasing walking speed. Here the spring equilibrium position of the joint is equal to the desired heel strike ankle angle. The effect of this control would be that more mechanical energy is stored in the dorsiflexion spring during CP as walking speed increases. In an alternate approach, during terminal swing both dorsi and plantar flexion motors 731 and 711 could do work on their respective series springs in a co-contraction control scheme. If the series springs are hardening springs (stiffness increases with increasing deflection), this co-contraction action would effectively increase the actual stiffness of the actuator, and the ankle joint across which the actuator spans. Still further, in a third approach, the quasi-stiffness of the actuator/joint could be increased or decreased during CP. For the ankle system shown in FIGS. 7A and 7B, the flexion and extension ballscrews are non-backdriveable. Hence, during CP, if the desired ankle stiffness can be achieved simply by compressing the dorsiflexion spring 747, the dorsiflexion motor 731 can be turned off to conserve power. If a lower quasi joint stiffness is required, the dorsiflexion motor 731 can unwind the dorsiflexion spring 747 during CP, and if a greater quasi joint stiffness is required, the motor can compress the spring 747 during CP. Depending on the terrain (smooth or uneven), walking speed, and power consumption constraints, the control algorithm of the artificial ankle will select the appropriate ankle spring equilibrium and stiffness values for terminal swing/CP to achieve a smooth heel strike to forefoot strike transition.

It is noted here that in the invention described herein, there can be separate series spring stiffnesses for joint dorsi and plantar flexion, and these two sets of springs 717 and 747 can be selected to give distinct flexion and extension joint stiffnesses at little to no power consumption. If the motors change ankle position when minimal torques are applied to the joint, such as during the swing phase of walking, very little electrical power is required to change the spring equilibrium position of the joint. In the embodiment seen in FIGS. 7A and 7B, where the ballscrews 713 and 741 are non-backdriveable, the motors need not consume any electrical power to hold the joint's position even during ground contact. Controlling the joint spring set point at heel strike can be useful, for example, when the wearer switches shoes with different heel heights or when the terrain changes character (slopes/stairs and uneven terrain), thus changing the natural angle of the ankle joint when the foot is resting on a flat ground surface.

Level-Ground Walking: CD and CP Phases

During early CD in human walking, the ankle torque does not return to point 1 in FIG. 2. Rather, the torque assumes a higher value compared to the torque values from points 1 to 2. To achieve this higher torque output, the plantar flexion motor 711 has to move the plantar flexion nut 719 to reduce the gap between the nut and the plantar flexion spring 717 as the dorsiflexion spring 747 is being compressing during CP. This repositioning of the plantar flexion nut allows the plantar flexion spring to be engaged even before the dorsiflexion spring has released its energy, thus providing a higher torque during early CD than during CP.

During mid to terminal CD in human walking, the ankle torque versus angle curve becomes increasingly nonlinear as walking speed increases. In addition, peak ankle power and the net ankle work during stance increases with increasing walking speed (see FIG. 2). Thus, at 0.9 m/sec, when the human ankle, on average, stores as much energy as it releases, the mechanical response of the artificial ankle during CP will, on average, be dictated by the series, plantar flexion spring. That is to say, the stiffness of the plantar flexion spring will be tuned to correspond to the average, quasi-stiffness (slope of the torque-angle curve) of the human ankle during CD. To decrease the quasi-stiffness of the artificial ankle during CP, the plantar flexion motor would be controlled to unwind the plantar flexion spring, and to increase quasi-stiffness, the motor would compress the spring. Thus, as walking speed increases above 0.9 m/sec, the plantar flexion motor would compress the plantar flexion spring during CD to achieve the following characteristics 1) to increase the quasi-stiffness of the artificial ankle during CD and 2) to increase the power output and the positive work performed during PP. It is noted here that to achieve a passive, spring response during the stance period of walking, the flexion and extension motors can be turned off to conserve power since the ballscrews are nonbackdriveable.

From {1} {2}, it has been shown that the maximum dorsiflexion ankle torque during level-ground walking is in the range from 1.5 Nm/kg to 2 Nm/kg, i.e. around 150 Nm to 200 Nm for a 100 kg person. Further, the maximum controlled plantar flexion torque is relatively small, typically in the range of 0.3 Nm/kg to 0.4 Nm/kg. Because of these biomechanics, a uni-directional spring in parallel with the agonist-antagonist actuator of FIGS. 7A and 7B would lower the peak torque requirements of the actuator. The uni-directional spring would engage at a small or zero dorsiflexion angle (90 degrees between foot and shank) and would lower the peak torque requirements of the Agonist-antagonist actuator since the peak controlled plantar flexion torque is considerably smaller than the peak dorsiflexion torque. Thus, additional elements could be added to the design of FIG. 7 such as a parallel, uni-directional spring.

Stair/Slope Ascent and Descent

For ascending a stair or slope, the dorsi and plantar flexion motors would move the nuts to reposition the ankle joint to an appropriate angle given the nature of the stair/slope. Once the artificial toe is loaded at first ground contact, the plantar flexion spring compresses and stores energy. During this CD process the plantar flexion motor can compress the spring farther so that additional power is delivered to the walking robot or prosthesis/orthosis user during PP. After toe-off, the motors control the equilibrium position of the ankle in preparation for the next step.

During stair descent, the body has to be lowered after forefoot contact until the heel makes contact with the stair tread. See re reference {2}. During this CD phase, the plantar flexion motor unwinds the plantar flexion spring as the spring is compressing to effectively dissipate mechanical energy. Once the heel makes contact with the stair tread, the motor can be turned off so that the plantar flexion spring begins to store energy for release during PP. For slope descent, the ankle response is similar, except that mechanical energy is absorbed by the dorsiflexion motor during CP instead of during CD.

An Agonist-Antagonist Actuator for an Artificial Knee Joint

The knee design comprises an extension motor and a flexion variable damper for the active elements, and corresponding flexion and extension transmissions and springs. The extension motor and the flexion variable damper provide control of joint spring equilibrium position and stiffness, damping and nonconservative, motive force output. In this implementation of the agonist-antagonist actuator, a flexion motor is not included in an attempt to simplify the mechanism. Since only a flexion variable damper is present, the flexion nut is mechanically grounded to the linear bearing since a flexion motor is not present to actively reposition the flexion nut. Hence, when the knee joint flexes and extends, the flexion ballscrew rotations, but that rotation does not introduce significant zero-power joint resistance because 1) the flexion ballscrew is highly backdriveable and 2) the flexion variable damper has a negligible low-end damping value. A preferred method for the flexion variable damper is a hysteresis brake because of its minimal low-end damping value. In the section to follow, I provide an example of how the agonist-antagonist actuator could be employed as an artificial knee.

Figure 8A:
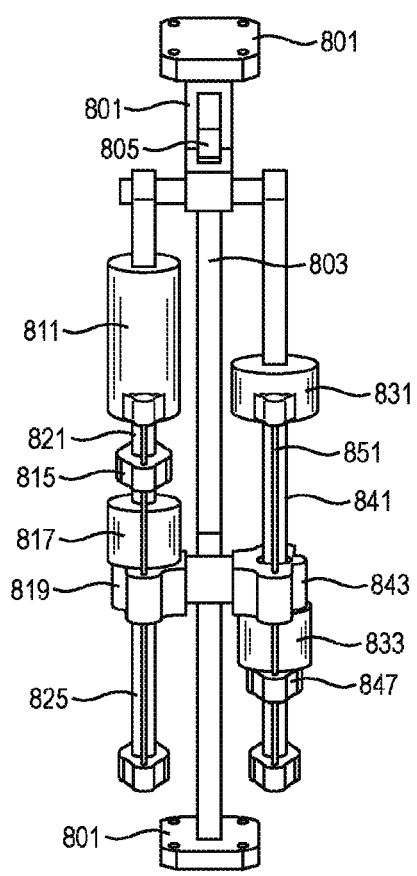
FIGS. 8A and 8B are posterior and side elevational views of agonist-antagonist actuator mechanisms implementing an artificial knee.
Figure 8B:
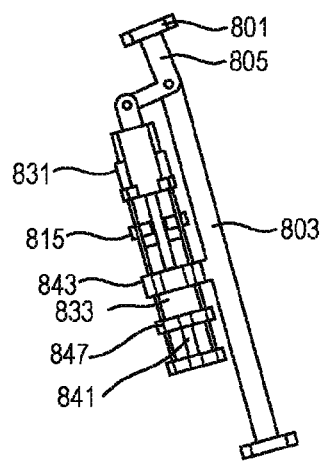
Figure 9A:
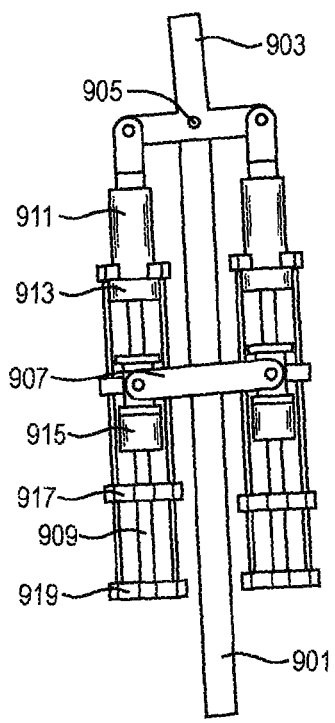
FIGS. 9A and 9B are side elevational and perspective views of an agonist-antagonist actuator mechanism positioned on both sides of the joint axis.
Figure 9B:
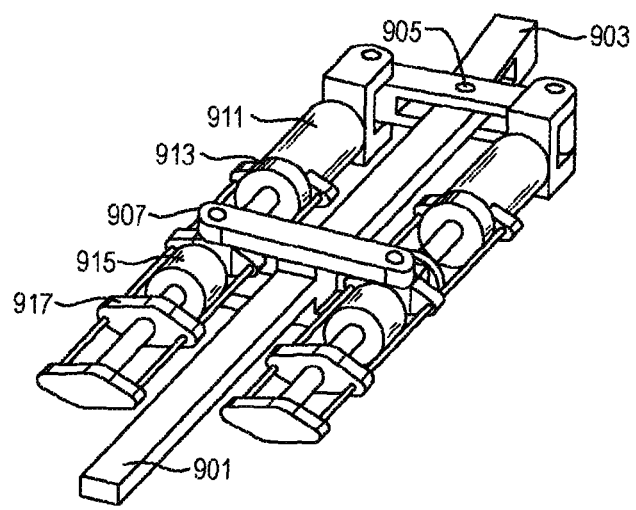

The agonist-antagonist actuator, as used in an artificial knee application, is shown in FIGS. 8A and 8B. The actuator consists of an upper (thigh) link 801 and a lower (shin) link 803 which are rotatably connected at a joint 805. As seen at the left of the lower link 803, an extension motor 811 drives an extension ballscrew 821 that extends downwardly from the motor 811 through an extension nut 815, an extension spring 817, and a linear bearing 819. An extension nut guidance shaft 825 prevents the extension nut from rotating as the extension ballscrew 821 rotates.

The mechanism on the right side of the lower link 803 is passive; that is, it does not include an active motor element but rather includes a flexion variable damper 831 and a flexion spring 833. A flexion ballscrew 841 extends from the damper 831 downwardly through a linear bearing 843, the flexion spring 833 and a flexion nut 847. A flexion nut guidance shaft 851 prevents the flexion nut 847 from rotating as the extension ballscrew 841 rotates.

Level-Ground Walking

During level-ground walking, the joint is controlled for the swing, early stance flexion, mid-stance extension, and pre-swing phases of gait. In addition, as described below, the joint may be controlled for stair/slope ascent and descent. Beginning at heel strike, the stance knee begins to flex slightly in normal human walking (FIG. 5). As was noted earlier, this flexion period, called the Stance Flexion phase, allows for shock absorption upon impact as well as to keep the body's center of mass at a more constant vertical level throughout the stance period. During this phase, the artificial knee shown in FIGS. 8A and 8B outputs a spring response, storing energy in preparation for the Stance Extension phase. Here the extension spring 817 stores energy, and then that energy is released during the Stance Extension phase. In this implementation of the agonist-antagonist actuator, the extension ballscrew transmission is non-backdriveable. Thus, if the desired actuator stiffness during Stance Flexion corresponds to the extension spring stiffness, the extension motor need not be active, reducing electrical power requirements. If a higher or lower quasi joint stiffness is desired, the extension motor 811 can compress or unwind the extension spring 813 during early stance knee flexion, respectively, by repositioning the extension nut 815 that acts on the extension spring 817.

After maximum flexion is reached in the stance knee in normal human walking, the joint begins to extend, until maximum extension is reached. This knee extension period is called the Stance Extension phase. Throughout the first ~60% of Stance Extension, the knee acts as a spring, releasing the stored energy in the extension spring from the Stance Flexion phase of gait. This first release of energy corresponds to power output P2 in FIG. 5B. During the last ~30% of Stance Extension, the artificial knee is controlled to absorb energy in the flexion spring 833 and then that energy is released during the next gait phase, or Pre-Swing. Here the energy from hip muscular work and the remaining stored energy in the extension spring 817 is then stored in the flexion spring 833. To engage the flexion spring, the flexion variable damper 831 outputs a high damping value, locking the flexion ballscrew 841, and forcing the flexion nut 847 to compress the flexion spring 833. During this energy storage, if it is desirable to lower the effective quasi-stiffness of the joint, the flexion variable damper 831 can output lower damping values to allow the flexion ballscrew 841 to slip, and for energy to be dissipated as heat. Here again, as in the artificial ankle joint of FIGS. 7A and 7B, the flexion and extension springs of the agonist antagonist actuator of FIGS. 8A and 8B are precisely tuned such that biological knee mechanics can be achieved while minimizing power supply demands and overall artificial joint mass.

During late stance or Pre-Swing, a normal human knee of the supporting leg begins its rapid flexion period in preparation for the swing phase. During early Pre-Swing in the artificial knee joint of FIGS. 8A and 8B, as the knee begins to flex in preparation for toe-off, the stored elastic energy in the flexion spring 833 stored during Stance Extension is released. This second release of energy corresponds to power output P3 in FIG. 5B. During this process, the flexion variable damper 831 can be used to modulate the amount of stored elastic energy in the flexion spring that is actually released to power the knee joint.

In normal human walking, as the hip is flexed, and the knee has reached a certain angle in Pre-Swing, the leg leaves the ground and the knee continues to flex. At toe-off, the Swing Flexion phase of gait begins. Throughout this period, human knee power is generally negative where the knee's torque impedes knee rotational velocity. In the artificial knee joint of FIGS. 8A and 8B, once the elastic energy from the flexion spring 833 has been released and the artificial leg has entered the swing phase, the knee joint typically has to absorb mechanical energy to decelerate the swinging lower leg. This can be done in two ways. First, the flexion variable damper 831 can be used to dissipate mechanical energy as heat and to decelerate the swinging artificial leg. In addition, during late Swing Flexion, the extension motor 811 can position the extension ballscrew nut 815 such that the extension spring 817 compresses and stores elastic energy for use during Swing Extension.

After reaching a maximum flexion angle during swing, a normal human knee begins to extend forward. For the artificial knee of FIGS. 8A and 8B, during the early Swing Extension period, the elastic energy stored during late Swing Flexion in the extension spring 817 is released, resulting in power output P4 in FIG. 5B. This control action, once again, reduces the energy demands from the knee's power supply. In all cases, the flexion variable damper 831 can be used to precisely modulate the amount of power delivered to the swinging artificial leg from the stored elastic energy.

During the remainder of Swing Extension, the human knee typically outputs negative power (absorbing energy) to decelerate the swinging leg in preparation for the next stance period. As with Swing Flexion, this can be done in two ways. First, the flexion variable damper 831 can be used to dissipate mechanical energy as heat and to decelerate the swinging artificial leg. In addition, during late Swing Extension, the flexion variable damper 831 can output a relatively high damping value such that the flexion spring 833 compresses and stores elastic energy for use during Stance Flexion. Here a small amount of energy is stored in preparation for early stance (power P1). After the knee has reached full extension, the foot once again is placed on the ground, and the next walking cycle begins.

In summary, the artificial knee shown in FIGS. 8A and 8B is capable of reproducing the positive power contributions P1, P2, P3 and P4 shown in FIG. 5 for level-ground walking Stair/Slope Ascent and Descent For stair/slope descent, a normal human knee performs negative work during stance where knee torque is in the opposite direction to knee rotational velocity. The agonist-antagonist actuator of FIGS. 8A and 8B can perform this negative work in two ways. First, the flexion variable damper 831 can be used to dissipate mechanical energy as heat and to decelerate the rotating artificial leg. In addition, during terminal stance, the extension motor 811 can position the extension ballscrew nut 815 such that the extension spring 817 compresses and stores elastic energy for use later to power Swing Extension to prepare the artificial leg for the next stance period.

For stair/slope ascent, during the swing phase the extension motor 811 can actively control knee position to accurately locate the foot on the next stair tread or slope foothold. Once the artificial foot is securely positioned on the stair tread or ground, the motor 811 can then deflect and store energy in the extension spring 817. This stored elastic energy can then assist the knee wearer or humanoid robot to actively straighten the knee during the stance period, lifting the body upwards.

Finally, the agonist-antagonist actuator of FIGS. 8A and 8B allows for the "windup" phase of a catapult style control to occur at any desired time. This means much greater flexibility as to when large amounts of power can be efficiently generated and used. This flexibility is critical when designing an artificial knee that can be used for jumping. For such a movement task, energy has to be stored prior to the jump, and then the elastic energy has to be released at a precise time to facilitate a jumping action. Specifically for the agonist-antagonist actuator of FIGS. 8A and 8B, the flexion variable damper 831 would be controlled to output high damping to effectively lock the flexion ballscrew 841. Following this action, the extension motor 811 would slowly compress the extension spring 817. Once high powers are deemed necessary about the joint output, the flexion variable damper 831 would then be controlled to suddenly unlock to allow rapid rotation of the flexion ballscrew 841 and the release of elastic strain energy from the extension spring 817.

Alternative Configurations of the Agonist-Antagonist Actuator

It should be understood that the agonist-antagonist actuator described herein could be implemented in a number of different ways. For example, an active element and transmission-spring combination could be positioned on each side of the artificial joint. This configuration, shown in FIG. 9, has the advantage that when only one spring is being compressed, no off-axis bending torques are borne by the lower link seen at 901. The lower link 901 is attached to the upper link 903 at a joint 905. A crossbar strut 907 is rigidly attached to the lower link 901. A linear bearing is attached to each end of the crossbar strut 907 and a ballscrew, one of which is seen at 909, extends through the linear bearing. The ballscrew seen at 909 extends downwardly from a drive motor 911 through a variable damper 913, the linear bearing, a spring 915, and a ballscrew nut 917 to an end cap 919.

In the agonist-antagonist actuator implementations shown in FIGS. 6, 7 and 8, when only a single spring is being compressed, the upper and lower links experience a bending torque because the pair of active element-transmission-spring combinations are on the same side of the joint axis. It should also be understood that more than two active element-transmission-spring combinations could be employed to actuate multiple degrees of freedom. For example, in FIG. 10, four active element-transmission-spring combinations are shown to actuate a two degree of freedom joint. Still further, it should be understood that an agonist-antagonist actuation system can include active element-transmission-spring combinations than span two or more joints in a poly-articular architecture. The biomechanics of poly-articular actuation is discussed in the next section.

Figure 10A:
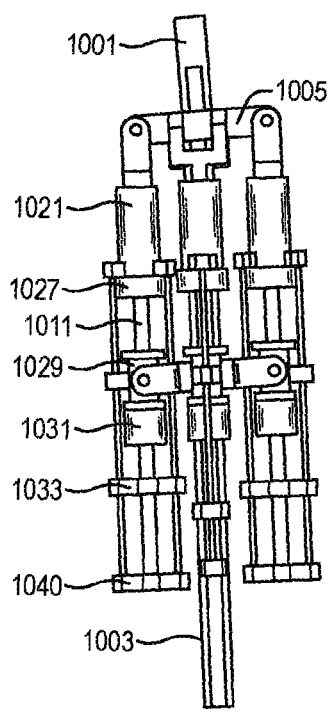
FIGS. 10A and 10B are posterior and side elevational views of an agonist-antagonist actuator mechanism using motor and spring combinations.
Figure 10B:
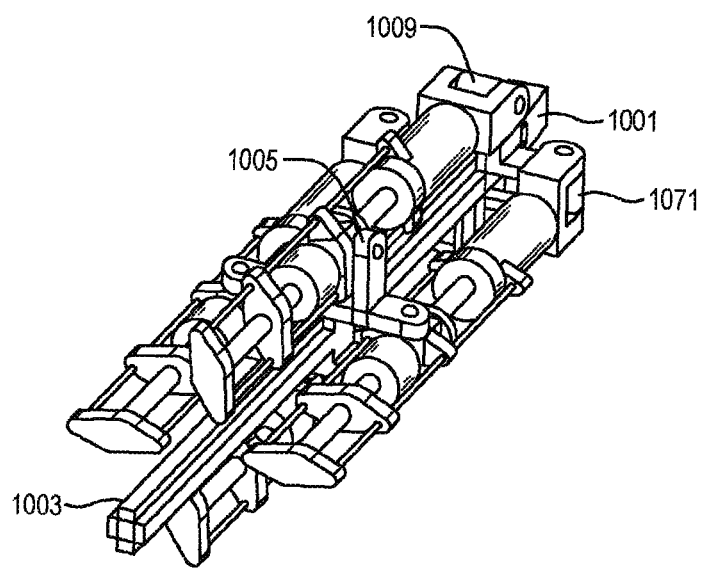

In the arrangement shown in FIG. 10, the joint attaches an upper link 1001 to a lower link 1003 for rotation about two orthogonal axes. As seen in FIG. 10B, the upper link rotates in a first degree of freedom about an axis through the crossbar 1007 that is parallel to the long dimension of a crossbar 1009, and in a second degree of freedom about an axis through the crossbar 1009 that is parallel to the crossbar 1007. Four different actuators are attached from the ends of the crossbars 1007 and 1009 and all four have a like structure illustrated by the actuator at the left in FIG. 10A. An drive motor 1021 attached to the crossbar 1005 rotates a ballscrew 1022 that passes through variable damper 1027 and a linear bearing 1029 attached to the lower link 1003. The ballscrew 1022 further extends through a series spring 1031 and a ballscrew nut 1033 to an endcap 1040. For each degree of freedom, one of the motor-spring-damper mechanisms controls the rotation of the upper link 1001 with respect to the lower link 103 in one direction while an opposing motor-spring-camper mechanism attached to other end of the same crossbar controls the rotation in that degree of freedom in the other direction, thus providing agonist-antagonist actuator control in both degrees of freedom.

Agonist-Antagonist Actuators Spanning More than One Joint

In the foregoing description, the agonist-antagonist actuator mechanism contemplated by the present invention was described and specific examples were provided as to its use in ankle and knee actuation, and different illustrative implementations were described. For each of these implementations, the agonist-antagonist actuator spanned a single joint. In other implementations, an agonist-antagonist actuator may span more than one rotary joint. The functional purpose of poly-articular muscle architectures in the human leg is to promote the transfer of mechanical energy from proximal muscular work to distal joint power generation. See reference {10}. To capture truly biomimetic limb function, both muscle-like actuators and mono, bi, and poly-articular artificial musculoskeletal architectures are critical. Hence, it should be understood that the agonist-antagonist actuator described herein could span more than one artificial joint. For example, an active element-transmission-spring combination could act across the hip and knee of an artificial leg, or across the knee and ankle of an artificial leg.

The Biomechanics of Mono and Bi-Articular Leg Actuation

In the previous sections, an agonist-antagonist actuator was described and specific examples were provided as to its use in ankle and knee actuation. For each of these descriptions, the actuator was used as a mono-articular device, spanning only a single joint. In subsequent embodiments, we describe how mono-articular actuation strategies can be used in combination with bi-articular actuation strategies to better replicate biological limb dynamics and efficiency.

The functional purpose of bi-articular muscle architectures in the human leg is to promote the transfer of mechanical energy from proximal muscular work to distal joint power generation {10}. To better explain how bi-articular actuation effects biological limb energetics, we present a biomechanical model of the human musculoskeletal architecture in FIG. 11A {11}. By modeling the human leg, we seek to understand how leg muscles and tendons work mechanically during walking in order to motivate the design of efficient prosthetic, orthotic, and robotic limbs.

We hypothesize that a robotic leg comprising only knee and ankle variable-impedance elements, including springs, clutches and variable-damping components, can capture the dominant mechanical behavior of the human knee and ankle for level-ground ambulation. As a preliminary evaluation of this hypothesis, we put forth a simple leg prosthesis model, shown in FIG. 11A, that is motivated by the human leg musculoskeletal architecture {11}. The model seen in FIG. 11 includes a drive motor 1101 at the hip, a knee joint 1103 and an ankle joint 1105. A musculo-skeletal model of human leg function in walking. The model comprises seven mono-articular series-elastic clutches and four bi-articular series-elastic clutches/variable-dampers. Only a single actuator 1101 acts at the model's hip joint. In (B) and (C), model predictions for ankle and knee are compared with human gait data, respectively. Here gait data are shown for a 70 kg study participant with a 0.9 meter leg length and a walking speed of 1.2m/s. The model of (A) agrees well with the human gait data, suggesting that muscles that span the ankle and knee primarily act as variable-impedance devices during level-ground walking. We vary quasi-passive model parameters, or spring constants, damping levels and times when series-elastic clutches are engaged, using an optimization scheme where errors between model joint behaviors and normal human joint biomechanics are minimized.

Figure 11A:
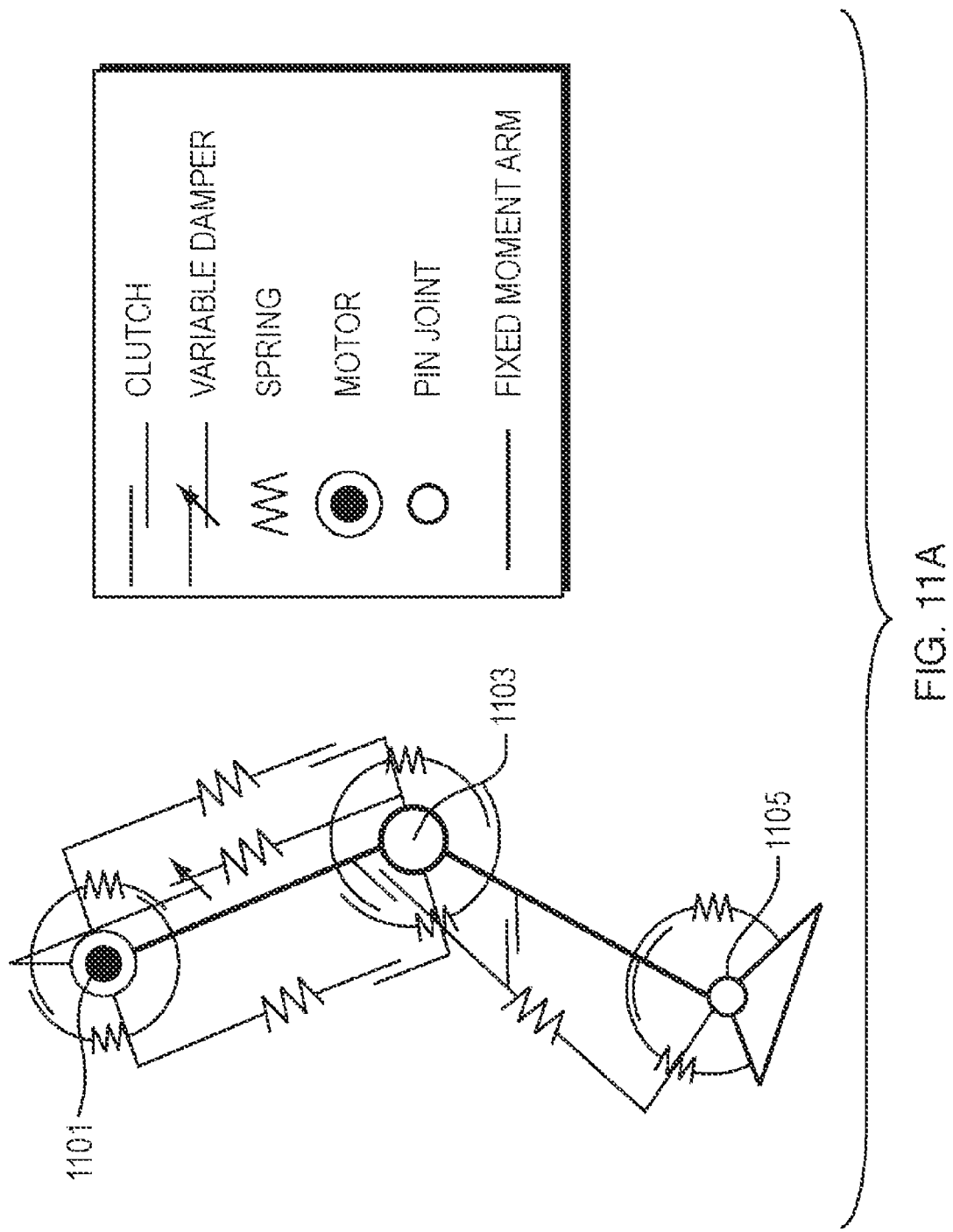
FIG. 11A shows a model of leg prosthesis employing series-elastic clutches at the hip, knee and ankle joints.
Figure 11B:
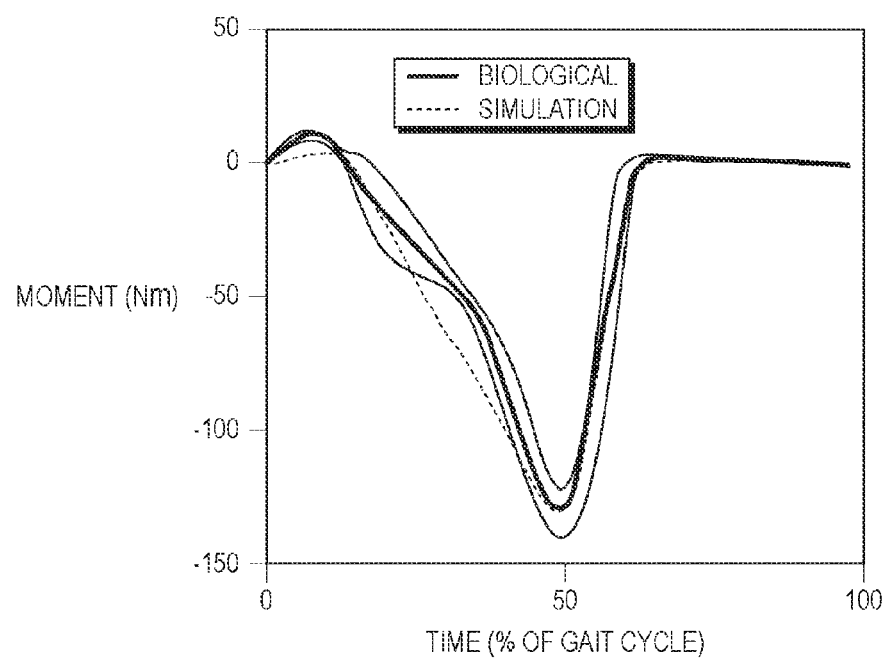
FIGS. 11B and 11C are graphs comparing the behaviors of biological ankle and knee joints respectively with the modeled joints of FIG. 11A.
Figure 11B:
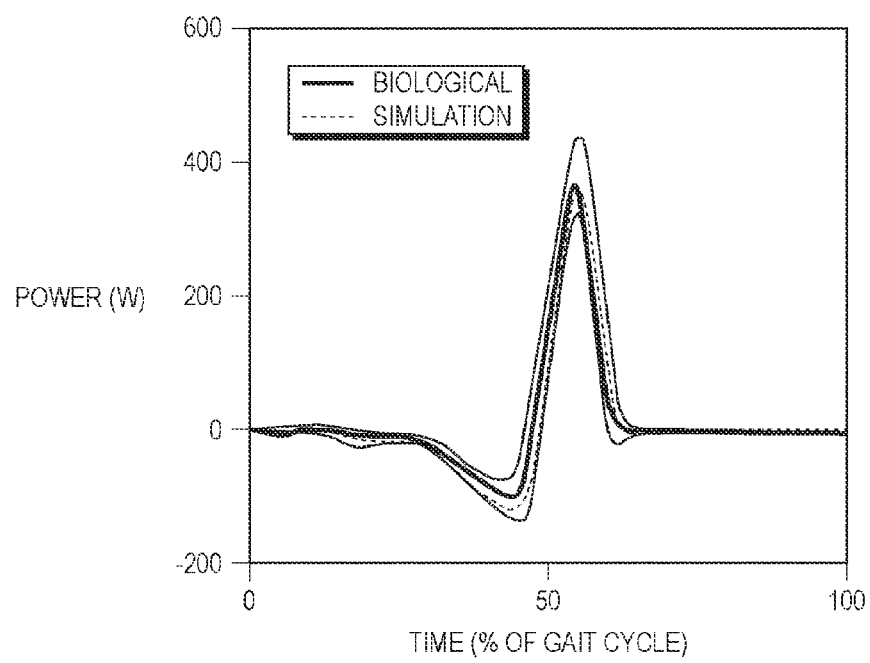
Figure 11C:
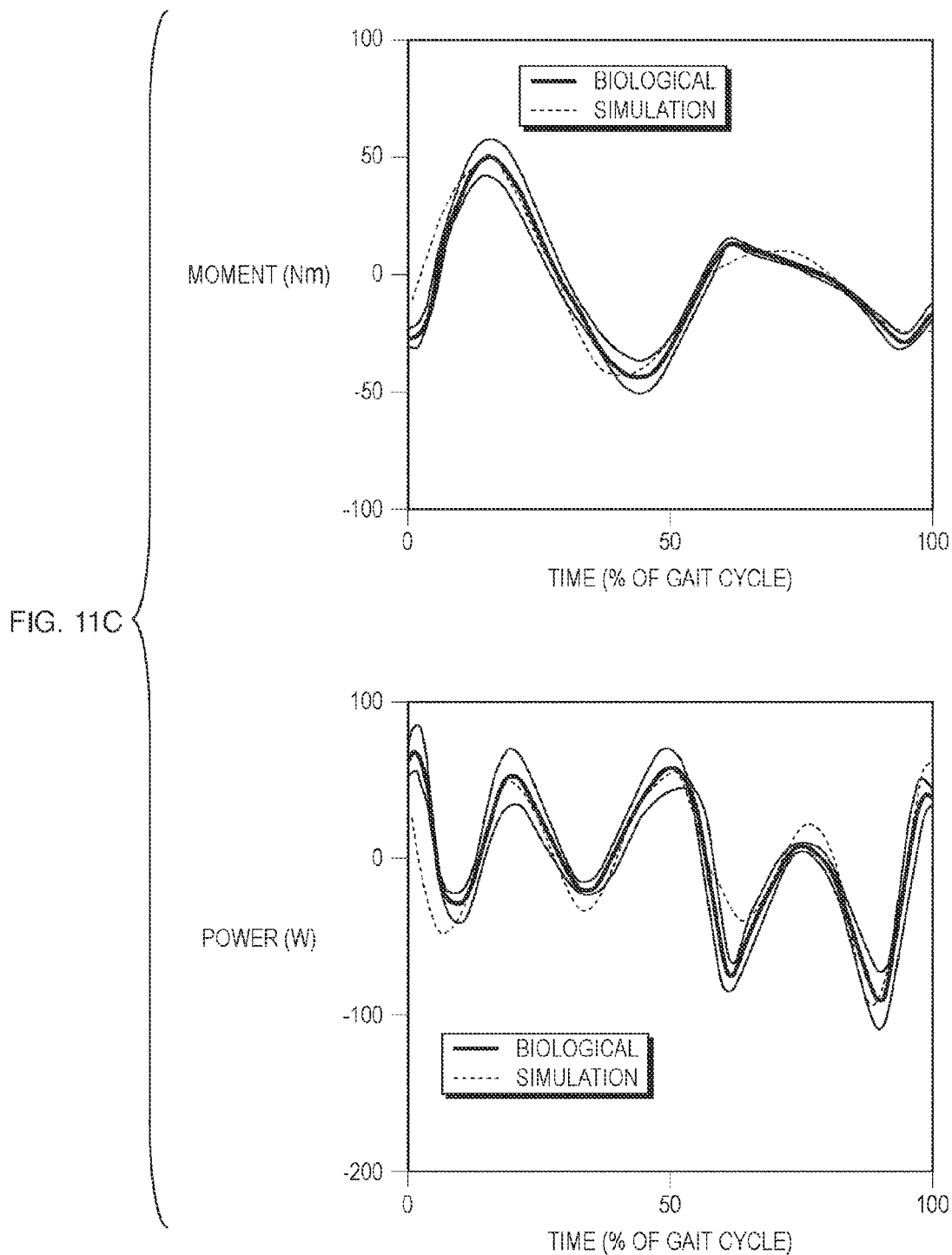

The capacity of the musculoskeletal leg model to capture human-like ankle and knee mechanics in level-ground walking is shown in FIGS. 11B and 11C, respectively. At each joint state (position and velocity), the leg model is in good agreement with experimental values of joint torque and power, suggesting that a robotic leg can produce human-like walking dynamics through the control of only knee and ankle impedance.

Figure 12A:
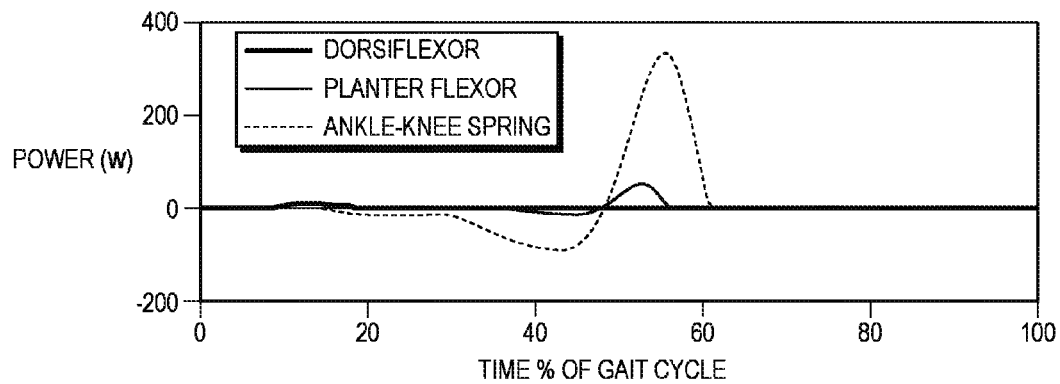
FIGS. 12A, 12B and 12C are plots of the mechanical power of each model element is versus percentage gait cycle for ankle, knee and hip, respectively.

Mono-articular ankle mechanism. The ankle mechanism comprises mono-articular dorsi and plantar flexion springs that can be engaged or disengaged with series elastic clutch mechanisms (see FIG. 11A). In FIG. 12A, the mechanical power for each ankle component is plotted versus percent gait cycle. At heel strike (0% cycle), the clutch for the ankle dorsiflexion spring is engaged, causing the spring to stretch and store energy during early stance plantar flexion. When the tibia begins rotating forwardly after forefoot contact, the ankle plantar flexion spring is engaged and continues to store energy throughout the controlled dorsiflexion phase, and then that stored energy is released to contribute to ankle powered plantar flexion at terminal stance. Mechanical power output for each component of the human leg model of FIG. 11A.

In (A), (B) and (C), the mechanical power of each model element is plotted versus percentage gait cycle for ankle, knee and hip, respectively. Here the gait cycle begins at heel strike (0%) and ends with the heel strike of the same leg (100%).

Figure 12B:
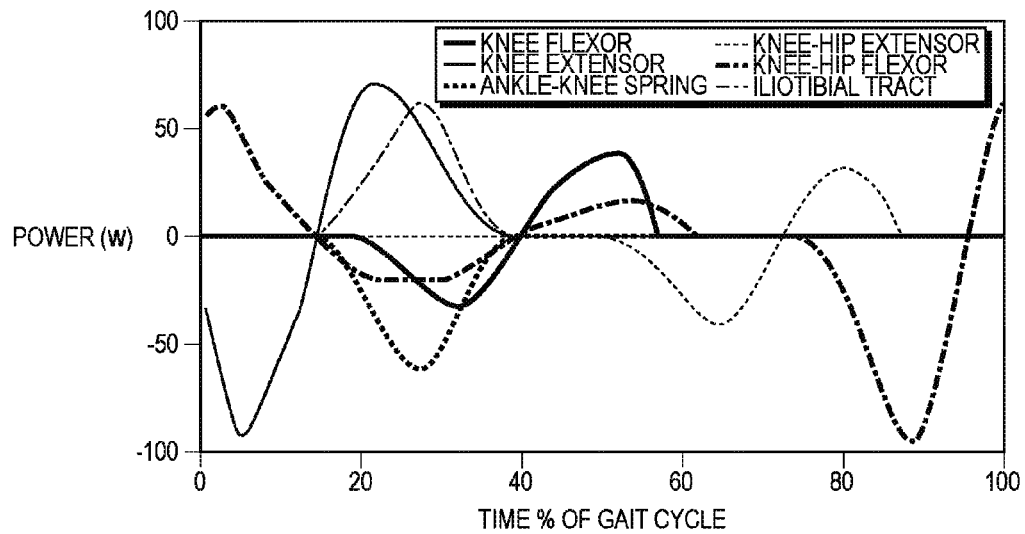

Mono-articular knee mechanism. The knee mechanism comprises mono-articular flexion and extension springs that can be engaged or disengaged with series elastic clutch mechanisms (see FIG. 11A). In FIG. 12B, the mechanical power for each knee mono-articular component is plotted versus percent gait cycle. At heel strike (0% cycle), the clutch for the knee extensor spring is engaged, causing the spring to stretch during early stance knee flexion. Here the knee extensor spring inhibits the knee from buckling. As the knee extends from a flexed posture, the knee flexor spring is engaged at the point of maximum knee extension velocity, storing energy that is subsequently used during terminal stance to help lift the lower leg from the ground surface.

Ankle-Knee Bi-Articular Mechanism. The leg model's ankle-knee bi-articular mechanism comprises a spring that can be engaged or disengaged with two clutch mechanisms (see FIG. 11A). A first clutch, or the distal clutch, attaches the series spring to a point between the ankle and knee joint, and a second clutch, or the proximal clutch, attaches that same spring to a point above the knee axis. After heel strike in human walking, the knee typically undergoes a flexion period. During that phase of gait, both the proximal and distal clutches are disengaged, and the bi-articular spring does not apply a force to the prosthesis skeleton. However, as the knee begins to extend (~10% cycle), the proximal clutch engages, and the bi-articular spring stretches. When the knee is fully extended, the distal clutch changes from a disengaged state to an engaged state, and the proximal clutch disengages. Engaging the distal clutch mechanically grounds the bi-articular spring below the knee rotational axis, changing the ankle-knee mechanism from a bi-articular to a mono-articular device. As a consequence of this action, all the energy stored in the bi-articular spring is used to power ankle plantar flexion during terminal stance. Thus in summary, the ankle-knee mechanism allows energy from hip muscular/actuator work to be transferred to the ankle for late stance powered plantar flexion.

Knee-Hip Bi-Articular Mechanism. The leg model's knee-hip bi-articular mechanisms comprise a spring that can be engaged or disengaged with either a clutch or variable-damper mechanism (see FIG. 11A). There are three knee-hip bi-articular mechanisms. The clutch of the knee-hip flexor is engaged during swing phase knee extension and begins storing energy its series spring. As a result of this control action, the lower leg is decelerated smoothly prior to reaching full knee extension. In addition, elastic energy is stored in the knee-hip flexor spring that is later released during the early stance period. The knee-hip flexor also undergoes an energy storage/release sequence that begins during stance knee extension. The stored energy is then released to power rapid knee flexion movements at terminal stance to lift the foot and lower leg from the ground surface. The clutch of the knee-hip extensor is engaged during terminal stance, storing energy that is later released to enhance knee extension. Finally, the iliotibial tract series-elastic variable-damper applies an extensor knee torque to offset the knee flexor torque applied by the ankle-knee bi-articular mechanism. During stance knee extension, the ankle-knee bi-articular spring is elongated, exerting a torque about the knee. At the same time the iliotibial tract series spring is elongated thereby applying an extensor torque at the knee. Thus, through the action of the iliotibial tract mechanism, the effect of the ankle-knee bi-articular mechanism on net knee torque is minimized.

Figure 12C:
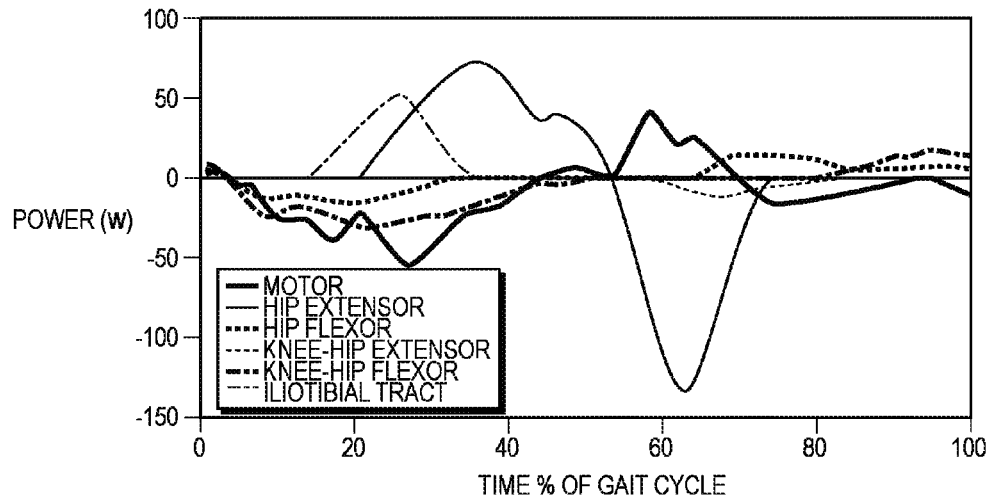

In the human leg, the functional purpose of bi-articular muscle is to promote the transfer of mechanical energy from proximal muscular work to distal joint power generation {10}. Using the biomimetic architecture shown in FIG. 11A, the robotic leg can achieve ankle powered plantar flexion without the requirement of powering a large motor located at the ankle joint. Approximately ten joules of net work are transferred to the ankle from the knee and hip in the modeling results shown in FIGS. 11 and 12.

In subsequent embodiments, we motivate the design of prosthetic, orthotic and robotic leg structures using the leg model of FIG. 11.

Mono and Bi-Articular Actuation for a Transtibial Prosthetic Leg System

The prosthetic leg model of FIG. 11A suggests that leg prostheses could produce human-like joint mechanics during level-ground ambulation if a musculoskeletal leg architecture and a variable-impedance control paradigm were exploited. However, the proposed biomimetic leg prosthesis does not eliminate the need for knee and ankle actuators, but the model does suggest that nonconservative joint actuator work need not be performed during normal, steady state walking For some situations, positive joint actuator work is required. For example, for uphill locomotory function, some positive actuator work would be necessary, especially at the knee. Furthermore, ankle and knee torque control would be necessary to reject large whole-body force disturbances that threaten balance. Although joint actuation is still necessary, the proposed biomimetic design will increase the time between battery recharges or power supply refueling, and will reduce robotic limb noise production during level-ground walking.

Figure 13C:
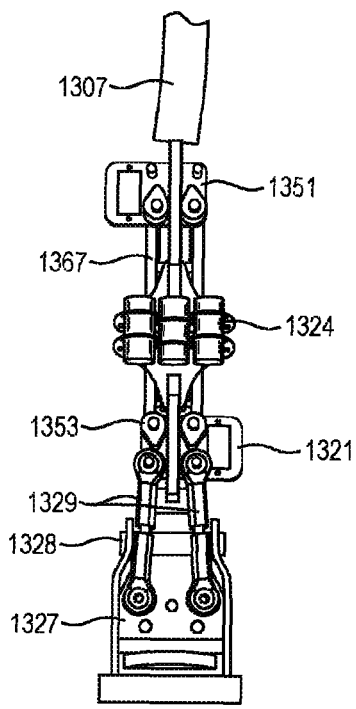
FIGS. 13C and 13D show elevational and schematic views respectively of the bi-articular ankle knee mechanism of FIG. 13A.
Figure 13D:
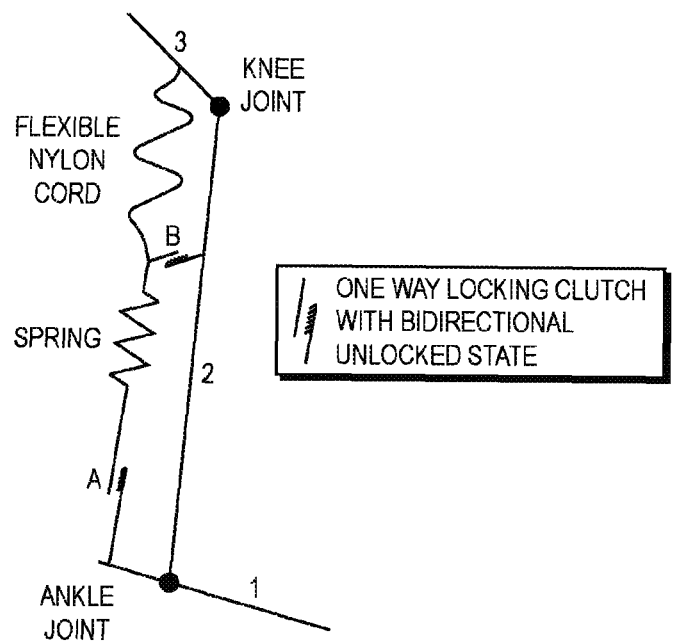

In FIG. 13, the design of the proposed transtibial ankle-foot system with mono and bi-articular mechanisms is shown. In FIG. 13A, the major components of the transtibial system are shown, including the mono-articular ankle mechanism at 1303, the bi-articular ankle-knee mechanism at 1305, and a flexible nylon cord at 1307. FIG. 13B shows the monoarticular ankle mechanism in more detail. This mechanism comprising two motors 1313, mechanical transmissions and series dorsiflexion springs at 1317, and series plantar flexion springs at 1319. FIG. 13C shows the bi-articular mechanism (1305 in FIG. 13A) and FIG. 13D shows a schematic of the bi-articular mechanism, including two uni-directional clutches seen at 1321 and 1351 and a series spring at 1324. The limb architecture largely reflects the leg model shown in FIG. 11A, except the mono-articular knee mechanism has been excluded as this basic musculoskeletal structure is still intact in transtibial amputees.

The ankle mechanism 1303 seen in FIG. 13B comprises two agonist-antagonist, series-elastic actuators acting across the ankle joint. The foot-ankle design is similar to that described earlier in FIG. 7. Each actuator has a small electric motor 1313 in series with one of the die springs 1317 or 1319. Each series spring is a nonlinear hardening spring where spring stiffness increases with increasing spring compression. A non-backdriveable leadscrew 1331 is employed to covert rotary motor movement into linear movement of a leadscrew nut 1332. A slider mechanism is seen at 1334 and a guide rod at 1335. By re-positioning the leadscrew nut 1332, each motor 1313 can independently vary the position of the ankle joint at which the series spring 1317 or 1319 becomes engaged. Such an ankle spring equilibrium control is important for many prosthesis functions, including slope and stair ascent and descent. The mono-articular ankle mechanism can also change ankle spring stiffness. During the swing phase each motor can simultaneously compress each nonlinear spring using a co-contraction control. Since spring stiffness increases with increasing deflection, the more the motor system compresses the springs, the stiffer the ankle joint becomes. Since the mechanical transmission is non-backdriveable, once a desired ankle stiffness has been achieved, the motors can be turned off to save electrical power. The foot-ankle design is similar to that described earlier in FIG. 7.

In FIGS. 13C and 13D, the bi-articular ankle-knee mechanism and schematic are shown, respectively. The mechanism comprises two uni-directional clutches seen at 1351 and 1321 and a spring at 1324. Each clutch is formed by two opposing cams (see 1353) that press against a shaft that directly connects to the spring. At the bottom of FIG. 13C, a foot assembly is seen at 1327 and the ankle axis is at 1328. The ankle joint connection is seen at 1329. In an engaged state, the cam configuration only allows for shaft movement in one direction. As can be seen in FIG. 13D, if both uni-directional clutches A and B are in the disengaged state, with each cam pair rotated outwardly with a small cam motor, the ankle and knee can freely rotate without the bi-articular spring exerting a force. When the ankle dorsi and plantar flexes in this disengaged state, the lower floating cam-clutch assembly 1321 translates on the linear guide rail 1367. Furthermore, when the knee flexes and extends, the entire spring assembly translates on the linear guide rail 1367. In distinction, when both clutches are in their engaged state, both ankle dorsiflexion and knee extension cause the bi-articular spring 1324 to stretch and store energy. Since the flexible nylon cord 1307 can resist tension but not compression, once the knee has reached full extension during the stance phase, knee flexion throughout terminal stance is not restricted by the bi-articular assembly, and all the stored energy in the bi-articular spring augments ankle powered plantar flexion.

Sensors for Active Ankle-Foot Prosthesis

For the active transtibial prosthesis to function properly, there are various sensors required to measure the state of the various system components and the intent of the amputee user. The additional sensors required to enable general prosthesis operation and control are:

4) position sensors located at the knee and ankle axes to measure joint angles (rotary potentiometers), and on each motor shaft to measure total displacement and velocity of each motor (a shaft encoder);
5) an inertial measurement unit (IMU) to determine the absolute position of the prosthesis in space;
6) a displacement sensor on each spring in order to measure the amount of force borne by a spring and the torque borne by the ankle joint; and
7) electromyographic (EMG) sensors to determine residual limb muscle activity.

Series spring displacement sensors can be used to determine the torque borne by the ankle joint because joint torque can be calculated from the agonist-antagonist spring output forces.

Control for Active Ankle-Foot Prosthesis

Local Prosthesis Control. A critical advantage of the human-like musculoskeletal prosthesis is that it allows the amputee user to directly control ankle powered plantar flexion. Because of the bi-articular ankle-knee mechanism, the extent of midstance knee extension defines how much energy is transferred to the prosthetic ankle for powering ankle plantar flexion at terminal stance. Since transtibial amputees generally have direct control over their knee, the biomimetic transtibial prosthesis allows for direct control over ankle power output.

The point in the gait cycle where the prosthesis series spring elements are engaged will largely be defined by joint state (position and velocity) and foot-ground interaction forces. The spring equilibrium angle for the ankle mono-articular mechanism will be equal to the ankle angle at first heel strike. Here heel strike will be detected using ankle torque sensing. For level ground ambulation, the heel strike ankle angle will be kept largely invariant with walking speed, but will be modulated from step to step for slope and stair ambulation.

The uni-directional clutch devices in the bi-articular mechanism will be controlled in a speed invariant manner. After heel strike in walking, the knee typically undergoes a flexion period. During that phase of gait, both bi-articular clutches will be disengaged, and therefore the bi-articular spring will not apply a force to the prosthesis skeleton. However, as the knee begins to extend (~10% cycle), both clutches will be engaged, causing the bi-articular spring to stretch. Once the prosthesis enters the swing phase as detected by zero ankle torque, the bi-articular clutches will be disengaged so as to allow unrestricted knee and ankle movement throughout the swing phase.

Electromyographic (EMG) Control of Prosthetic Ankle Stiffness. The residual anatomy will allow amputees to voluntarily control joint stiffness via activation of the muscles in the residual limb. When walking on a rigid ground surface, the amputee user can select a low ankle stiffness, whereas when walking on a compliant terrain, the amputee can exploit a relatively high ankle stiffness.

Within the human body, such voluntary changes in joint stiffness are modulated by muscular co-activation. When antagonist muscles are simultaneously recruited, the net torque produced about the joint is related to the difference between the forces generated by the activated muscles, while the joint stiffness is related to their sum. Thus, activity from residual muscles is a natural control source for specifying the desired level of ankle stiffness. Since EMG provides a measure of muscular effort, it can be used in a "natural" manner to control stiffness of a joint. For a transtibial amputee, the muscles of the anterior and posterior compartment of the leg form the natural location from which to derive stiffness control signals.

A joint stiffness control signal is derived from the sum of the plantar flexion and dorsiflexion EMG amplitudes. The stiffness control signal will be related to stiffness via a straight line relationship with a zero-level control signal signifying the minimum available stiffness level and the maximum-level control signal signifying the maximum available stiffness level. Thus, limited muscle effort results in a low ankle stiffness while high muscular effort results in a high ankle stiffness. Using this control strategy, stiffness can be volitionally controlled by the amputee in a natural manner.

Although the device of FIGS. 13A-13D was described as a transtibial prosthesis, the mechanism could also be used as an orthosis or exoskeleton. The mechanism would be useful as an orthosis for an individual that suffers from an ankle pathology but generally has normal knee and hip function. For such an application, the mechanism would be placed in parallel with the human leg to augment ankle mechanics as a permanent assistive device.

Mono and Bi-articular actuation for an Artificial Ankle and Knee System

Description

A proposed artificial ankle and knee system is shown in FIGS. 14A-D. The mechanism could be employed for a transfemoral prosthesis, orthosis, leg exoskeleton, or robotic leg. The mono-articular ankle-foot 1303 and knee 1401 designs are identical to the structures described in FIG. 13B and FIG. 8, respectively. However, the ankle-knee bi-articular mechanism 1410 is different from that proposed in FIGS. 13C and 13D. The bi-articular device of FIG. 13 has to be attached above the knee axis. In distinction, the bi-articular device 1410 of FIGS. 14A-14D attaches adjacent to the knee axis.

Figure 14A:
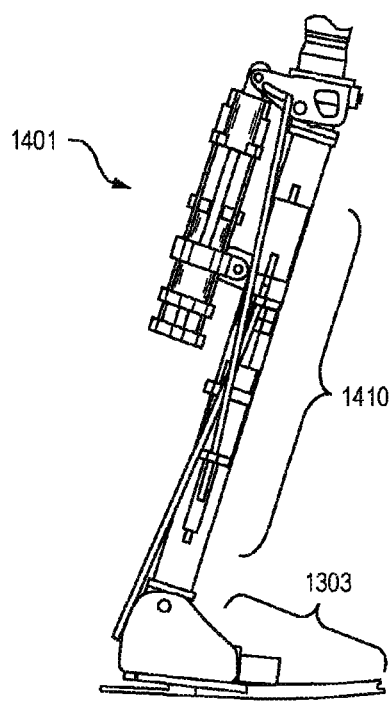
FIGS. 14A and 14B shows the major components of an artificial ankle and knee system.
Figure 14B:
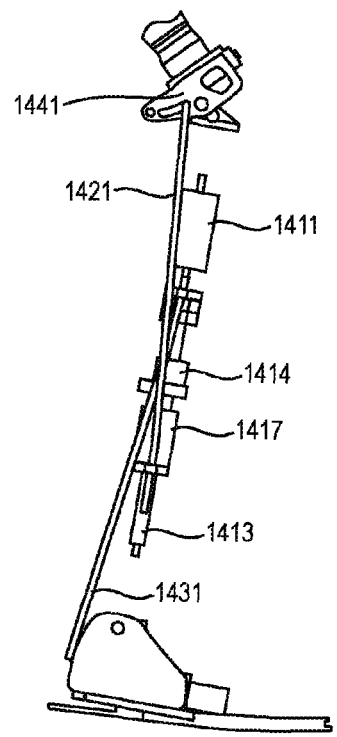
Figure 14C:
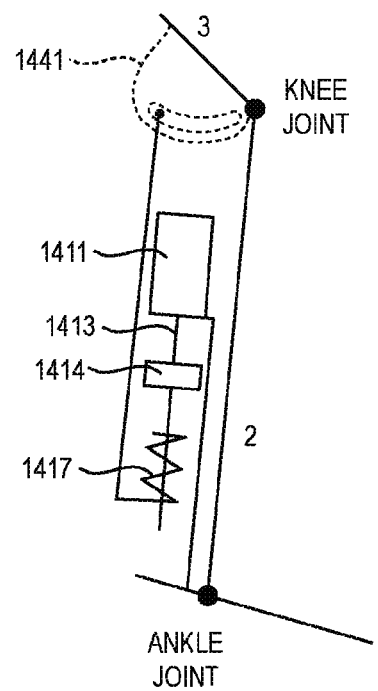
FIG. 14C is a schematic diagram of the artificial ankle and knee system seen in FIGS. 14A and 14B.
Figure 14D:
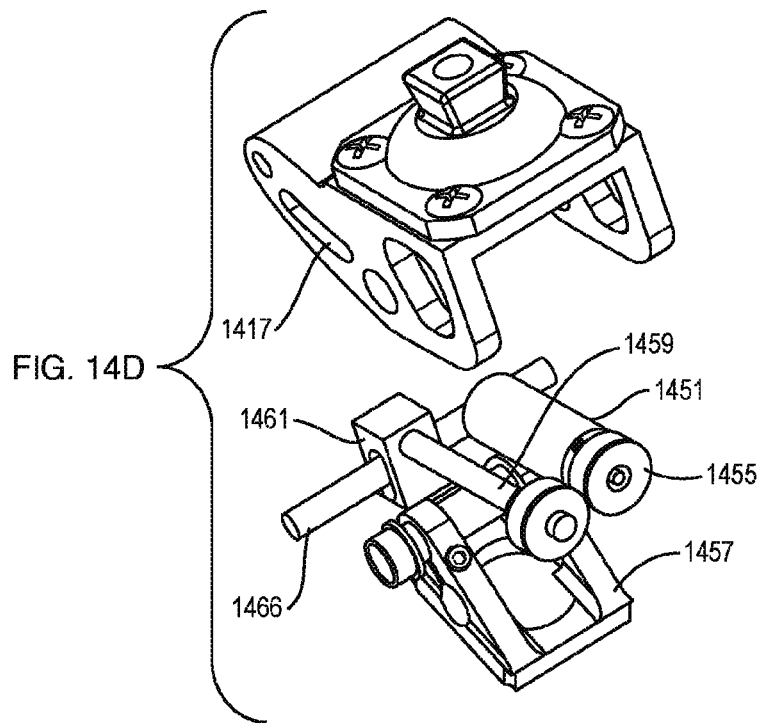
FIG. 14D shows the knee's variable moment arm (VMA) device (seen at the top of FIGS. 14A and 14B) in more detail.

The bi-articular ankle-knee mechanism of FIGS. 14A-14D comprises a motor 1411, non-backdriveable mechanical transmission 1413, screw nut 1414, series spring 1417, a knee bi-articular connection 1421, an ankle bi-articular connection 1431, and a knee variable moment arm (VMA) device 1441 (seen in more detail in FIG. 14D).

During level-ground walking, we describe how the ankle-knee bi-articular mechanism would be controlled for the swing, early stance flexion, mid-stance extension, and pre-swing phases of gait.

During the swing phase and early stance knee flexion, the screw nut 1414 is moved away from the series spring 1417 so that ankle and knee joint movements do not cause the spring to compress. However, when stance knee extension begins (18% gait cycle), the lead screw nut 1414 is moved by the motor 1411 until it engages the series spring 1417. As a consequence of this control action, both knee extension and ankle dorsiflexion contributes to spring compression. Once the knee has reached full extension, the VMA device 1441 then minimizes the moment arm that the knee bi-articular connection makes with the knee axis of rotation. Because the knee moment arm is minimized, most of the strain energy stored in the bi-articular spring contributes to ankle powered plantar flexion at terminal stance. Generally, the knee moment arm 1441 can be controlled to effectively modulate the amount of energy release that occurs through the knee joint.

The VMA device comprises a small motor 1451 plus gear train 1455, non-backdriveable lead screw 1459, lead screw nut 1461, and variable moment arm pin 1466. A shin tube mount is seen at 1457. When the motor 1451 rotates, the lead screw nut 1461 moves the variable moment arm pin 1466 across the variable moment arm slot 1471. The pin is attached to the knee bi-articular connection. Thus, the VMA motor can actively control the perpendicular distance, or moment arm, between the knee bi-articular connection and the knee axis.

Summary

Several agonist-antagonist actuator variations comprising a plurality of active element transmission-spring combinations acting in parallel have described. These actuator embodiments combine active and passive elements in order to achieve high performance with minimal mass. In addition, the use of agonist-antagonist actuators as mono and poly-articular linear elements has been described. The combination of biologically-inspired musculoskeletal architectures and agonist-antagonist actuation strategies as described above provide novel, low mass, efficient and quiet biomimetic artificial limbs. These artificial limb structures may be used to advantage to provide improved orthotic and prosthetic devices and legged robotic mechanisms.

Conclusion

It is to be understood that the methods and apparatus which have been described above are merely illustrative applications of the principles of the invention. Numerous modifications may be made by those skilled in the art without departing from the true spirit and scope of the invention.

What is claimed is:

1. An agonist-antagonist actuator for controlling an orthotic, prosthetic or exoskeleton joint comprising, in combination:
   a flexion actuator connected to each of first and second members that are connected for movement relative to one another about a single pivot point, whereby the single pivot point maintains a length of the orthotic, prosthetic or exoskeleton joint throughout flexion and extension of the first and second members of the orthotic, prosthetic or exoskeleton joint about the single pivot point, and wherein the flexion actuator includes a series combination of a first active element and a first elastic element, the flexion actuator being configured to draw the first and second members together, reducing the angle between the first and second members at the joint;
   an extension actuator connected between the first and second members, the extension actuator comprising a series combination of a second active element and a second elastic element, the extension actuator being configured to urge the first and second members apart, increasing the angle between the first and second members at the joint, the extension actuator being in parallel with the flexion actuator, being independently activated at different moments in time from the flexion actuator, and operating to oppose the flexion actuator in an agonist-antagonist manner, whereby simultaneous actuation of the flexion actuator and the extension actuator will cause the actuators to operate in active opposition to each other about the single pivot point of the orthotic, prosthetic or exoskeleton joint; and
   a controller for independently energizing the first active element and the second active element at different moments in time to control the movement of the first and second members at the orthotic, prosthetic or exoskeleton joint.

2. The agonist-antagonist actuator of claim 1, wherein the first and second active elements comprise motors.

3. The agonist-antagonist actuator of claim 2, wherein the motors are electric motors.

4. The agonist-antagonist actuator of claim 2, further comprising a first transmission connecting the first active element to the first elastic element and a second transmission connecting the second active element to the second elastic element.

5. The agonist-antagonist actuator of claim 4, wherein the transmissions are non-backdriveable.

6. The agonist-antagonist actuator of claim 1, wherein the first and second elastic elements comprise springs.

7. The agonist-antagonist actuator of claim 6, wherein the springs are hardening springs.

8. The agonist-antagonist actuator of claim 6, wherein each of the springs has a different stiffness.

9. The agonist-antagonist actuator of claim 1, wherein the orthotic, prosthetic or exoskeleton joint is an ankle joint and the flexion and extension actuators cooperatively operate such that energy is stored in the first elastic element during controlled plantarflexion and energy is stored in the second elastic element during controlled dorsiflexion.

10. The agonist-antagonist actuator of claim 1, wherein the orthotic, prosthetic or exoskeleton joint is a knee joint and the flexion and extension actuators cooperatively operate such that energy is stored in the second elastic element during stance flexion and energy is stored in the first elastic element during stance extension.

11. The agonist-antagonist actuator of claim 1, wherein the orthotic, prosthetic or exoskeleton joint is a knee joint and the flexion and extension actuators cooperatively operate such that energy is stored in the second elastic element during early swing and energy is stored in the first elastic element during late swing.

12. An orthotic, prosthetic or exoskeleton joint with agonist-antagonist actuator control, comprising, in combination:
an orthotic, prosthetic or exoskeleton joint, the orthotic, prosthetic or exoskeleton joint including first and second members, and a single pivot point linking the first and second members for movement relative to one another at the single pivot point, the single pivot point maintaining a length of the orthotic, prosthetic or exoskeleton joint during rotation of the first and second members about the single pivot point;
a flexion actuator spanning the orthotic, prosthetic or exoskeleton joint and connected to each of the first and second members, the flexion actuator comprising a series combination of a first active element and a first elastic element, the flexion actuator being configured to draw the first and second members together, reducing the angle between the first and second members at the joint;
an extension actuator spanning the orthotic, prosthetic or exoskeleton joint and connected between the first and second members, the extension actuator comprising a series combination of a second active element and a second elastic element, the extension actuator being configured to urge the first and second members apart, increasing the angle between the first and second members at the joint, the extension actuator being in parallel with the flexion actuator, being independently activated at different moments in time from the flexion actuator, and operating to oppose the flexion actuator in an agonist-antagonist manner, whereby simultaneous actuation of the flexion actuator and the extension actuator will cause the actuators to operate in active opposition to each other about the single pivot point of the orthotic, prosthetic or exoskeleton joint; and
a controller for independently energizing the first active element and the second active element at different moments in time to control the movement of the first and second members at the orthotic, prosthetic or exoskeleton joint.

13. The orthotic, prosthetic or exoskeleton joint of claim 12, wherein the first and second active elements comprise motors.

14. The orthotic, prosthetic or exoskeleton joint of claim 13, further comprising a first transmission connecting the first active element to the first elastic element and a second transmission connecting the second active element to the second elastic element.

15. The orthotic, prosthetic or exoskeleton joint of claim 12, wherein the first and second elastic elements comprise springs.

16. The orthotic, prosthetic or exoskeleton joint of claim 12, wherein the orthotic, prosthetic or exoskeleton joint is an ankle joint and the flexion and extension actuators cooperatively operate such that energy is stored in the first elastic element during controlled plantarflexion and energy is stored in the second elastic element during controlled dorsiflexion.

17. The orthotic, prosthetic or exoskeleton joint of claim 12, wherein the orthotic, prosthetic or exoskeleton joint is a knee joint and the flexion and extension actuators cooperatively operate such that energy is stored in the second elastic element during stance flexion and energy is stored in the first elastic element during stance extension.

18. The orthotic, prosthetic or exoskeleton joint of claim 12, wherein the orthotic, prosthetic or exoskeleton joint is a knee joint and the flexion and extension actuators cooperatively operate such that energy is stored in the second elastic element during early swing and energy is stored in the first elastic element during late swing.

* * * * *